(12) United States Patent
Hariton

(10) Patent No.: US 12,115,005 B2
(45) Date of Patent: Oct. 15, 2024

(54) SYSTEMS AND METHODS FOR PROCESSING RETINAL SIGNAL DATA AND IDENTIFYING CONDITIONS

(71) Applicant: DIAMENTIS INC., Quebec (CA)

(72) Inventor: Claude Hariton, Saint Antoine de Tilly (CA)

(73) Assignee: DIAMENTIS INC., Quebec (CA)

( * ) Notice: Subject to any disclaimer, the term of this patent is extended or adjusted under 35 U.S.C. 154(b) by 607 days.

(21) Appl. No.: 17/212,410

(22) Filed: Mar. 25, 2021

(65) Prior Publication Data

US 2021/0298687 A1 Sep. 30, 2021

Related U.S. Application Data

(60) Provisional application No. 63/149,508, filed on Feb. 15, 2021, provisional application No. 63/038,257, (Continued)

(51) Int. Cl.
*A61B 5/00* (2006.01)
*A61B 5/16* (2006.01)
*G16H 50/20* (2018.01)

(52) U.S. Cl.
CPC .......... *A61B 5/7275* (2013.01); *A61B 5/0059* (2013.01); *A61B 5/16* (2013.01); (Continued)

(58) Field of Classification Search
CPC ....... A61B 5/7275; A61B 5/0059; A61B 5/16; A61B 5/4082; A61B 5/4088; A61B 5/4839; A61B 5/7267; A61B 5/742; A61B 5/7475
(Continued)

(56) References Cited

U.S. PATENT DOCUMENTS

| 7,338,455 B2 | 3/2008 | White et al. |
| 7,670,764 B2 | 3/2010 | Oh et al. |

(Continued)

FOREIGN PATENT DOCUMENTS

| RU | 2141245 C1 | 11/1999 |
| WO | 2007061469 A1 | 5/2007 |

(Continued)

OTHER PUBLICATIONS

Lopez-Dorado, A. et al., Diagnosis of multiple sclerosis using multifocal ERG data feature fusion, Information Fusion 76, p. 157-167, May 25, 2021.

(Continued)

*Primary Examiner* — Michael J Lau
(74) *Attorney, Agent, or Firm* — BCF LLP

(57) ABSTRACT

There is disclosed a method and system for predicting a likelihood that a patient is subject to one or more conditions. Retinal signal data corresponding to the patient may be received. Retinal signal features may be extracted from the retinal signal data. Descriptors may be extracted from the retinal signal features. The descriptors may be applied to a first mathematical model and a second mathematical model. The first mathematical model may correspond to a first condition. The second mathematical model may correspond to ta second condition. A first predicted probability for the first condition may be generated. A second predicted probability for the second condition may be generated. The first predicted probability and the second predicted probability may be output.

18 Claims, 58 Drawing Sheets
(52 of 58 Drawing Sheet(s) Filed in Color)

Related U.S. Application Data filed on Jun. 12, 2020, provisional application No. 63/000,055, filed on Mar. 26, 2020.

(52) U.S. Cl.
CPC .......... *A61B 5/4082* (2013.01); *A61B 5/4088* (2013.01); *A61B 5/4839* (2013.01); *A61B 5/7267* (2013.01); *A61B 5/742* (2013.01); *A61B 5/7475* (2013.01); *G16H 50/20* (2018.01)

(58) Field of Classification Search
USPC ........................................ 600/300
See application file for complete search history.

(56) References Cited

U.S. PATENT DOCUMENTS

| | | | |
|---|---|---|---|
| 7,959,578 B2 | 6/2011 | Lonky | |
| 8,078,267 B2* | 12/2011 | Gellerman | A61B 5/0059 600/407 |
| 2004/0114109 A1* | 6/2004 | Soliz | A61B 5/14555 351/221 |
| 2006/0122529 A1* | 6/2006 | Tsau | H03F 3/45 600/544 |
| 2006/0164653 A1* | 7/2006 | Everett | G01B 9/02048 356/479 |
| 2007/0135727 A1 | 6/2007 | Virtanen et al. | |
| 2009/0105605 A1* | 4/2009 | Abreu | A61B 5/0075 600/549 |
| 2009/0227891 A1* | 9/2009 | Peyman | A61B 3/12 600/558 |
| 2009/0257023 A1 | 10/2009 | Greenlee et al. | |
| 2011/0190657 A1* | 8/2011 | Zhou | G16H 50/70 600/558 |
| 2011/0245169 A1 | 10/2011 | Brines et al. | |
| 2011/0245734 A1 | 10/2011 | Wagner et al. | |
| 2011/0275927 A1 | 10/2011 | Wagner et al. | |
| 2011/0286932 A1* | 11/2011 | Koronyo | A61P 27/12 424/9.6 |
| 2011/0318346 A1* | 12/2011 | Steinman | A61K 39/395 514/17.7 |
| 2012/0093772 A1 | 1/2012 | Horsager et al. | |
| 2012/0053242 A1 | 3/2012 | Cela Lopez | |
| 2012/0059060 A1 | 3/2012 | Blanda et al. | |
| 2012/0142589 A1 | 6/2012 | Brines et al. | |
| 2013/0296710 A1* | 11/2013 | Zuzak | G01J 3/10 600/476 |
| 2015/0105689 A1* | 4/2015 | Miller | A61B 5/167 600/558 |
| 2015/0245766 A1* | 9/2015 | Rennaker | G16H 40/63 351/210 |
| 2015/0342495 A1 | 12/2015 | Quentin et al. | |
| 2016/0015470 A1* | 1/2016 | Border | A61B 1/00 600/117 |
| 2016/0029919 A1* | 2/2016 | Hebert | A61B 5/165 600/558 |
| 2016/0270656 A1* | 9/2016 | Samec | A61B 3/1216 |
| 2017/0173262 A1* | 6/2017 | Veltz | G16H 20/17 |
| 2017/0238877 A1 | 8/2017 | Yi-Sing et al. | |
| 2017/0348434 A1* | 12/2017 | Leveillard | A61P 9/10 |
| 2017/0354326 A1* | 12/2017 | Pugh | A61B 5/398 |
| 2018/0190011 A1* | 7/2018 | Platt | G02B 27/017 |
| 2018/0278924 A1* | 9/2018 | Schowengerdt | G02B 27/0172 |
| 2018/0353073 A1* | 12/2018 | Boucher | A61B 5/05 |
| 2019/0127684 A1* | 5/2019 | Rizzolo | A61L 27/26 |
| 2019/0175120 A1* | 6/2019 | Huang | A61B 5/72 |
| 2019/0209497 A1* | 7/2019 | Ma | A61K 31/4535 |
| 2019/0278093 A1* | 9/2019 | Osterhout | G09G 5/003 |
| 2020/0029851 A1* | 1/2020 | Siwoff | A61B 5/6814 |

FOREIGN PATENT DOCUMENTS

| | | |
|---|---|---|
| WO | 2011133890 A1 | 10/2011 |
| WO | 2011119869 A1 | 11/2011 |
| WO | 2012021773 A1 | 2/2012 |
| WO | 2012051599 A1 | 4/2012 |
| WO | 2012116334 A3 | 8/2012 |
| WO | 2014197822 A2 | 12/2014 |
| WO | 2020118160 A1 | 6/2020 |
| WO | 2022087529 A1 | 4/2022 |

OTHER PUBLICATIONS

Chiquita, S. et al., The retina as a window or mirror of the brain changes detected in Alzheimer's disease: Critical aspects to unravel, Molecular Neurobiology, 56:5416-5435, 2019.

Asanad, S. et al., Retinal ganglion cell dysfunction in preclinical Alzheimer's disease: an electrophysiologic biomarker signature, Scientific Reports, 11:6344, 2021.

Constable, P. et al., Light-adapted electroretinogram differences in Autism Spectrum Disorder, Journal of Autism and Developmental Disorders, Feb. 7, 2020.

Demmin, D. et al., Electroretinographic anomalies in Schizophrenia, Journal of Abnormal Psychology, vol. 127, No. 4, pp. 417-428, 2018.

Peredo, R. et al., Electroretinography may reveal cognitive impairment among a cohort of subjects at risk of a major psychiatric disorder, Psychiatry Research 291, 113227, 2020.

Silverstein, S. et al., Measures of retinal structure and function as biomarkers in neurology and psychiatry, Biomarkers in Neuropsychiatry 2, 100018, 2020.

Diagnosys LLC, Electrodes for Clinical Practice, Feb. 10, 2021.

Harrison, W. et al., Multifocal electroretinograms predict onset of Diabetic Retinopathy in adult patents with diabetes, Invest. Ophthalmol. Vis. Sci. 2011;52(2), 772-777.

Balogh et al., Retinal dysfunctions in schizophrenia, Progress in neuro-psychopharmacology & biological psychiatry, 32 (2008) 297-300.

Barraco et al., A comparison among different techniques for human ERG signals processing and classification, Physica Medica 2013.

Barraco et al., An approach based on wavelet analysis for feature extraction i the a-wave of the electroretinogram, Comput Met Prog Biomed, Elsevier Health, 2011.

Bubl et al., Seeing gray when feeling blue? Depression can be measured in the eye of the diseased, Biol Psychiatry, 2010.

Bubl et al., Effect of antidepressive therapy on retinal contrast processing in depressive disorder, This British Journal of Psychiatry 2012.

Castrogiovanni et al., Electroretinogram B-wave amplitude in panic disorder, 2001.

Electroretinograms, Gregor Belusic, free online editions of In Tech Books and Journals can be found at www.intechopen.com, 2011.

Fam et al., Visual contrast sensitivity in major depressive disorder, Journal of psychosomatic Research 2013.

Fornaro et al., Electroretinographic assessment in major depressed patients receiving duloxetine: Might differences between responders and non-responders indicate a differential biological background?, J Affect Disord 2011.

Forte et al., Wavelet analysis reveals dynamics of rat oscillatory potentials, J. Neurosci Met 2008.

Fountoulakis et al., Is there a dysfunction on the visual system of depressed patients?, Annals Gen Psyc, Mar. 2005.

Gagne et al., Atypical pattern of rod electroretinogram modulation by recent light history: A possible miomarker of seasonal affective disorder, 2011.

Gschwandtner et al., EEG: a helpful tool in the prediction of psychosis, Eur. Arch. Psychiatry Clin. Neurosci., vol. 259, p. 257-262, Apr. 11, 2009.

Hebert et al., Retinal response to light in young nonaffected offspring at high genetic risk of neuropsychiatric brain disorders, Reseach Report, Biol Psychiatry 2010.

Hebert et al., Electroretinography in patents with winter seasonal affective disorder, Psychiatry Research 127, 2004.

Holopigian et al., The effects of dopamine blockade on the human flash electroretinogram, Documenta Ophthalmologica 86: 1-10, 1994.

(56) References Cited

OTHER PUBLICATIONS

Jahshan et al., Nonconscious and conscious color priming in schizophrenia, Journal of Psychiatric Research 2012.
Lam et al., Electroretinography in seasonal affective disorder, Psychiatry Res 1992.
Lavoie et al., Electroretinogram anomalies in Psychiatric disorders: The possible implication of GSK3, May 10, 2012.
Lavoie et al., The electroretinogram as a biomarker of central dopamine and serotonin: potential relevance to psychiatric disorders, Biol. Psychiatry, vol. 75, No. 6, pp. 479-486, Jan. 7, 2013.
Llewellyn, If waking and dreaming consciousness became de-differentiated, would schizophrenia result?, Consciousness and Cognition, Elsevier Inc 2011.
Hori et al., Several prescription patterns of antipsychotic drugs influence cognitive functions in Japanese chronic schizophrenia patents, Abstracts of the 3rd Biennial Schizophrenia International Reseach Conference / Schizophrenia Research 136, Supplement 1, S1-S375, 2012.
Maziade et al., Shared and specific susceptibility loci for schizophrenia and bipolar disorder: a dense genome scan in Eastern Quebec families, Molecular Psychiatry, 10, 486-499, 2005.
Miller, Functional neuro-ophthalmology, Handbook of Clinical Neurology, vol. 102, 2011.
Realmuto et al., Electroretinograms (ERGs) in Four Autistic Probands and Six First-Degree Relatives, Canadian vol. of Psychiatry 1989.
Schechter, Electroniretinographic assessment in schizophrenia, Elec Clin Neuro Suppl., 1987.
Seggie et al., Electroretinographic (ERG) changes in Depression, Clin Invest Med, 1990.
Tzelepi, The push-pull action of dopamine on spatial tuning of the monkey retina: the effects of dopaminergic deficiency and selective D1 and D2 receptor ligands on the pattern electroretinogram, Vision Research 38, 1479-1487, 1998.
Warner et al., Retinal function as a marker for cell membrane Omega-3 fatty acid depletion in schizophrenia: a pilot study, Biol Psychiatry 1999; 45:1138-1142.
Yeap et al., Visual sensory processing deficits in schizophrenia and their relationship to disease state, Eur Arch Psychiatry Clin Neurosci (2008) 258:305-3016.
Lavoie et al., Evidence of a biological effect of light therapy on the retina of patients with seasonal affective disorder, Biological Psychiatry, vol. 63, No. 3, 2009.
Fournier et al., Prediction of response to medication and cognitive therapy in the treatment of moderate to severe depression, J. Consult. Clin. Psychol., 77(4): 775-87, Aug. 2009.
Debuc et al., Retinal microvascular network alterations: potential biomarkers of cerebrovascular and neurol diseases, Am J Physiol Heart Cir Physiol 312: H201-H212, 2017.
Macgillivray et al., Retinal imaging as a source of biomarkers for diagnosis characterization and prognosis of chronic illness or long-term conditions, Br J Radiol 2014.
Johnson et al., The photomyoclonic reflex: an artefact in the clinical electroretinogram, British Journal of Ophtalmology, 1982.
International Search Report and Written Opinion issued in co-pending application No. PCT/CA2021/050796 on Sep. 8, 2021.
Hebert, M. et al., The Electroretinogram may differentiate schizophrenia from bipolar disorder, Biological Psychiatry, Elsevier, vol. 87, No. 3, Jun. 27, 2019, pp. 263-270.
Youssef, P. et al., Electroretinography in psychiatry: A systematic literature review, European Psychiatry, Editions Scientifiques et Medicales Elsevier, vol. 62, Sep. 22, 2019, pp. 97-106.
Anonymous, Electroretinogram—EyeWiki, Oct. 17, 2015, https://eyewiki.aao.org/w/index.php?title=Electroretinogram&oldid=47754.
Supplementary European Search Report issued in co-pending European patent application No. 21774883.9 on Mar. 5, 2024.
European Search Report issued in co-pending European patent application No. 21821168.8 on Jul. 9, 2024.

* cited by examiner

SYSTEMS AND METHODS FOR PROCESSING RETINAL SIGNAL DATA AND IDENTIFYING CONDITIONS

CROSS-REFERENCE TO RELATED APPLICATIONS

This application claims the benefit of U.S. Provisional Patent Application No. 63/000,055, filed Mar. 26, 2020, U.S. Provisional Patent Application No. 63/038,257, filed Jun. 12, 2020, and U.S. Provisional Patent Application No. 63/149,508, filed Feb. 15, 2021, each of which is incorporated by reference herein in its entirety.

FIELD

The present technology relates to systems and methods for processing retinal signal data generated by light stimulation.

BACKGROUND

Clinicians may wish to determine whether a patient is subject to a medical condition, such as a psychiatric condition or a neurological condition. The clinician may compare the patient to known criteria in order to determine which condition a patient is subject to. In some instances, the patient may fit multiple conditions, and it may be difficult or impossible for the clinician to differentiate between the conditions. It may be preferable if the clinician had a tool to aid in determining and/or confirming whether a patient is subject to a medical condition and/or differentiating between those conditions.

It is an object of the present technology to ameliorate at least some of the limitations present in the prior art.

SUMMARY

Embodiments of the present technology have been developed based on developers' appreciation of certain shortcomings associated with existing systems for determining medical conditions.

The identification of biomarkers and/or biosignatures of conditions, such as for example psychiatric, mental or neurological conditions, for example, schizophrenia, bipolar I disorder, or depression, may allow healthcare professionals to make an earlier determination of a condition, identify which condition a patient is subject to when there are multiple candidate conditions, and/or deliver early and possibly preventative interventions. This early determination of a medical condition may improve the treatment of patients and/or their prognosis.

Embodiments of the present technology have been developed based on the developers' observation that data obtained in electroretinograms (ERG) may provide some insight into determining medical conditions. However, existing methods to collect and analyse electroretinograms (ERG) can only collect and analyse a limited volume of information from the captured electrical signals. It was found that expansion of the volume of information collected regarding retinal response to light stimulation allowed generating retinal signal data with a higher density of information, a higher volume of information, and/or additional types of information. This retinal signal data enables a multimodal mapping of the electrical signals and/or other data and allows the detection of additional features in the multimodal mapping specific to certain conditions. The multimodal mapping may include multiple parameters of the retinal signal data, such as time, frequency, light stimulation parameters, and/or any other parameter.

Embodiments of the present technology form the basis for a refined methodology of determining medical conditions based on a processing of retinal signal data which has more volume of information, more density of information and/or additional types of information detail compared to traditional ERG data, and which has been named herein "retinal signal processing and analysis" (RSPA). This retinal signal data allows, in certain embodiments, the mathematical modeling of datasets containing a multiplicity of information, identification of retinal signal features, and the ability to identify biomarkers and/or biosignatures in the retinal signal data using for example the retinal signal features. Certain, non-essential, embodiments of the present technology also provide methods for collecting the retinal signal data which has more volume of information, more density of information and/or additional types of information compared to ERG data.

In certain embodiments of the present technology, a more accurate detection of certain medical conditions or a more discriminant separation between medical conditions may be attained. The detection of medical conditions or discriminant separation between conditions may be attained within the diversity of related (e.g., gender, age, onset of disease, retinal pigmentation, iris color) and/or confounding factors (e.g. onset of conditions, use of drugs, effects of some treatments, episodes of psychosis, anxiety, depression, overlap of signs and symptoms common to several disorders). The increase in the level of detail and/or the number of retinal signal features the technology is able to capture and to analyse has a direct impact on the potential to identify biosignatures using retinal signal data in order to better discriminate between conditions, such as pathological conditions, as well as better depict the conditions as compared to a control (which may be referred to as a non-pathological condition). For example, embodiments of present methods may be based on retinal signal data captured at a higher sampling frequency and/or for a longer period of time compared to conventional ERG. The retinal signal data may include additional features recorded with the electrical signals, such as, but not limited to, impedance, light wavelength, light spectrum, or light intensity reaching the retina. The capture of additional information, at a higher sampling frequency, and/or data collected with an extended range of retinal light stimulation over an extended period of time, and its multi-dimensional representation, may be referred to as a "high density retinal signal data." The retinal signal data captured with high density may comprise more information than the data captured previously during an ERG (referred to as "conventional ERG"). The retinal signal data may be voltage-independent and/or time-independent, unlike conventional ERG.

In certain embodiments, a more efficient processing of retinal signal data is possible using high density retinal signal data. The advantage of high density retinal signal data as compared to the conventional ERG data, is to benefit from a larger amount of information related to the electrical signals and additional retinal signal features and therefore a more detailed biosignature. With a higher level of detail, it is therefore possible to better discriminate among different conditions and prepare a series of classifiers representative of the biosignature features of each condition.

According to a first broad aspect of the present technology, there is provided a method for generating a mathematical model corresponding to a first condition, the method executable by at least one processor of a computer system, the method comprising: generating a mathematical model corresponding to a first condition, the method executable by at least one processor of a computer system, the method comprising: receiving a plurality of datasets of labelled retinal signal data corresponding to a plurality of patients, wherein each dataset comprises retinal signal data of a patient and a label, wherein the label indicates whether the patient is subject to the first condition; extracting a set of features from the retinal signal data; selecting a subset of features from the set of features, wherein the subset of features corresponds to biomarkers of the first condition; and determining, based on the subset of features, one or more classifiers that distinguish the first condition from a second condition.

In some implementations of the method, the set of features comprise voltage, circuit impedance, signal collection time, sampling frequency, light stimulation synchronization time, light stimulation offset, or indications of which retinal areas were illuminated.

In some implementations of the method, the set of features comprise eye position, pupil size, intensity of applied luminance, frequency of light stimulation, frequency of retinal signal sampling, wavelength of illumination, illumination time, background wavelength, or background luminance.

In some implementations of the method, the one or more classifiers distinguish a biosignature of the first condition from a biosignature of the second condition.

In some implementations of the method, the method further comprises ranking the set of features based on a relevance of each feature to the biosignature of the first condition, and wherein selecting the subset of features comprises selecting highest-ranked features of the set of features.

In some implementations of the method, the method further comprises: receiving clinical information cofactors corresponding to the plurality of patients, wherein each dataset comprises clinical information cofactors of the patient; and selecting a subset of the clinical cofactors, wherein the clinical cofactors in the subset of clinical cofactors influence detection of the biomarkers.

In some implementations of the method, the clinical information cofactors indicate an age, gender, skin pigmentation, or iris color of the respective patient.

In some implementations of the method, determining the one or more classifiers comprises determining, based on the subset of the clinical cofactors, the one or more classifiers.

In some implementations of the method, the method further comprises generating, based on the one or more classifiers, the mathematical model.

In some implementations of the method, the method further comprises: inputting, to the mathematical model, retinal signal data and clinical information cofactors corresponding to a patient; and outputting, by the mathematical model, a predicted likelihood that the patient is subject to the first condition.

In some implementations of the method, the method further comprises: inputting, to the mathematical model, retinal signal data and clinical information cofactors corresponding to a patient; and outputting, by the mathematical model, a predicted likelihood that the patient is not subject to the first condition.

In some implementations of the method, the first condition is schizophrenia, bipolar disorder, major depression disorder, or psychosis.

In some implementations of the method, the first condition is post-traumatic stress disorder, stroke, substance abuse, obsessive compulsive disorder, Alzheimer's, Parkinson's, multiple sclerosis, autism, or attention deficit disorder.

In some implementations of the method, the retinal signal data has a sampling frequency between 4 to 24 kHz.

In some implementations of the method, the retinal signal data is collected for a signal collection time of 200 milliseconds to 500 milliseconds.

In some implementations of the method, the retinal signal data comprises an impedance component of a receiving circuit recorded continuously while capturing the retinal signal data.

In some implementations of the method, the retinal signal data comprises one or more optical parameters.

In some implementations of the method, the optical parameters comprise luminance of retinal light stimulation or pupil size.

According to another broad aspect of the present technology, there is provided a method for predicting a probability that a patient is subject to one or more conditions, the method executable by at least one processor of a computer system, the method comprising: receiving retinal signal data corresponding to the patient; extracting, from the retinal signal data, one or more retinal signal features; extracting, from the retinal signal features, one or more descriptors; applying the one or more descriptors to a first mathematical model and a second mathematical model, wherein the first mathematical model corresponds to a first condition and the second mathematical model corresponds to a second condition, thereby generating a first predicted probability for the first condition and a second predicted probability for the second condition; and outputting the first predicted probability and the second predicted probability.

In some implementations of the method, the method further comprises displaying an interface comprising the first predicted probability and the second predicted probability.

In some implementations of the method, the method further comprises storing the first predicted probability and the second predicted probability.

In some implementations of the method, the method further comprises collecting the retinal signal data.

In some implementations of the method, the method further comprises: obtaining clinical information cofactors extracted from clinical information corresponding to the patient; and applying the clinical information cofactors to the first mathematical model and the second mathematical model.

In some implementations of the method, the clinical information cofactors correspond to an age, gender, skin pigmentation, or iris color of the patient.

In some implementations of the method, the retinal signal data has a sampling frequency between 4 to 24 kHz.

In some implementations of the method, the retinal signal data is collected for a signal collection time of 200 milliseconds to 500 milliseconds.

In some implementations of the method, the retinal signal data comprises an impedance component of a receiving circuit recorded continuously while capturing the retinal signal data.

In some implementations of the method, the retinal signal data comprises one or more optical parameters.

In some implementations of the method, the optical parameters comprise luminance of retinal light stimulation or pupil size.

In some implementations of the method, the first condition is a medical condition and wherein the second condition is a control condition.

In some implementations of the method, the first condition or the second condition is schizophrenia, bipolar disorder, major depression disorder, or psychosis.

In some implementations of the method, the first condition or the second condition is post-traumatic stress disorder, stroke, substance abuse, obsessive compulsive disorder, Alzheimer's, Parkinson's, multiple sclerosis, autism, or attention deficit disorder.

In some implementations of the method, the method further comprises receiving user input indicating a selection of the first condition and the second condition.

In some implementations of the method, the method further comprises: selecting, based on the first predicted probability and the second predicted probability, a medication; and administering the medication to the patient.

According to another broad aspect of the present technology, there is provided a method for determining a biosignature of a condition, the method executable by at least one processor of a computer system, the method comprising: receiving a plurality of datasets of labelled retinal signal data corresponding to a plurality of patients, wherein each dataset comprises retinal signal data of a patient and a label, wherein the label indicates whether the patient is subject to the condition; extracting a set of features from the retinal signal data; selecting a subset of features from the set of features, wherein the subset of features corresponds to biomarkers of the condition; and determining, based on the subset of features, one or more classifiers that identify the biosignature of the condition.

In some implementations of the method, the method further comprises: receiving clinical information cofactors corresponding to the plurality of patients, wherein each dataset comprises clinical information cofactors of the patient; and selecting a subset of the clinical cofactors, wherein the clinical cofactors in the subset of clinical cofactors influence detection of the biomarkers, and wherein determining the one or more classifiers comprises determining, based on the subset of clinical cofactors, the one or more classifiers.

In some implementations of the method, the method further comprises ranking the set of features based on a relevance of each feature to the biosignature of the first condition, and wherein selecting the subset of features comprises selecting highest-ranked features of the set of features.

According to another broad aspect of the present technology, there is provided a system for predicting a probability that a patient is subject to one or more conditions, the system comprising: a light stimulator; one or more sensors; a computer system comprising system comprising at least one processor and memory storing a plurality of executable instructions which, when executed by the at least one processor, cause the system to: cause the light stimulator to provide light stimulation signals to retina of the patient; collect, via the one or more sensors, electrical signals responsive to the light stimulation; generate, based on the electrical signals, retinal signal data corresponding to the patient; extract, from the retinal signal data, one or more retinal signal features; extract, from the retinal signal features, one or more descriptors; apply the one or more descriptors to a first mathematical model and a second mathematical model, wherein the first mathematical model corresponds to a first condition and the second mathematical model corresponds to a second condition, thereby generating a first predicted probability for the first condition and a second predicted probability for the second condition; and output the first predicted probability and the second predicted probability.

In some implementations of the system, the retinal signal data comprises a light wavelength component recorded while capturing the retinal signal data.

In some implementations of the system, the retinal signal data comprises a light spectrum component recorded while capturing the retinal signal data.

In some implementations of the system, the retinal signal data comprises a light intensity component recorded while capturing the retinal signal data.

In some implementations of the system, the retinal signal data comprises an illuminated retinal surface component recorded while capturing the retinal signal data. The retinal surface component may indicate a surface area of the retina that is illuminated.

According to another broad aspect of the present technology, there is provided a system for predicting a probability that a patient is subject to one or more conditions, the system comprising a computer system comprising at least one processor and memory storing a plurality of executable instructions which, when executed by the at least one processor, cause the computer system to: receive retinal signal data corresponding to the patient; extract, from the retinal signal data, one or more retinal signal features; extract, from the retinal signal features, one or more descriptors; apply the one or more descriptors to a first mathematical model and a second mathematical model, wherein the first mathematical model corresponds to a first condition and the second mathematical model corresponds to a second condition, thereby generating a first predicted probability for the first condition and a second predicted probability for the second condition; and output the first predicted probability and the second predicted probability.

In some implementations of the system, the system further comprises a light stimulator and one or more sensors, and the instructions, when executed by the at least one processor, cause the computer system to: cause the light stimulator to provide light stimulation signals to retina of the patient; collect, via the one or more sensors, electrical signals responsive to the light stimulation; and generate, based on the electrical signals, the retinal signal data.

In some implementations of the system, the system further comprises a display, and wherein the instructions, when executed by the at least one processor, cause the system to output, via the display, an interface comprising the first predicted probability and the second predicted probability.

According to another broad aspect of the present technology, there is provided a method for monitoring a condition of a patient, the method executable by at least one processor of a computer system, the method comprising: receiving retinal signal data corresponding to the patient; extracting, from the retinal signal data, one or more retinal signal features; extracting, from the retinal signal features, one or more descriptors; applying the one or more descriptors to a mathematical model corresponding to the condition, thereby generating a predicted probability for the condition; and outputting the predicted probability.

In some implementations of the method, the method further comprises: selecting, based on the predicted probability, a medication; and administering the medication to the patient.

In some implementations of the method, the retinal signal data comprises retinal signal data captured during treatment of the patient for the condition.

In some implementations of the method, the condition is schizophrenia, bipolar disorder, major depression disorder, psychosis, post-traumatic stress disorder, stroke, substance abuse, obsessive compulsive disorder, Alzheimer's, Parkinson's, multiple sclerosis, autism, or attention deficit disorder.

In the context of the present specification, unless expressly provided otherwise, a computer system may refer, but is not limited to, an "electronic device," an "operation system," a "system," a "computer-based system," a "controller unit," a "control device," and/or any combination thereof appropriate to the relevant task at hand.

In the context of the present specification, unless expressly provided otherwise, the expression "computer-readable medium" and "memory" are intended to include media of any nature and kind whatsoever, non-limiting examples of which include RAM, ROM, disks (CD-ROMs, DVDs, floppy disks, hard disk drives, etc.), USB keys, flash memory cards, solid state-drives, and tape drives.

In the context of the present specification, a "database" is any structured collection of data, irrespective of its particular structure, the database management software, or the computer hardware on which the data is stored, implemented or otherwise rendered available for use. A database may reside on the same hardware as the process that stores or makes use of the information stored in the database or it may reside on separate hardware, such as a dedicated server or plurality of servers.

In the context of the present specification, unless expressly provided otherwise, the words "first," "second," "third," etc. have been used as adjectives only for the purpose of allowing for distinction between the nouns that they modify from one another, and not for the purpose of describing any particular relationship between those nouns.

Embodiments of the present technology each have at least one of the above-mentioned object and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects and advantages of embodiments of the present technology will become apparent from the following description, the accompanying drawings and the appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a better understanding of the present technology, as well as other aspects and further features thereof, reference is made to the following description which is to be used in conjunction with the accompanying drawings, where.

Figure 1:
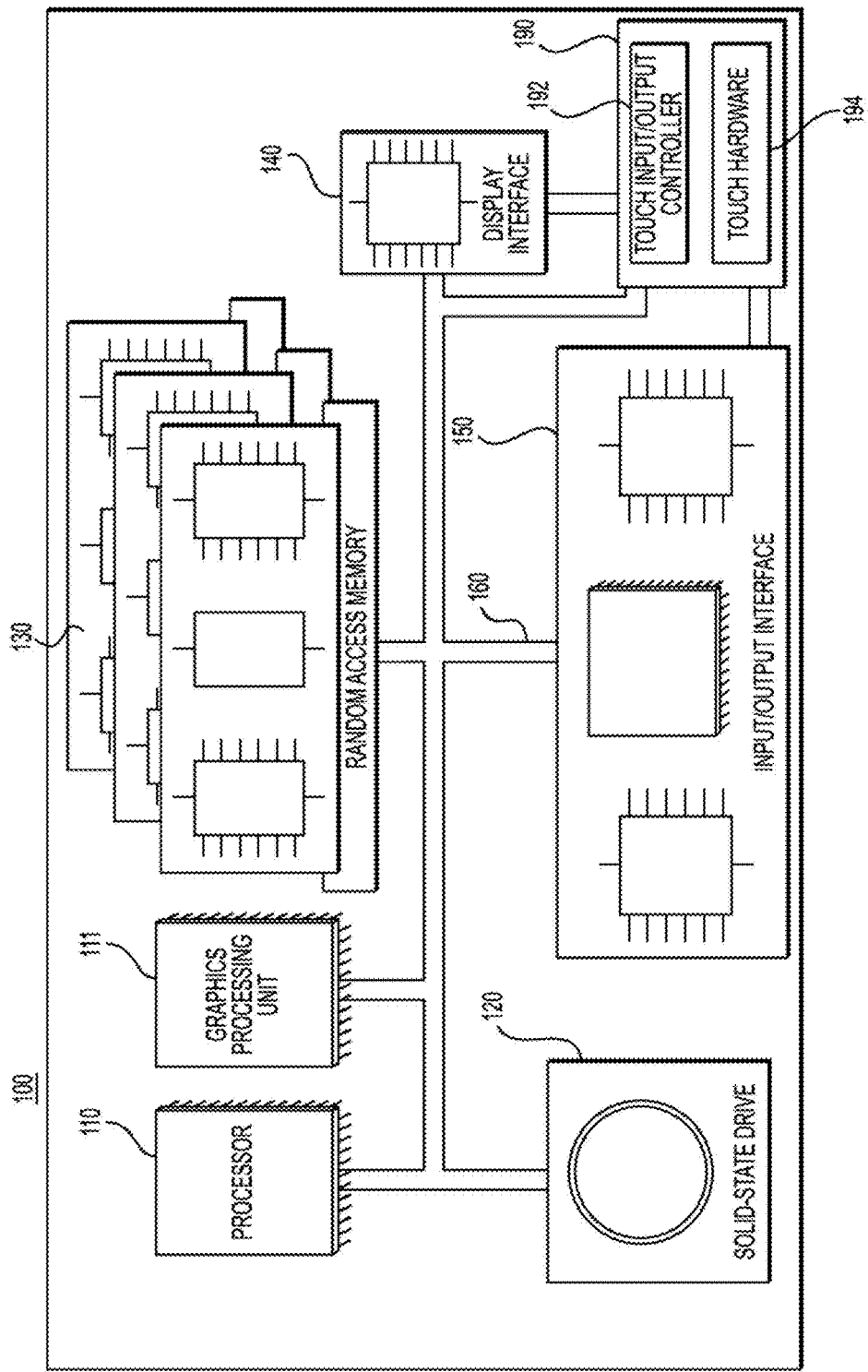
FIG. 1 is a block diagram of an example computing environment in accordance with various embodiments of the present technology.

It should be noted that, unless otherwise explicitly specified herein, the drawings are not to scale.

DETAILED DESCRIPTION

Certain aspects and embodiments of the present technology are directed to methods and systems for processing retinal signals. Broadly, certain aspects and embodiments of the present technology are based on retinal signal data with higher density, which may have been obtained in any manner such as by e.g. increasing the conditions for light stimulation (e.g. number and range of light intensities), adding dynamic resistance (impedance) of the circuit used to collect the electrical signals, capturing retinal signal data for a longer period of time, and/or capturing retinal signal data at a higher frequency. Present computer implemented methods are provided for analysing the retinal signal data and extracting retinal signal features used in combination to further decipher biomarkers and/or biosignatures in order to minimize, reduce, or avoid the limitations noted with the prior art. In certain optional embodiments, methods and systems are provided for capturing the high density retinal signal data.

Certain aspects and embodiments of the present technology provide methods and systems that can analyse retinal signal data and provide a predicted likelihood for specific conditions whilst taking into account a number of different clinical information cofactors. The conditions may be psychiatric conditions, psychological conditions, neurological conditions, and/or any other type of medical condition. The predicted likelihood may indicate that the patient is currently subject to a condition and/or that the patient is at-risk of developing the condition. For example if a patient's parent is subject to a condition, the patient's retinal signal data may be analyzed to determined whether the patient is likely to be subject to the same condition as their parent.

The systems and methods described herein may be fully or at least partially automated so as to minimize an input of a clinician in determining medical condition or a treatment plan for a medical condition. The predictions output by the systems and methods described herein may be used as an aid by a clinician while determining a medical condition and/or developing a treatment plan for a patient.

The systems and methods described herein may comprise generating a mathematical model for identifying a patient's distance from a biosignature of a condition by: 1) collecting retinal signal data from patients 2) labelling each patient's retinal signal data with a label indicating a potential medical condition of the patient (which may have been diagnosed by a clinician), 3) extracting retinal signal features from the retinal signal data, 4) selecting a subset of the features that correspond to biomarkers of the condition, and/or 5) determining classifiers that distinguish the biosignature of the condition from the biosignature of other conditions. The biosignature may comprise portions of the retinal signal data specific to a condition. The retinal signal data may comprise several biosignatures, where each biosignature is specific to a condition. The condition may be, but is not limited to, schizophrenia, bipolar disorder, major depression disorder, psychosis, post-traumatic stress disorder, stroke, substance abuse, obsessive compulsive disorder, Alzheimer's, Parkinson's, multiple sclerosis, autism, attention deficit disorder, and/or any other condition. These steps may be used to build a mathematical model of any condition which has a biomarker embedded in the retinal signal data. The steps for collecting retinal signal data as described herein may be applicable to the analysis of features specific to any conditions that are expressed in retinal signal data.

The systems and methods described herein may comprise predicting whether a patient is subject to a condition by: 1) collecting retinal signal data of the patient, 2) receiving a selection of conditions to examine, 3) retrieving mathematical models corresponding to the selected conditions 4) extracting retinal signal features from the retinal signal data, 5) extracting descriptors from the retinal signal features, where the descriptors are relevant to the biosignatures of the selected conditions within the retinal signal data, 6) applying the descriptors to the mathematical models, and/or 7) outputting predicted probabilities that the patient is subject to each condition. Clinical information of the patient may be collected. Clinical information cofactors may be generated using the clinical information. The clinical information cofactors may also be applied to the mathematical models.

The systems and methods described herein may be based on retinal signal data having a higher level of information compared to data captured by conventional ERG. The collected retinal signal data may be analyzed using mathematical and statistical calculations to extract specific retinal signal features. The retinal signal features may comprise parameters of the retinal signal data and/or features generated using the retinal signal data. Descriptors may be extracted from the retinal signal features. Graphical representations of the findings may be developed and output, and may provide visual support for choices made in selecting relevant retinal signal features and/or descriptors. Applications may apply mathematical and/or statistical analysis of the results, allowing the quantification of those retinal signal features and/or descriptors, and comparisons between various conditions. Based upon the retinal signal data and/or any other clinical information, classifiers may be constructed which describe a biosignature of a condition identified in the retinal signal data. The retinal signal data of a patient may be collected, and a distance between the patient's retinal signal data and the identified biosignatures may be determined, such as by using the classifiers.

Computing Environment

FIG. 1 illustrates a computing environment 100, which may be used to implement and/or execute any of the methods described herein. In some embodiments, the computing environment 100 may be implemented by any of a conventional personal computer, a network device and/or an electronic device (such as, but not limited to, a mobile device, a tablet device, a server, a controller unit, a control device, etc.), and/or any combination thereof appropriate to the relevant task at hand. In some embodiments, the computing environment 100 comprises various hardware components including one or more single or multi-core processors collectively represented by processor 110, a solid-state drive 120, a random access memory 130, and an input/output interface 150. The computing environment 100 may be a computer specifically designed to operate a machine learning algorithm (MLA). The computing environment 100 may be a generic computer system.

In some embodiments, the computing environment 100 may also be a subsystem of one of the above-listed systems. In some other embodiments, the computing environment 100 may be an "off-the-shelf" generic computer system. In some embodiments, the computing environment 100 may also be distributed amongst multiple systems. The computing environment 100 may also be specifically dedicated to the implementation of the present technology. As a person in the art of the present technology may appreciate, multiple variations as to how the computing environment 100 is implemented may be envisioned without departing from the scope of the present technology.

Those skilled in the art will appreciate that processor 110 is generally representative of a processing capability. In some embodiments, in place of or in addition to one or more conventional Central Processing Units (CPUs), one or more specialized processing cores may be provided. For example, one or more Graphic Processing Units 111 (GPUs), Tensor Processing Units (TPUs), and/or other so-called accelerated processors (or processing accelerators) may be provided in addition to or in place of one or more CPUs.

System memory will typically include random access memory 130, but is more generally intended to encompass any type of non-transitory system memory such as static random access memory (SRAM), dynamic random access memory (DRAM), synchronous DRAM (SDRAM), read-only memory (ROM), or a combination thereof. Solid-state drive 120 is shown as an example of a mass storage device, but more generally such mass storage may comprise any type of non-transitory storage device configured to store data, programs, and other information, and to make the data, programs, and other information accessible via a system bus 160. For example, mass storage may comprise one or more of a solid state drive, hard disk drive, a magnetic disk drive, and/or an optical disk drive.

Communication between the various components of the computing environment 100 may be enabled by a system bus 160 comprising one or more internal and/or external buses (e.g., a PCI bus, universal serial bus, IEEE 1394 "Firewire" bus, SCSI bus, Serial-ATA bus, ARINC bus, etc.), to which the various hardware components are electronically coupled.

The input/output interface 150 may allow enabling networking capabilities such as wired or wireless access. As an example, the input/output interface 150 may comprise a networking interface such as, but not limited to, a network port, a network socket, a network interface controller and the like. Multiple examples of how the networking interface may be implemented will become apparent to the person skilled in the art of the present technology. For example the networking interface may implement specific physical layer and data link layer standards such as Ethernet, Fibre Channel, Wi-Fi, Token Ring or Serial communication protocols. The specific physical layer and the data link layer may provide a base for a full network protocol stack, allowing communication among small groups of computers on the same local area network (LAN) and large-scale network communications through routable protocols, such as Internet Protocol (IP).

The input/output interface 150 may be coupled to a touchscreen 190 and/or to the one or more internal and/or external buses 160. The touchscreen 190 may be part of the display. In some embodiments, the touchscreen 190 is the display. The touchscreen 190 may equally be referred to as a screen 190. In the embodiments illustrated in FIG. 1, the touchscreen 190 comprises touch hardware 194 (e.g., pressure-sensitive cells embedded in a layer of a display allowing detection of a physical interaction between a user and the display) and a touch input/output controller 192 allowing communication with the display interface 140 and/or the one or more internal and/or external buses 160. In some embodiments, the input/output interface 150 may be connected to a keyboard (not shown), a mouse (not shown) or a trackpad (not shown) allowing the user to interact with the computing device 100 in addition to or instead of the touchscreen 190.

According to some implementations of the present technology, the solid-state drive 120 stores program instructions suitable for being loaded into the random access memory 130 and executed by the processor 110 for executing acts of one or more methods described herein. For example, at least some of the program instructions may be part of a library or an application.

Retinal Signal Processing System

Figure 2:
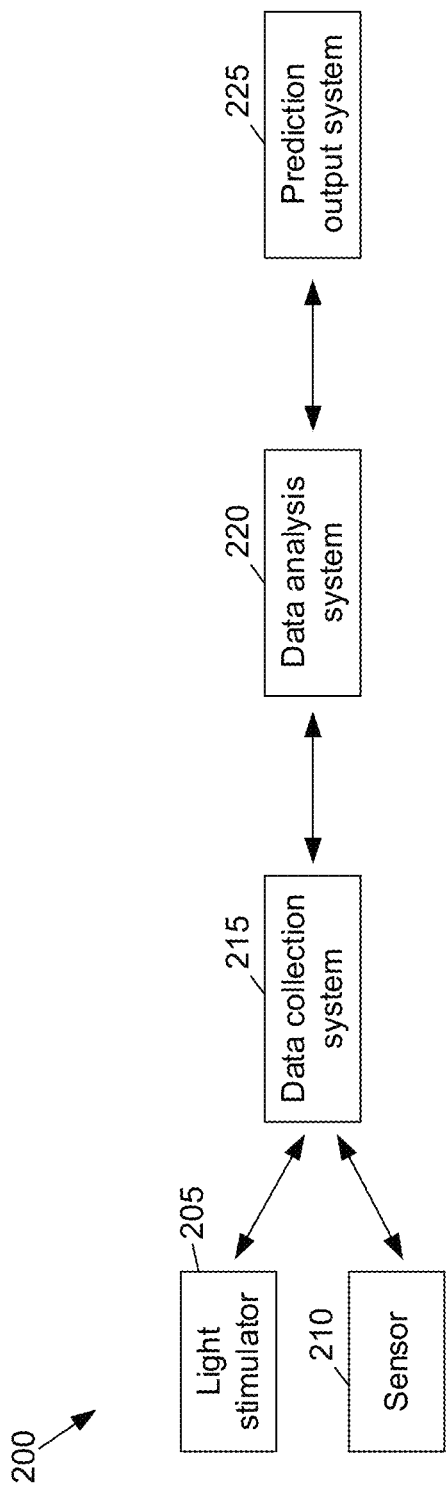
FIG. 2 is a block diagram of a retinal signal processing system in accordance with various embodiments of the present technology.

FIG. 2 is a block diagram of a retinal signal processing system 200 in accordance with various embodiments of the present technology. The retinal signal processing system 200 may collect retinal signal data from a patient. As described above, when compared with conventional ERG, the retinal signal data captured using the retinal signal processing system 200 may comprise additional features and/or data, such as impedance, a higher measurement frequency, an extended range of retinal light stimulation, and/or a longer measurement time. The retinal signal processing system 200 may process and/or analyse the collected data. The retinal signal processing system 200 may output a predicted likelihood that a patient is subject to a given condition such as a medical condition.

It is to be expressly understood that the system 200 as depicted is merely an illustrative implementation of the present technology. Thus, the description thereof that follows is intended to be only a description of illustrative examples of the present technology. This description is not intended to define the scope or set forth the bounds of the present technology. In some cases, what are believed to be helpful examples of modifications to the system 200 may also be set forth below. This is done merely as an aid to understanding, and, again, not to define the scope or set forth the bounds of the present technology. These modifications are not an exhaustive list, and, as a person skilled in the art would understand, other modifications are likely possible. Further, where this has not been done (i.e., where no examples of modifications have been set forth), it should not be interpreted that no modifications are possible and/or that what is described is the sole manner of implementing that element of the present technology. As a person skilled in the art would understand, this is likely not the case. In addition, it is to be understood that the system 200 may provide in certain instances simple implementations of the present technology, and that where such is the case they have been presented in this manner as an aid to understanding. As persons skilled in the art would understand, various implementations of the present technology may be of a greater complexity.

The retinal signal processing system 200 may comprise a light stimulator 205, which may be an optical stimulator, for providing light stimulation signals to the retina of a patient. The retinal signal processing system 200 may comprise a sensor 210 for collecting electrical signals that occur in response to the optical stimulation. The retinal signal processing system 200 may comprise a data collection system 215, which may be a computing environment 100, for controlling the light stimulator 205 and/or collecting data measured by the sensor 210. For example the light stimulator 205 and/or sensor 210 may be a commercially available ERG system such as the Espion Visual Electrophysiology System from DIAGNOSYS, LLC or the UTAS and RETEVAL systems manufactured by LKC TECHNOLOGIES, INC.

The light stimulator 205 may be any kind of light source or sources which, alone or in combination, can generate light within a specified range of wavelength, intensity, frequency and/or duration. The light stimulator 205 may direct the generated light onto the retina of the patient. The light stimulator 205 may comprise light-emitting diodes (LEDs) in combination with other light sources, such as one or more Xenon lamps. The light stimulator 205 may provide a background light source.

The light stimulator 205 may be configured to provide a light stimulation signal to the retina of the patient. The retinal signal data collected may depend upon the light stimulation conditions. In order to maximise the potential to generate relevant retinal signal features in the retinal signal data, the light stimulator 205 may be configured to provide a large variety of light conditions. The light stimulator 205 may be configurable to control the background light and/or the stimulation light directed onto the retina as light flashes.

The light stimulator may comprise any sources of light able to generate light beams of different wavelength (e.g. from about 300 to about 800 nanometers), light intensity (e.g. from about 0.001 to about 3000 $cd \cdot s/m^2$), illumination time (e.g. from about 1 to about 500 milliseconds), time between each light flashes (e.g. about 0.2 to about 50 seconds) with different background wavelength (e.g. from about 300 to about 800 nanometers) and background luminance (e.g. about 0.01 to about 900 $cd/m^2$).

The retinal signal processing system 200 may comprise a sensor 210. The sensor 210 may be arranged to detect electrical signals from the retina. The sensor 210 may comprise one or more electrodes. The sensor 210 may be an electroretinography sensor. A grounding electrode may be placed on the skin in the middle of the forehead. Reference electrodes for each eye may be placed on the earlobes or temporal areas near the eyes, or other skin areas.

Electrical signals from the retina may be triggered by light stimulation from the light stimulator 205 and collected by the sensor 210 as retinal signal data. The retinal signal data may be collected by a sensor 210 such as by an electrode positioned on the ocular globe or nearby ocular areas. The light may trigger an electrical signal of low amplitude generated by the retinal cells of the patient. Depending upon the nature of the light (e.g. intensity, wavelength, spectrum, frequency and duration of the flashes) and the conditions for the light stimulation (e.g. background light, dark or light adaptation of the individual subjected to this process), different electrical signals may be generated because different types of retinal cells will be triggered. This signal propagates within the eye and ultimately to the brain visual areas via the optic nerve. However, as any electrical signal, it propagates in all possible directions depending upon the conductivity of the tissues. Therefore the electrical signal may be collected in the tissues external to the ocular globe, accessible from outside, such as the conjunctiva.

There are several types of electrodes which can be used to collect the electrical signal. They are based upon specific wire conductivity and geometry. It should be understood that there are many possible designs of recording electrodes and that any suitable design or combination of designs may be used for the sensor 210. The sensor 210 may comprise contact lens, gold foil, gold wire, corneal wick, wire loops, microfibers, and/or skin electrodes. Each electrode type has its own recording characteristics and inherent artefacts.

In addition to the sensor 210, the system 200 may also include other devices to monitor eye position and/or pupil size, both having an impact on the quantity of light reaching the retina and therefore affecting the electrical signal triggered in response to this stimulus. The system 200 may include sensors to record light wavelength, light spectrum and/or light intensity, such as a spectrometer and/or photodetector.

The electrical signal may be obtained between the active ocular electrode (positioned onto the eye) and the reference electrode, with differential recording from the ground electrode. The electrodes of the sensor 210 may be connected to a data collection system 215, which may comprise a recording device. The data collection system 215 may allow for amplification of the electrical signals and/or conversion of the electrical signals to digital signals for further processing. The data collection system 215 may implement frequency filtering processes that may be applied to the electrical signals from the sensor 210. The data collection system 215 may store the electrical signals in a database in the format of voltage versus time points.

The data collection system 215 may be arranged to receive measured electrical signals of a patient, such as from the sensor 210, and/or stimulating light data, such as from the light stimulator 205, and store this collected data as retinal signal data. The data collection system 215 may be operatively coupled to the light stimulator 205 which may be arranged to trigger the electrical signals and provide the data to the data collection system 215. The data collection system 215 may synchronise the light stimulation with the electrical signal capture and recording.

The collected data may be provided to the data collection system 215 via any suitable method, such as via a storage device (not shown) and/or a network. The data collection system 215 may be connectable to the sensor 210 and/or the light stimulator 205 via a communication network (not depicted). The communication network may be the Internet and/or an Intranet. Multiple embodiments of the communication network may be envisioned and will become apparent to the person skilled in the art of the present technology.

The retinal signal data may comprise electrical response data (e.g. voltage and circuit impedance) collected for several signal collection times (e.g. 5 to 500 milliseconds) at several sampling frequencies (e.g. 0.2 to 24 kHz) with the light stimulation synchronization time (time of flash) and/or offset (baseline voltage and impedance prior to light stimulation). The data collection system 215 may collect retinal signal data at frequencies (i.e. sampling rate) of 4 to 16 kHz, or higher. This frequency may be higher than conventional ERG. The electrical response data may be collected continuously or intermittently.

The data collection system 215 may comprise a sensor processor for measuring the impedance of the electrical circuit used to collect the retinal signal data. The impedance of the electrical circuit may be recorded simultaneously with the capture of other electrical signals. The collected impedance data may be stored in the retinal signal data. The method to determine the impedance of the circuit simultaneously with the capture of the electrical signals may be based upon a process of injecting a reference signal of known frequency and amplitude through the recording channel of the electrical signals. This reference signal may then be filtered out separately and processed. By measuring the magnitude of the output at the excitation signal frequency, the electrode impedance may be calculated. Impedance may then be used as a co-variable to enhance signal density with the resistance of the circuit at each time point of the recording of the electrical signals.

The data analysis system 220 may process the data collected by the data collection system 215. The data analysis system 220 may extract retinal signal features and/or descriptors from the retinal signal data, and/or perform any other processing on the retinal signal data. The data analysis system 220 may receive clinical information of a patient and/or extract clinical information cofactors from the clinical information.

The prediction output system 225 may receive data from the data analysis system 220 and generate an output to be used by a clinician. The output may be an output user interface, a report or other document, etc. The output may indicate a predicted likelihood that a patient is subject to one or more conditions. For each condition, the output may indicate the predicted likelihood that the patient is subject to that condition. The output may indicate a patient positioning within a pathology. The output may be used by a clinician to aid in determining whether a patient is subject to a medical condition and/or determining which medical condition the patient is subject to.

The data collection system 215, data analysis system 220, and/or prediction output system 225 may be accessed by one or more users, such as through their respective clinics and/or through a server (not depicted). The data collection system 215, data analysis system 220, and/or prediction output system 225 may also be connected to appointment management software which could schedule appointments or follow-ups based on the determination of the condition by embodiments of the system 200.

The data collection system 215, data analysis system 220, and/or prediction output system 225 may be distributed amongst multiple systems and/or combined within a system or multiple systems. The data collection system 215, data analysis system 220, and/or prediction output system 225 may be geographically distributed.

The systems and methods described herein may comprise: 1) retrieving retinal signal data collected from multiple individuals, such as from a memory of a computer system, 2) extracting and/or generating retinal signal features from the retinal signal data, such as voltage, circuit impedance, signal collection times, sampling frequencies, light stimulation synchronisation time and/or offset, and/or any other types of data that can be extracted from the retinal signal data or generated using the retinal signal data, 3) combining the retinal signal features with cofactors from clinical information relevant to conditions observed in the respective individual, 4) selecting retinal signal features from the extracted features and combined features and determining a hierarchy with ranking depending upon the relevance of the retinal signal features, 5) assembling this information into mathematical descriptors, 6) estimating classifiers from those mathematical descriptors, 7) building mathematical domains of classifiers relevant to those conditions, and/or 8) obtaining density functions from those classifiers.

The mathematical descriptors may be mathematical functions combining features from the retinal signal data and/or clinical cofactors. The descriptors may indicate a retinal signal feature specific to a condition or a population in view of further discrimination between groups of patients. Examples of descriptors that may be used include skewness, kurtosis, compactness, eigenvectors, centroid coordinates, local binary patterns, time-series regression coefficients, spectral entropy, any form of quantum entropy, Rényi entropy, von Neumann entropy, Hartley entropy, Tsallis entropy, Unified entropy, Hu moments, Haralick's features, and/or eigenvalues-based functions. The descriptors may be used to obtain classifiers. The classifiers may be mathematical or statistical functions that use descriptors to map data to a category or a class of information by ranking the descriptors according to their statistical significance. The descriptors may be ranked based on their relevance for depicting specific components of a biosignature. The descriptors may be grouped into a catalogue of descriptors. The catalogue of descriptors may be used when training an MLA.

The systems and methods described herein may comprise: 1) retrieving retinal signal data collected from an individual, such as from a memory of a computer system, 2) extracting and/or generating retinal signal features from the retinal signal data, such as voltage, circuit impedance, signal collection times, sampling frequencies, light stimulation synchronisation time and/or offset, and/or any other types of data that can be extracted from the retinal signal data or generated using the retinal signal data, 3) combining the retinal signal features with cofactors from clinical information relevant to conditions observed in the individual, 4) calculating probabilities that the individual belongs to one or several domains (i.e. is subject to a condition), and/or 5) determining the mathematical proximity to those domains for this individual as a predicted probability that the patient is subject to the condition corresponding to the domain.

The clinical information may include information indicating general health conditions of the individual, such as information regarding concomitant diseases, treatments, prior medical conditions, coffee, alcohol or tobacco use, substance abuse, and/or any other general health condition data. The clinical information may include information related to specific psychiatric conditions, such as information from structured questionnaires specific to psychiatric illnesses. These structured questionnaires may include questions related to anxiety, affective and mood components, cognitive impairments, feelings, habits, hallucinations, behaviors, and/or other questions relevant to psychiatric illnesses. Clinical information cofactors may be extracted from the clinical information, such as clinical information cofactors indicating age, gender, iris color, and/or skin pigmentation as a proxy for retinal pigmentation, etc.

The retinal signal data may comprise several biosignatures, where each biosignature is specific to a condition. The biosignature corresponding to a condition for a given patient may be identified using the classifiers. The condition may be a psychiatric condition such as but not limited to bipolar disorder, schizophrenia and depression. The condition may also be neurological conditions, non-psychiatric conditions, or being at risk for such conditions. The steps for analysing retinal signal data as described herein may be applicable to the analysis of retinal signal features specific to any conditions that are expressed in retinal signal data.

Graphical representations of the findings may be developed and output, and may provide visual support for choices made in selecting retinal signal features to be used in the mathematical models. Applications may apply mathematical and/or statistical analysis of the results to assess for data suitability, robustness of information and accuracy of the results generated during the analysis process.

The retinal signal features extracted from the recorded retinal signal data may comprise electrical parameters such as voltage and circuit impedance, signal collection times (e.g. 5 to 500 milliseconds), sampling frequencies (e.g. 0.2 to 24 kHz), light stimulation synchronisation time (time of flash) and offset (baseline voltage and impedance prior to light stimulation), retinal areas illuminated, and/or other retinal signal features impacting on the retinal signal data. Retinal signal features may be generated based on extracted retinal signal features, such as by performing a mathematical operation on one or more of the extracted retinal signal features. The retinal signal features extracted from the retinal signal data may include data related to the retinal signal such as eye position, pupil size, distance from light source to the eye or part of the eye (pupil, retina) and/or applied luminance parameters (intensity, wavelength, spectrum, frequency of light stimulation, frequency of retinal signal sampling, wavelength, illumination time, background wavelength, background luminance). The retinal signal features may be voltage-independent and/or time-independent. All or a portion of these features may be analysed using the systems and methods described herein.

Retinal Signal Data Processing Methods

Figure 3:
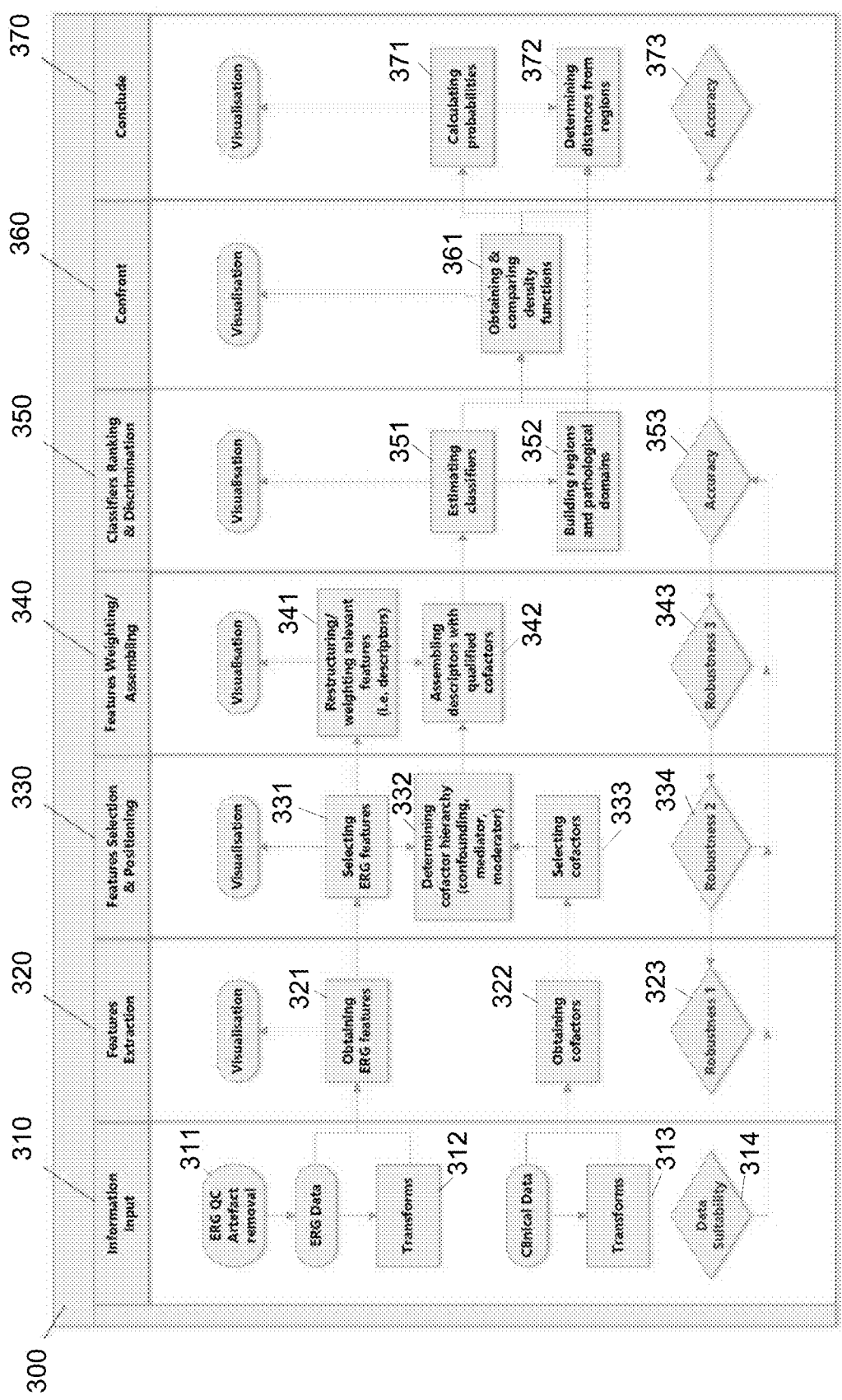
FIG. 3 illustrates an exemplary functional architecture of an information processing method leading to the construction of mathematical functions for predicting whether a patient is subject to a condition in accordance with various embodiments of the present technology.

FIG. 3 illustrates an exemplary functional architecture of an information processing method 300 leading to the construction of mathematical functions for predicting whether a patient is subject to a condition. The method 300 may be used for modeling of mathematical domains of information from retinal signal data collected from patients subject to conditions. All or portions of the method 300 may be executed during an information input stage 310, features extraction stage 320, features selection and positioning stage 330, features weighting and assembling stage 340, classifiers ranking and discrimination stage 350, confront stage 360 and/or a prediction output stage 370.

The retinal signal data and collected clinical information may be processed differently depending upon the level and specificity of information. Retinal signal features may be classes or categories of indicators given by explanatory variables towards attributes. Descriptors may be relevant features specific to a condition or a population that are determined following a discrimination process. Classifiers may be mathematical or statistical functions that use descriptors to map data to a category or a class following a ranking process. Regions may be identified as a subset of ranges of mathematical functions or collection of functions built with classifiers. A domain may be identified as a region specific to a condition.

It is to be expressly understood that the functional architecture as depicted in FIG. 3 is merely an illustrative implementation of the present technology. Thus, the description thereof that follows is intended to be only a description of illustrative examples of the present technology. This description is not intended to define the scope or set forth the bounds of the present technology.

In some cases, what are believed to be helpful examples of modifications to the functional architecture depicted in FIG. 3 may also be set forth below. This is done merely as an aid to understanding, and, again, not to define the scope or set forth the bounds of the present technology. These modifications are not an exhaustive list, and, as a person skilled in the art would understand, other modifications are likely possible. Further, where this has not been done (i.e., where no examples of modifications have been set forth), it should not be interpreted that no modifications are possible and/or that what is described is the sole manner of implementing that element of the present technology. As a person skilled in the art would understand, this is likely not the case. In addition, it is to be understood that the functional architecture depicted in FIG. 3 may provide, in certain instances, simple implementations of the present technology, and that where such is the case they have been presented in this manner as an aid to understanding. As persons skilled in the art would understand, various implementations of the present technology may be of a greater complexity.

In one or more aspects, the method 300 or one or more steps thereof may be performed by a computing system, such as the computing environment 100. The method 300 or one or more steps thereof may be embodied in computer-executable instructions that are stored in a computer-readable medium, such as a non-transitory mass storage device, loaded into memory and executed by a CPU. The method 300 is exemplary, and it should be understood that some steps or portions of steps in the diagram may be omitted and/or changed in order.

In certain embodiments, the potential for a specific mathematical modelling of a condition is supported by the graphical representation of domains of information specific to the conditions that have been considered during demonstrations and subsequently used to describe the concept of mathematical domains. Results of robustness and accuracy analyses are used to demonstrate the relevance and specificity of the mathematical domains built with the present technology.

By enlarging the analysis strategy to additional calculation processes, then generating additional mathematical descriptors, methods for deciphering a biosignature included in retinal signal data may be enriched.

Information Input

At step 311, information input may be performed using collected retinal signal data with or without removal of artifacts that may include distorted signals, interferences, and/or any other type of artifacts. The artifacts may occur through one or more of: electrical signals not originating from the retina being captured inadvertently, shifts in the ocular electrode positioning, changes in the ground or reference electrode contact, eye lid blinks, and/or ocular movements.

At step 312, the collected retinal signal data may be transformed, such as by transposing retinal signal data into another mono-dimensional or multi-dimensional scale, e.g. scaling, shifting, elementary functions transformation (e.g. log, polynomial, power, trigonometric), time-series (leading to change in distribution shape), wavelet transforms (leading to scalograms), empirical mode decomposition (leading to Intrinsic Mode Functions (IMFs)), gradient transforms (leading to a vector), and/or kernel decomposition (leading to change in distribution shape and/or length scales and signal variances). Filtration (Finite Impulse Response, Infinite Impulse Response) may be performed on the retinal signal data such as High-Pass Filter, Low-Pass Filter, Band-Pass Filter, Notch Filters. Hilbert-Huang Transform (instantaneous Frequency of IMFs).

At step 313, clinical information may be transformed, such as by transposing clinical data into another mono-dimensional or multidimensional scale, e.g. scaling, shifting, elementary functions transformation (e.g. log, polynomial, power, trigonometric), and/or regrouping variables in composite variables.

At step 314, data suitability of data generated during the information input stage 310 may be tested and confirmed, such as by ensuring all data to be processed will fulfill a standardised format suitable for the intended processing.

Features Extraction

At step 321, retinal signal features which are deemed to contain components of a biosignature may be obtained by e.g. time-frequency analysis (magnitude of specific location in the scalograms, positions of magnitude minima and maxima), kernel decomposition, Principal Component Analysis (PCA), geometric (algebraic) operations in various time-frequency intervals such as min (e.g. a-wave), max (e.g. b-wave), latency, slope, gradient, curvature, integral, energy (sum of squared amplitudes), variance, cohesion-dispersion (homogeneity, density), and/or any other methods for retrieving or generating retinal signal features from the retinal signal data.

At step 322, the potential clinical information cofactors which are deemed to influence upon the components of a biosignature may be obtained from the clinical information, by e.g. Multiple Component Analysis (Chi square combined with variances) and subsequent grouping, forward selection based on a stepwise regression, Best Subset Regression (using a specified set of cofactors), from clinical practice (i.e. cofactors to the condition, e.g. duration of disease, number of crisis/hospitalisations), and/or any other methods for obtaining clinical information cofactors from the clinical information.

At step 323, the robustness of information and accuracy of the results generated during the features extraction stage 320 may be assessed.

Features Selection and Positioning

At step 331, the retinal signal features which contain the most significant components of a biosignature may be selected by e.g. time-frequency visual analyses or scalograms (in that case, retinal signal features are magnitudes of the signal at certain time-frequency windows which are found discriminant), stepwise regression with cross-validation, cofactor adjusted or unadjusted Sparse Representation based Classification (SRC) with predefined thresholds, selection and combination of most relevant retinal signal features to generate principal components in e.g. Supervised PCA (SPCA) process, least absolute shrinkage and selection operator (LASSO), ridge regression, elastic net, Bayesian or spike-and-slab methods, and/or any other selection method.

At step 332, cofactor hierarchy (confounding, mediator, moderator) may be determined, i.e. assessing the direction of the influence and the hierarchy of the most important retinal signal features and clinical information cofactors, as components of a biosignature, which together have a high contribution to the analysis models, by e.g. i) confounding methods (randomization, restriction and matching); stratification followed by the Mantel-Haenszel estimator; and/or multivariate methods e.g. ANCOVA, linear and logistic regressions, and/or ii) mediation and moderation methods. e.g. Baron & Kenny method; Fairchild & MacKinnon method, and/or other suitable methods.

At step 333, clinical information cofactors with high contribution to the mathematical models may be selected from the clinical information, i.e. those clinical information cofactors which influence upon the components of a biosignature and together have a high contribution to the mathematical models (thus becoming 'qualified' cofactors).

At step 334, the robustness of information and accuracy of the results generated during the features selection and positioning stage 330 may be assessed.

Features Weighting and Assembling

At step 341, restructuring and/or weighting relevant retinal signal features may be performed to generate descriptors. For example the contribution of retinal signal features may be determined and/or mapped. Retinal signal features which contain the descriptors of a biosignature and have an influence on the models may be identified, by e.g. multivariate regression analyses or related processes.

At step 342, descriptors may be assembled with the most significant clinical information cofactors (i.e. qualified cofactors). The descriptors may then be selected to obtain the components of a biosignature which together contributes the most to the mathematical models, by e.g. match-merging descriptors and cofactors using mathematical expressions or relations, by using e.g. PCA, SPCA or other methods used in selecting and/or combining retinal signal data features.

At step 343, the robustness of information and accuracy of the results generated during the features weighting and assembling stage 340 may be assessed.

Classifiers Ranking and Discrimination

At step 351, classifiers may be estimated by using assembled descriptors and/or clinical information cofactors to train classifiers. The classifiers may be selected and/or ranked based upon their performances by e.g. logistic regressions, probit regressions, probabilistic modelling (Gaussian process, kernel estimating models, Bayesian modelling), Best Subset Regression (using a specified set of predictors), SVM, neuronal network methods, decision tree, random forest, weighted-voting, boosting and bagging, Kaplan-Meier analysis, Cox regression, and/or other selection or ranking methods.

At step 352, regions and domains may be built by selecting and mapping classifiers specific to conditions into mathematical functions which represent their most specific biosignature, by e.g. visualization of the regression results enhanced by mathematical constructs (e.g. wavelets, Kullback-Leibler divergence, etc.), Neyman-Pearson to discriminate between domains, and/or other related methods.

At step 353, the robustness of information and accuracy of the results generated during the classifiers ranking and discrimination stage 350 may be assessed.

Confront Findings from Retinal Signal Deciphering

At step 361, density functions may be obtained and compared, i.e. by obtaining mathematical functions which contain the highest density of biosignature components from retinal signal data and clinical cofactors, and comparing those functions across conditions by e.g. histogram; kernel density estimation (e.g., Parzen-Rosenblatt windows, bandwidth selection), characteristic function density and other relevant estimators, data clustering techniques, including vector quantization, reconstruction methods, either based on the sample cumulative probability distribution or on the sample moments, and/or other methods.

Conclude the Retinal Signal Deciphering

At step 371, probabilities may be calculated from the mathematical functions which contain the relevant density of biosignature components from retinal signal data and clinical information cofactors in comparing those obtained in various conditions, by e.g. using the density function; estimating the CPF (cumulative probability function) and/or other related methods.

At step 372, distances from regions may be determined by identifying biosignature components, most relevant to the distances between regions or domains of high density of information, in various conditions, and calculating the distances as mathematical expressions, by e.g. comparing probabilities with the Bayesian statistical priors. Entropy-based methods, Kullback-Leibler divergence parameter to assess direction of changes, and Neyman-Pearson to assess distances between regions. Semiparametric maximum likelihood estimation procedure pool-adjacent-violation-algorithm (PAVA) may be used as well as other methods challenging the medical condition attributed to each individual part of a model (i.e. regions) and reassessing their belonging to that model using IPWE (Inverse Probability Weighting Estimator) or related methods.

At step 373, the robustness of information and accuracy of the results generated during the conclude stage 370 may be assessed.

Prediction Methods

Figure 4:
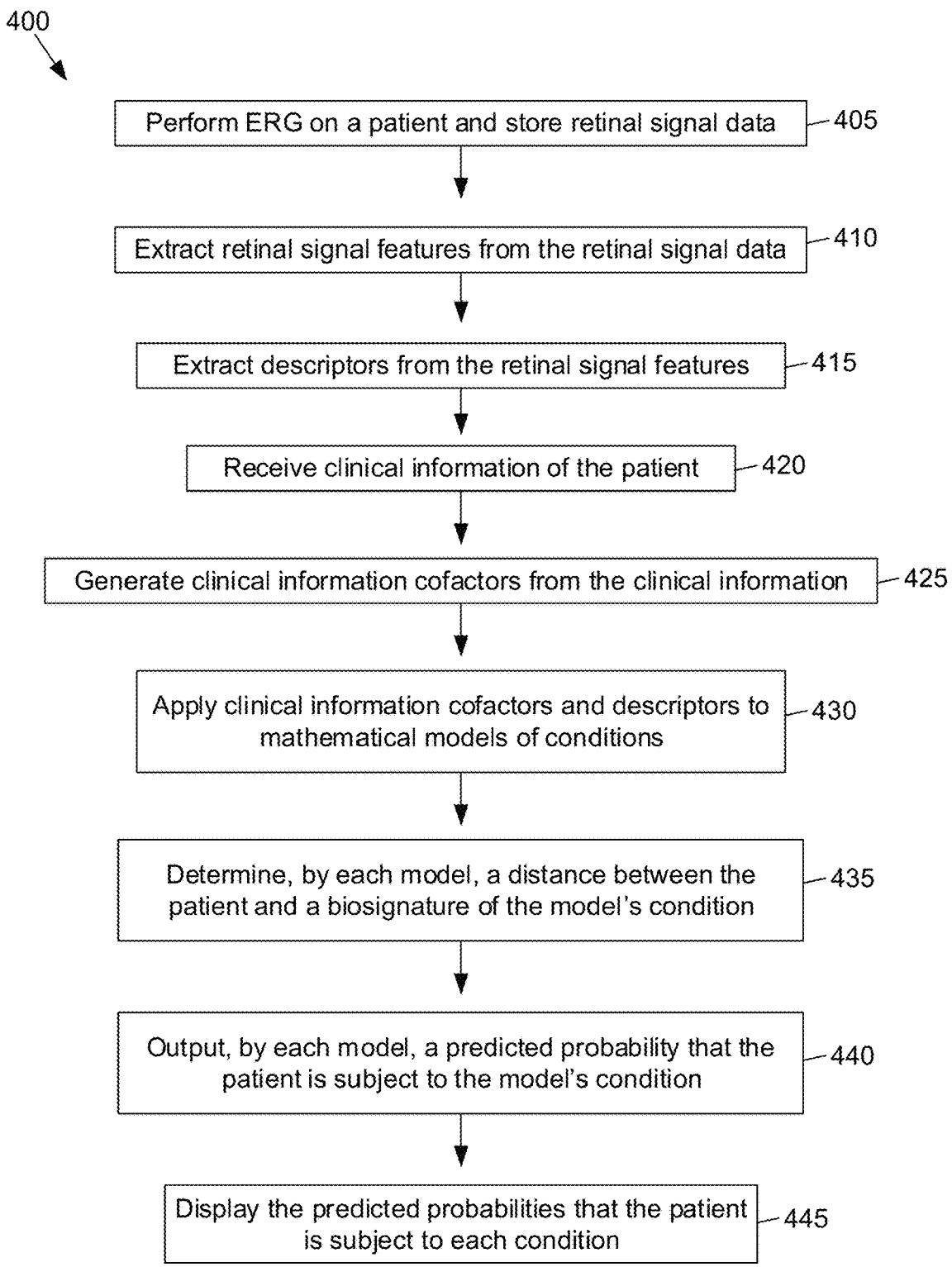
FIG. 4 illustrates a flow diagram of a method for predicting a likelihood of a medical condition in accordance with various embodiments of the present technology.

FIG. 4 illustrates a flow diagram of a method 400 for predicting a likelihood that a patient is subject to a condition in accordance with various embodiments of the present technology. All or portions of the method 400 may be executed by the data collection system 215, data analysis system 220, and/or the prediction output system 225. In one or more aspects, the method 400 or one or more steps thereof may be performed by a computing system, such as the computing environment 100. The method 400 or one or more steps thereof may be embodied in computer-executable instructions that are stored in a computer-readable medium, such as a non-transitory mass storage device, loaded into memory and executed by a CPU. The method 400 is exemplary, and it should be understood that some steps or portions of steps in the flow diagram may be omitted and/or changed in order.

The method 400 comprises performing various activities such as extracting retinal signal features from retinal signal data, selecting the most relevant retinal signal features to specific conditions, combining and comparing those retinal features to generate mathematical descriptors most discriminant to the conditions to be analysed or compared, generating multimodal mapping, identifying biomarkers and/or biosignatures of the conditions, and/or predicting a likelihood that a patient us subject to any one of the conditions, as will now be described in further detail below.

At step 405 retinal signal data may be captured from a patient. The retinal signal data may be captured using a pre-defined collection protocol. The retinal signal data may include measured electrical signals captured by electrodes placed on the patient. The retinal signal data may include parameters of the system used to capture the retinal signal data, such as the parameters of light stimulation. The retinal signal data may include the impedance of the receiving electrical circuit used in the device measuring the electrical signals. In certain embodiments, this step 405 is omitted.

The retinal signal data may comprise impedance measurements and/or other electrical parameters. The retinal signal data may comprise optical parameters such as pupil size changes, and/or applied luminance parameters (intensity, wavelength, spectrum, frequency of light stimulation, frequency of retinal signal sampling).

To generate the retinal signal data, the retina of the patient may be stimulated, such as by using the light stimulator 205 which may be one or more optical stimulators. The retinal signal data may be collected by a sensor, such as the sensor 210, which may comprise one or more electrodes and/or other sensors.

The light stimulator may comprise any sources of light able to generate light beams of different wavelength (e.g. from about 300 to about 800 nanometers), light intensity (e.g. from about 0.01 to about 3000 cd·s/m$^2$), illumination time (e.g. from about 1 to about 500 milliseconds), time between each light flashes (e.g. about 0.2 to about 50 seconds) with different background wavelength (e.g. from about 300 to about 800 nanometers) and background luminance (e.g. about 0.1 to about 800 cd/m$^2$).

The retinal signal data may comprise electrical response data (e.g. voltage and circuit impedance) collected for several signal collection times (e.g. 5 to 500 milliseconds) at several sampling frequencies (e.g. 0.2 to 24 kHz) with the light stimulation synchronisation time (time of flash) and offset (baseline voltage and impedance prior to light stimulation). Therefore, step 405 may comprise collecting retinal signal data at frequencies of 4 to 16 kHz.

After the retinal signal data is collected, such as by a practitioner, the retinal signal data may be uploaded to a server, such as the data analysis system 220, for analysis. The retinal signal data may be stored in a memory 130 of the computer system.

At step 410, if step 405 is omitted, the retinal signal data may be retrieved from the memory. 130. Retinal signal features may be extracted from the retinal signal data. The extraction of retinal signal features may be based upon the processing of the retinal signal data and/or their transforms using multiple signal analysis methods, such as polynomial regressions, wavelet transforms, and/or empirical mode decomposition (EMD). The extraction of retinal signal features may be based upon parameters derived from those analyses or specific modeling, e.g. principal components and most discriminant predictors, parameters from linear or non-linear regression functions, frequency of higher magnitude, Kullback-Leibler coefficient of difference, features of the gaussian kernels, log likelihood of difference and/or areas of high energy. These analyses may be used to determine the contribution of each specific retinal signal feature and compare the retinal signal features statistically.

The retinal signal features to be extracted may have been previously determined. The retinal signal features to extract may have been determined by analyzing labeled datasets of retinal signal data for multiple patients. Each patient represented in the datasets may have one or more associated medical conditions that the patient is subject to and/or one or more medical conditions that the patient is not subject to. These medical conditions may be the label to each patient's dataset. By analyzing a set of retinal signal data from patients sharing a medical condition, the retinal signal features to extract may be determined. A multi-modal map may be generated based on the retinal signal features. Domains may be determined based on the multi-modal map.

At step 415 descriptors may be extracted from the retinal signal features. The mathematical descriptors may be mathematical functions combining features from the retinal signal data and/or clinical cofactors. The descriptors may indicate a retinal signal feature specific to a condition or a population in view of further discrimination between groups of patients. As described above at step 342 of the method 300, descriptors may be selected to obtain the components of a biosignature which together contributes the most to the mathematical models, by e.g. match-merging descriptors and cofactors using mathematical expressions or relations, by using e.g. PCA, SPCA or other methods used in selecting and/or combining retinal signal data features.

At step 420 clinical information of the patient may be received. The clinical information may include medical records and/or any other data collected regarding the patient. The clinical data may include the results of a questionnaire and/or clinical examination by a healthcare practitioner.

At step 425 clinical information cofactors may be generated using the clinical information. The clinical information cofactors may be selected based on their influence on the retinal signal data. The clinical information cofactors may include indications of the patient's age, gender, skin pigmentation which may be used as a proxy for retinal pigmentation, and/or any other clinical information corresponding to the patient.

At step 430 the clinical information cofactors and/or the descriptors may be applied to mathematical models of conditions. Any number of mathematical models may be used. A clinician may select which mathematical models to use. Each model may correspond to a specific condition or a control.

At step 435 each model may determine a distance between the patient and the biosignature of the model's condition. Main components of the retinal signal data may be located within domains corresponding to the conditions. The descriptors and/or clinical information cofactors may be compared to each model's biosignature.

At step 440 each model may output a predicted probability that the patient is subject to the model's condition. The likelihood that the patient is subject to a condition may be predicted based upon the level of statistical significance in comparing the magnitude and the location of the descriptors of the individual to those in the model. The predicted probability may be binary and indicate that the biosignature of the condition is either present or absent in the patient's retinal signal data. The predicted probability may be a percentage indicating how likely it is that the patient is subject to the condition.

At step 445 the predicted probability that the patient is subject to each condition may be output. An interface and/or report may be output. The interface may be output on a display. The interface and/or report may be output to a clinician. The output may indicate a likelihood that the patient is subject to one or more conditions. The output may indicate a patient positioning within a pathology. The predicted probabilities may be stored.

The output may include determining a medical condition, the predicted probability of a medical condition, and/or a degree to which retinal signal data of the patient is consistent with the condition and/or other conditions. The predicted probability may be in the format of a percentage of correspondence for the medical condition, which may provide an objective neurophysiological measure in order to further assist in a clinician's medical condition hypothesis.

The output may be used in conjunction with a clinician's provisional medical condition hypothesis to increase the level of comfort with the clinician's determination of a medical condition and/or start an earlier or more effective treatment plan. The output may be used to begin treatment earlier rather than spending additional time clarifying the medical condition and the treatment plan. The output may reduce the clinician's and/or patient's level of uncertainty of the clinician's provisional medical condition hypothesis. The output may be used to select a medication to administer to the patient. The selected medication may then be administered to the patient.

The method 400 may be used to monitor a condition of a patient. A patient may have been previously diagnosed with a condition. The method 400 may be used to monitor the progress of the condition. The method 400 may be used to monitor and/or alter a treatment plan for the condition. For example the method 400 may be used to monitor the effectiveness of a medication being used to treat the condition. The retinal signal data may be collected before, during, and/or after the patient is undergoing treatment for the condition.

The method 400 may be used to identify and/or monitor neurological symptoms of an infection, such as a viral infection. For example the method 400 may be used to identify and/or monitor neurological symptoms of patients who were infected with COVID-19. Retinal signal data may be collected from patients that are or were infected with COVID-19. The retinal signal data may be assessed using the method 400 to determine whether the patient is suffering from neurological symptoms, a severity of the neurological symptoms, and/or to develop a treatment plan for the neurological symptoms.

Generating Mathematical Models

Figure 5:
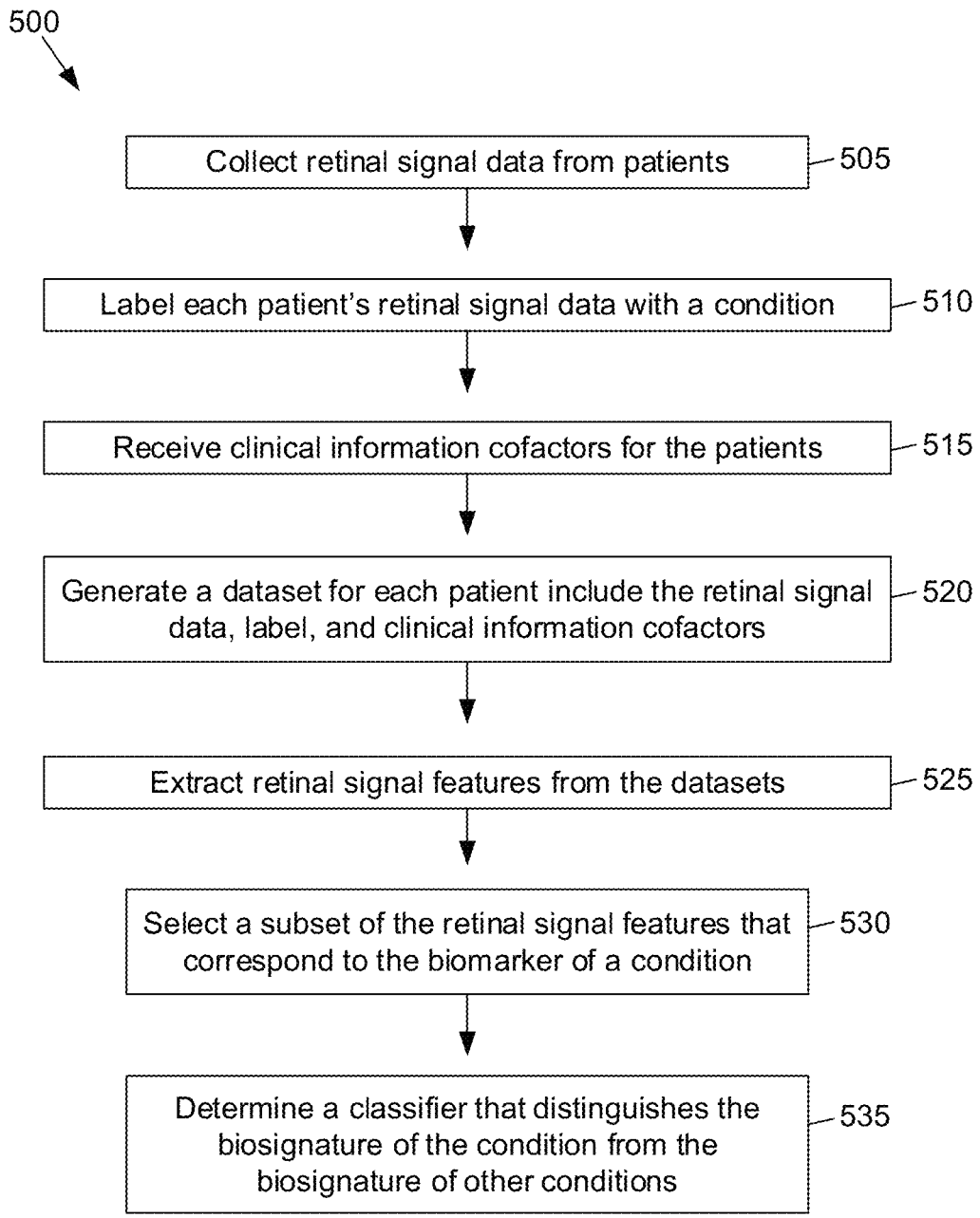
FIG. 5 illustrates a flow diagram of a method for generating a mathematical model for predicting whether a patient is subject to a condition in accordance with various embodiments of the present technology.

FIG. 5 illustrates a flow diagram of a method 500 for generating a mathematical model for predicting whether a patient is subject to a condition in accordance with various embodiments of the present technology. All or portions of the method 500 may be executed by the data collection system 215, data analysis system 220, and/or the prediction output system 225. In one or more aspects, the method 500 or one or more steps thereof may be performed by a computing system, such as the computing environment 100. The method 500 or one or more steps thereof may be embodied in computer-executable instructions that are stored in a computer-readable medium, such as a non-transitory mass storage device, loaded into memory and executed by a CPU. The method 500 is exemplary, and it should be understood that some steps or portions of steps in the flow diagram may be omitted and/or changed in order.

The method 500 may process datasets of retinal signal data and/or other clinical information to create a classification model based on domains specific to various conditions. Mathematical modeling of retinal signal data may be performed by using several sequential analyses that process retinal signal data and/or clinical information cofactors to generate classification metrics based upon domains that are specific to the conditions. The analysis has several mechanisms which combine retinal signal data and clinical information cofactors, such as specific descriptors in the retinal biosignatures, to select the most discriminant components as descriptors. These descriptors, which may be combined with clinical information cofactors, may be used to train classifiers and then select them based upon their performance in providing a probability factor for a patient to be subject to a condition. The descriptors may be used to build density functions specific to each of the conditions. Domain clusters may be formed using multimodal analysis of discriminant features, principal components, and mappings of descriptors of high statistical significance.

At step 505 retinal signal data may be collected from patients. The collected retinal signal data may comprise impedance measurements and/or other electrical parameters. The retinal signal data may comprise optical parameters such as distance from light source to the eye or part of the eye (pupil, retina), pupil size changes, and/or applied luminance parameters (light intensity, light wavelength, light spectrum, frequency of light stimulation, frequency of retinal signal sampling). In certain embodiments, the step 505 may be omitted.

At step 510 each patient's retinal signal data may be labelled with a condition. The label may be one or more conditions that the patient was diagnosed with. The label may indicate that the patient was not diagnosed with any conditions, in which case the patient may be referred to as a control subject. The condition may be schizophrenia, bipolar disorder, major depression disorder, psychosis, post-traumatic stress disorder, stroke, substance abuse, obsessive compulsive disorder, Alzheimer's, Parkinson's, multiple sclerosis, autism, attention deficit disorder, and/or any other condition. If the step 505 was omitted, step 510 may comprise retrieving stored retinal signal data from a memory, such as the memory 130 of the computing environment 100.

At step 515 clinical information cofactors for the patients may be received. The clinical information cofactors may be extracted from medical records. The clinical information cofactors may include indications of population parameters such as age, gender, and/or skin pigmentation as a proxy for retinal pigmentation, iris color, etc. Clinical information cofactors may be received for all or a subset of the patients for which retinal signal data was collected.

At step 520 a dataset may be generated for each patient. The dataset may include a patient's retinal signal data, the label or labels assigned to the patient, and/or the patient's clinical information cofactors. The dataset may be stored in a database and/or stored in any other suitable format.

At step 525 retinal signal features may be extracted from the retinal signal data in the datasets. Any suitable mathematical selection process may be used for selecting retinal features to extract, such as Principal Component Analysis (PCA), Generalized Linear Models (GLM), Sparse Representation based Classification (SRC), least absolute shrinkage and selection operator (LASSO) and/or a combination of several models aimed to transform the selected retinal signal features and generate descriptors of interest in terms of cohesion and density (information density) with the objective to select the most discriminant retinal signal features and generate mappings of statistical significance. Various methods may be used for analyzing the collected retinal signal data, such as, but not limited to, time-frequency analysis, prototype mother wavelets generated from reference datasets, probabilistic modelling, cohesion and dispersion of the information, principal components analysis (PCA), which may be supervised or unsupervised, generalized Linear Models (GLM), sparse representation based classification (SRC), least absolute shrinkage and selection operator (LASSO) and/or similar selection methods or a combination of several methods. The mappings may be used to delineate the areas of the retinal signal data (n-dimensions) which have the most discriminant power to separate the domain of each condition and position an individual within those domains (distances).

The biosignature of a condition may comprise parts of the retinal signal data that are unique to the condition. One or more of the most discriminant retinal signal features may be selected as descriptors of a certain condition. The descriptors may be combined in a multimodal calculation process.

The potential for a specific mathematical modelling is supported by the graphical representation of the domains of information specific to the conditions that have been considered during demonstrations and subsequently used to describe the domains. Clusters of relevant predictors may be defined among the retinal signal features obtained using multimodal analysis.

By enlarging the analysis strategy to additional calculation processes, then generating additional retinal signal features, those components used for deciphering a biosignature included in the retinal signal data may be enriched.

Frequency (Spectral) Analysis

Time-frequency analysis may be performed using mother wavelets for, e.g., discrete wavelet transforms (DWT) or continuous wavelet transforms (CWT), and/or empirical mode decomposition (EMD) filtering. The commonly used features may be visualised and/or calculated, such as frequency of higher magnitude, time of occurrence, frequency mapping (scalograms), time-frequency domains, wavelet coefficient as an output of the wavelet transform, relative occurrence frequency of wavelet coefficient, and/or composite parameters.

Specific mother wavelets (prototype wavelets) may be constructed and adjusted to the nature of the data (either control groups or group of individual with specific pathologies). Specific mother wavelets may be validated (wavelet design) with reprocessing and filtering frequencies which are not considered as significant features. This strategy may be used to adjust a known pre-defined mother wavelet and perform a more specific time-frequency analysis with or without time clustering (i.e. time-frequency analysis with mother wavelet adjusted depending upon the part of the retinal signal waveform being analysed).

Applications may be used to compare analyses and show the differences between retinal signal data from patients with conditions, such as psychiatric conditions, as compared to retinal signal data from individuals not diagnosed with those conditions (control subjects).

Principal Components Analysis

Principal component analysis (PCA) may be performed. The PCA may be supervised (SPCA) or not supervised (PCA) in order to extract the most discriminant retinal signal features from the retinal signal data. PCA may determine so-called "principal components" which may be retinal signal features with maximum dependence on the response variables, in this case the suspected conditions. PCA may analyse the dependency between retinal signal features and conditions and allow the selection of those retinal signal features with maximum dependency.

The retinal signal features may be analysed in combination with additional demographic or clinical variables, specific to the concomitant pathologies or medical conditions. Those analyses may lead to specific data vectors (principal component scores) used in defining retinal signal features which may then be combined and re-analysed ("confronted") in order to draw a classification of the most discriminant retinal signal features based upon their statistical significance with a pre-defined threshold. Such a classification may allow the selection of retinal signal features that can be used to build vectorized domains specific of conditions.

Probabilistic Modelling

Probabilistic modelling may be used to find areas of interest within the retinal signal data. Standard gaussian and/or non-gaussian process modelling may be used to define probability of events within the mass of information collected. The retinal signal features chosen to build the models (to train the model) may be selected based on the datasets specific to the retinal signal data from patients with specific conditions and control subjects (datasets of patients that are not subject to the conditions).

At step 530 a subset of the retinal signal features that correspond to the biomarker of a condition may be selected. The retinal signal features may be ranked based on their relevance to the condition. Some or all of the highest-ranked retinal signal features may be selected to be in the subset.

At step 535 a classifier may be determined that distinguishes the biosignature of the condition from the biosignature of other conditions. The classifier may include the subset of the retinal signal features and/or clinical information cofactors. The classifier may be a mathematical model indicative of the biosignature. In order to predict the likelihood that a patient is subject to a condition, the distance between the patient's retinal signal data and the classifier of the condition may be determined.

Figure 6:
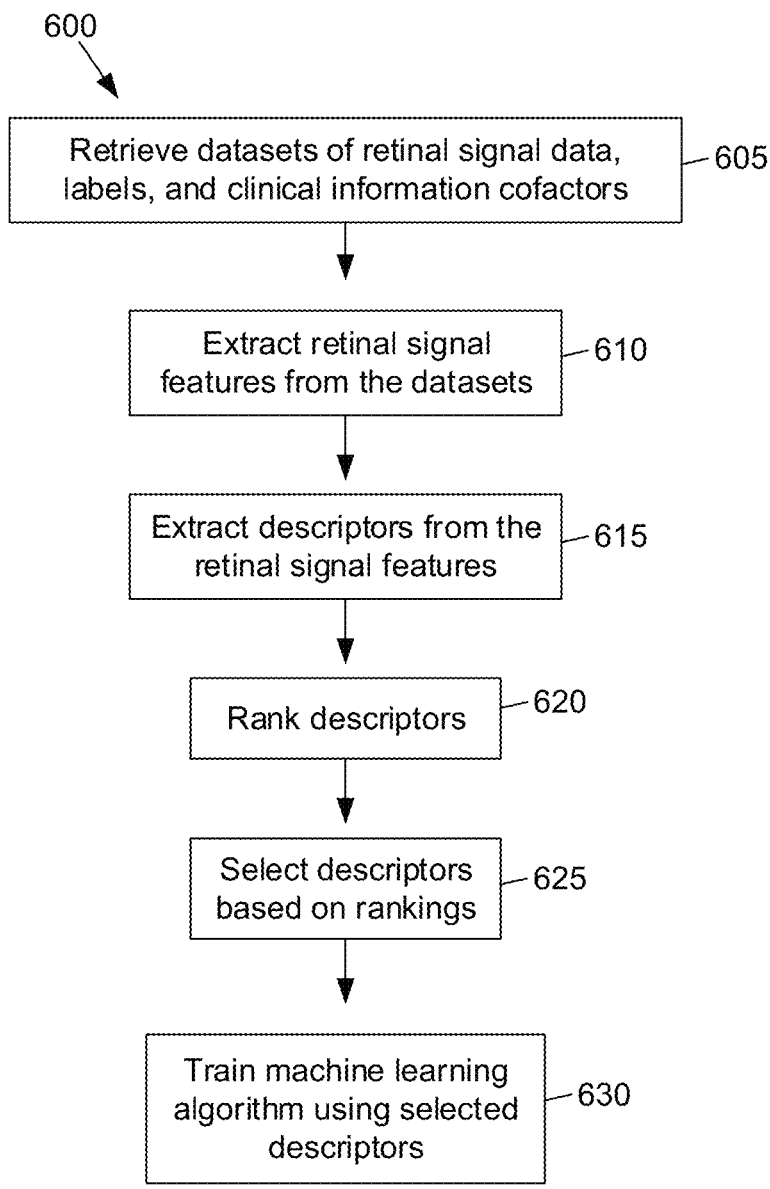
FIG. 6 illustrates a flow diagram of a method for training a machine learning algorithm (MLA) to predict a likelihood of a medical condition in accordance with various embodiments of the present technology.

FIG. 6 illustrates a flow diagram of a method 600 for training a machine learning algorithm (MLA) to predict a likelihood of a medical condition such as a psychiatric condition or a neurological condition in accordance with various embodiments of the present technology. All or portions of the method 600 may be executed by the data collection system 215, data analysis system 220, and/or the prediction output system 225. In one or more aspects, the method 600 or one or more steps thereof may be performed by a computing system, such as the computing environment 100. The method 600 or one or more steps thereof may be embodied in computer-executable instructions that are stored in a computer-readable medium, such as a non-transitory mass storage device, loaded into memory and executed by a CPU. The method 600 is exemplary, and it should be understood that some steps or portions of steps in the flow diagram may be omitted and/or changed in order.

At step 605 datasets of retinal signal data may be retrieved. The datasets may have been generated using steps 505-520 of the method 500, as described above. Each dataset may include a patient's retinal signal data, one or more labels corresponding to conditions that the patient has been diagnosed with, and clinical information cofactors corresponding to the patient. The retinal signal data may correspond to multiple patients. The retinal signal data may be selected based on a specific patient population. For example all retinal signal data corresponding to a specified gender and age range may be retrieved.

The retrieved datasets may comprise impedance measurements and/or other electrical parameters. The retrieved datasets may comprise optical parameters such as pupil size changes, and/or applied luminance parameters (light intensity, wavelength, spectrum, frequency of light stimulation, frequency of retinal signal sampling). The retrieved datasets may comprise population parameters such as age, gender, iris color, and/or skin pigmentation as a proxy for retinal pigmentation, etc.

The retinal signal data may be labeled. For each patient represented in the data, one or more conditions that the patient has been diagnosed with may be indicated. For patients that have not been diagnosed with any of the available conditions, no condition may be indicated or a label indicating that the patient is a control subject may be indicated.

At step 610 retinal signal features may be generated. The retinal signal features may be generated using a transform process. Retinal signal features may be generated for each set of retinal signal data retrieved at step 605.

At step 615 descriptors may be extracted from the retinal signal features in the datasets. The descriptors may be features selected as most representative of a condition.

At step 620 the descriptors may be ranked. Each descriptor may be ranked based on the level of statistical significance of the descriptor when testing the contribution of the descriptor to discriminating between conditions and/or between the condition and a control (i.e. no diagnosed condition).

At step 625 descriptors may be selected based on their rankings. A pre-determined amount of highest-ranked descriptors may be selected.

At step 630 an MLA may be trained using the selected descriptors. The datasets retrieved at 605 may be filtered to remove descriptors other than those descriptors selected at step 625. All or a portion of the datasets may then be used to train the MLA. The MLA may be trained to predict, based on a set of descriptors corresponding to a patient, the likelihood that the patient is subject to a condition.

Figure 7:
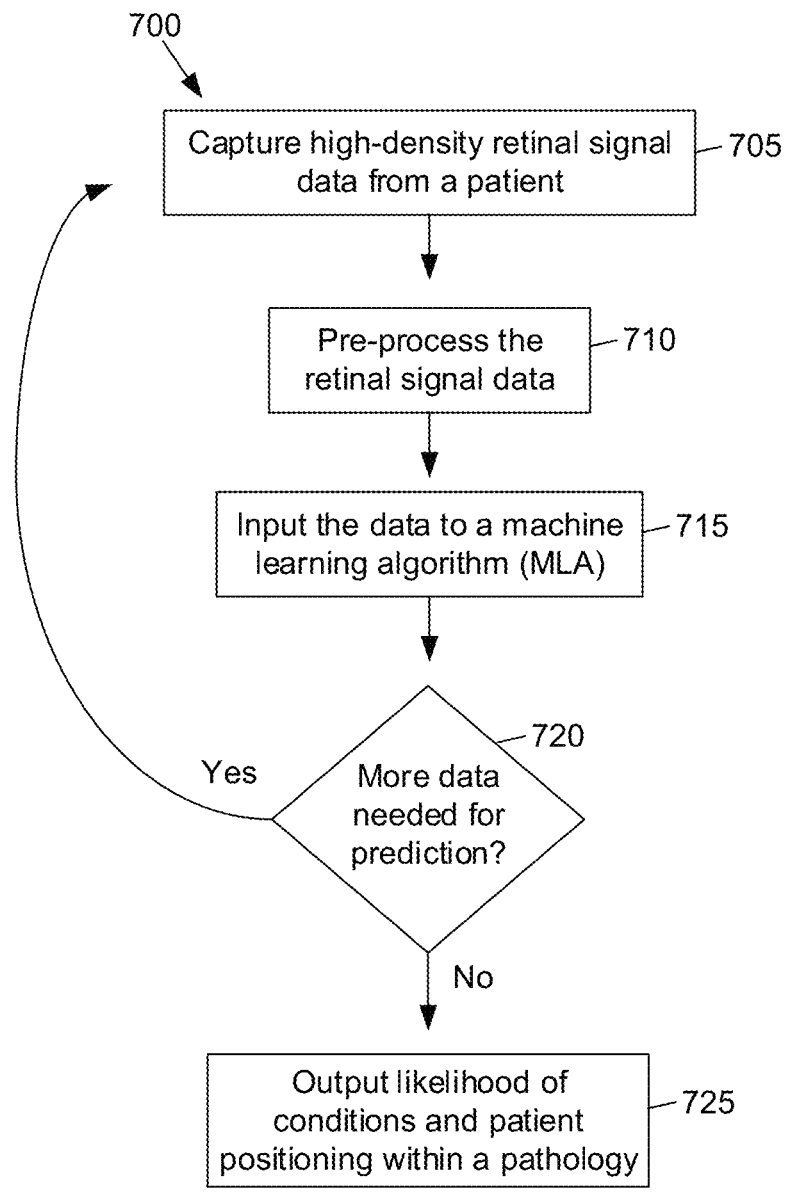
FIG. 7 illustrates a flow diagram of a method for using an MLA to predict a likelihood of a medical condition in accordance with various embodiments of the present technology.

After training the MLA, the MLA may be used to predict, based on measured retinal signal data, the likelihood that a patient is subject to a condition. FIG. 7 illustrates a flow diagram of a method 700 for using an MLA to predict a likelihood of a psychiatric condition in accordance with various embodiments of the present technology. All or portions of the method 700 may be executed by the data collection system 215, data analysis system 220, and/or the prediction output system 225. In one or more aspects, the method 700 or one or more steps thereof may be performed by a computing system, such as the computing environment 100. The method 700 or one or more steps thereof may be embodied in computer-executable instructions that are stored in a computer-readable medium, such as a non-transitory mass storage device, loaded into memory and executed by a CPU. The method 700 is exemplary, and it should be understood that some steps or portions of steps in the flow diagram may be omitted and/or changed in order.

At step 705 retinal signal data may of a patient may be collected. Actions performed at step 505 may be similar to those described above with regard to step 405.

At step 710 retinal signal features and/or descriptors may be extracted from the retinal signal data. The descriptors may be extracted to correspond to an MLA, such as the MLA generated using the method 600.

At step 715 the descriptors may be input to an MLA. Clinical information cofactors of the patient may also be input to the MLA. The MLA may be configured to predict the likelihood that the patient is subject to a condition based on descriptors and/or clinical information cofactors. The MLA may be an MLA generated using the method 600.

At step 720 a determination may be made as to whether more data should be input to the MLA. The MLA may determine that the data input at step 715 is insufficient for making a prediction. The MLA may determine that the amount of data is insufficient. The MLA may determine that the data is not accurate enough to make a prediction, such as if there are errors in the data. The MLA may output a confidence level of the prediction, and a determination may be made that the confidence level is below a threshold confidence level, such as a pre-determined threshold confidence level. If the MLA requires more data, more data may be captured at step 705. Otherwise, if the MLA has a sufficient amount of data to make a prediction the method 700 may continue to step 725.

At step 725 the MLA may output a predicted likelihood that the patient is subject to one or more conditions. For each condition, the MLA may output a predicted likelihood that the patient is subject to the condition. A patient positioning within a pathology may be output by the MLA and/or may be determined based on the predictions output by the MLA. The patient positioning may indicate a distance of the patient from a biosignature of a condition. A user interface and/or report may be generated and output to a clinician for use as an aid in determining a medical condition of a patient and/or confirming a medical condition.

Examples for time-frequency analysis and selection of discriminant areas based upon statistical significance of frequency of higher magnitude are illustrated in FIGS. 8 to 27. In these examples, retinal signal data from patients with schizophrenia, bipolar disorder or major depressive disorder, young population at risk of psychoses (i.e. young offspring with parents affected by schizophrenia, bipolar disorder or depression) and from control subjects not affected by those conditions, were subjected to time-frequency analysis (wavelet transform with different mother wavelets) and compared. Time-frequency analysis is conducted with any known mother wavelet or a specific mother wavelet prepared (prototype mother wavelets) from reference datasets (control subject or individuals with specific conditions).

Examples for selection and statistical significance mapping of retinal signal features are illustrated in FIGS. 28 to 42. In these examples, retinal signal features obtained with signal frequency analysis in patients with schizophrenia, bipolar disorder, or major depression disorder, young population at risk of psychoses (i.e. young offspring with parents affected by schizophrenia, bipolar disorder or depression) and from control subjects not affected by those conditions, were selected and compared. Mappings of the most discriminant features are then prepared from the feature selection.

Examples for selection and statistical significance mapping of retinal signal descriptors are illustrated in FIGS. 43 to 58. In these examples, retinal signal descriptors obtained in patients with schizophrenia, bipolar disorder, or major depression disorder, young population at risk of psychoses (i.e. young offspring with parents affected by schizophrenia, bipolar disorder or depression) and from control subjects not affected by those conditions, were combined and their potential for discriminating within several conditions were assessed. Mappings of the most discriminating descriptors are then prepared from that selection, based upon their differentiating potential and their location within the volume of information.

Figure 8:
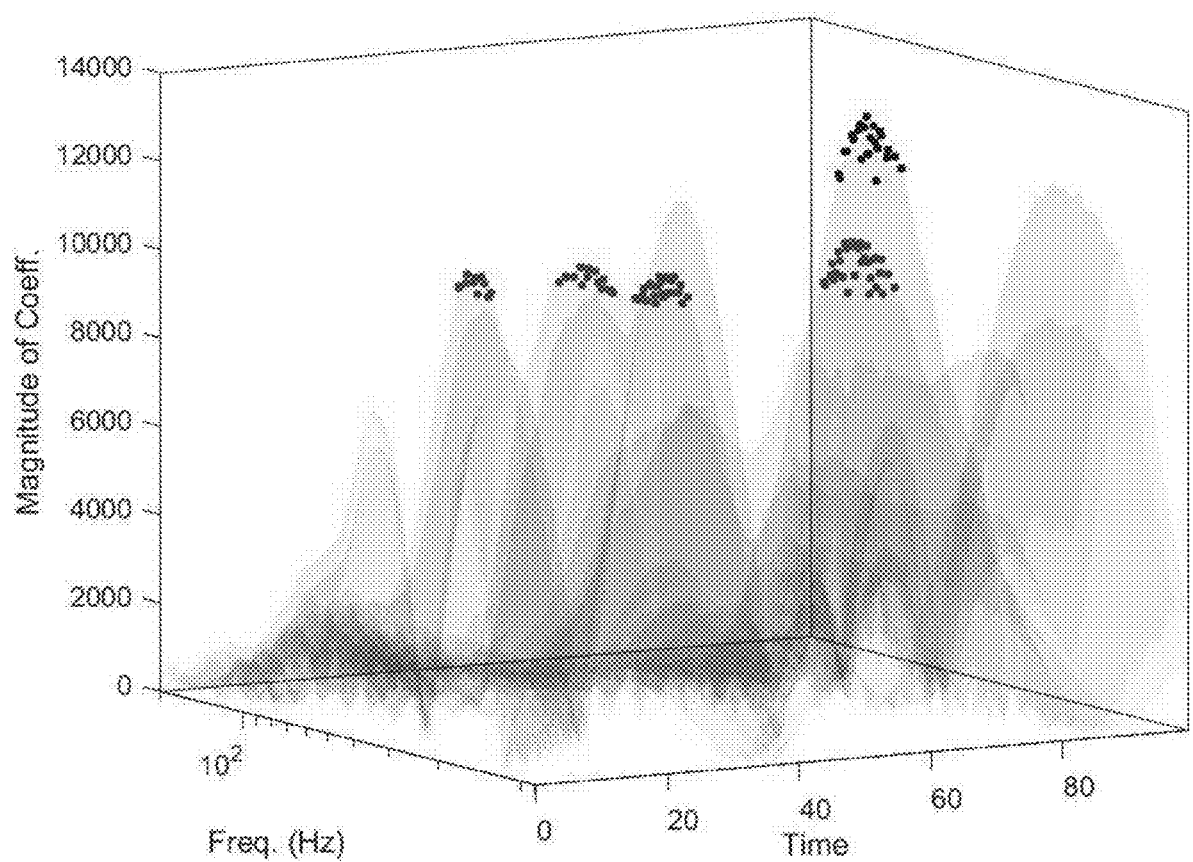
FIGS. 8 to 27 illustrate examples of time-frequency analysis and selection of discriminant areas based upon statistical significance of frequency of higher magnitude in accordance with various embodiments of the present technology.

FIG. 8 illustrates a comparison of retinal signal data frequency analysis in patients with schizophrenia (blue/grey dots) versus individuals not diagnosed with mental health conditions (control subjects; red/dark dots) using discrete approximation of Morlet waveform as mother wavelet. The magnitude of SRC coefficients versus time and frequency is at a threshold comparison of 90%.

Figure 9:
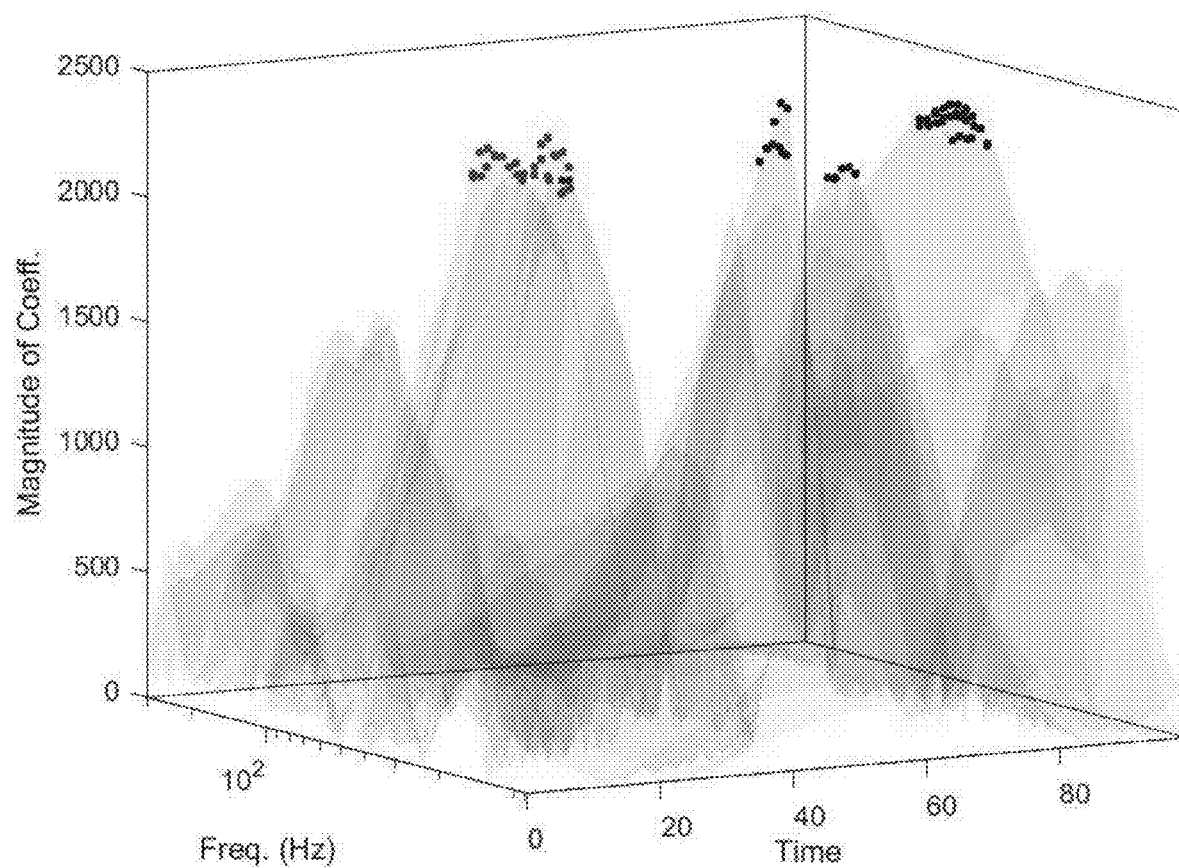

FIG. 9 illustrates a comparison of retinal signal data frequency analysis in patients with schizophrenia (blue/grey dots) versus individuals not diagnosed with mental health conditions (control subjects; red/dark dots) using discrete approximation of a mother wavelet specifically designed with retinal signal datasets from control subjects. The magnitude of SRC coefficients versus time and frequency is at a threshold comparison of 90%.

Figure 10:
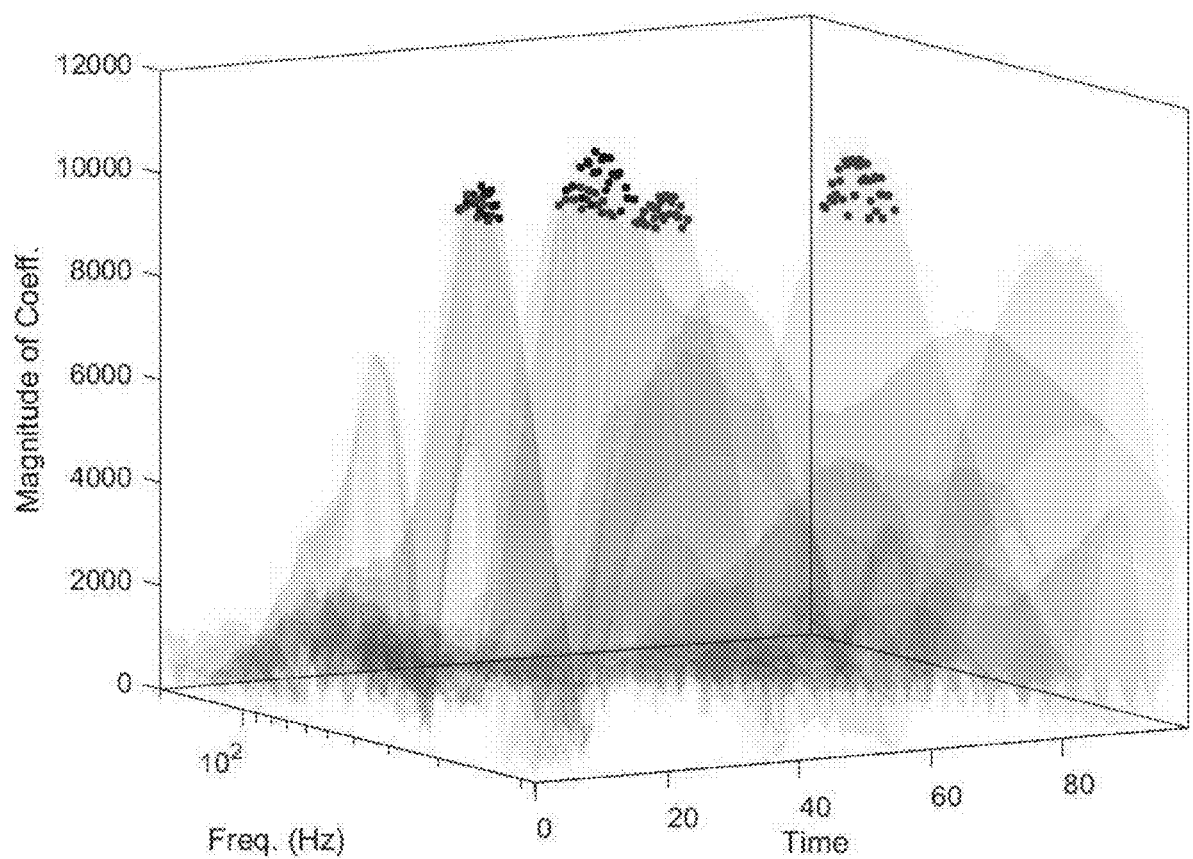

FIG. 10 illustrates a comparison of retinal signal data frequency analysis in patients with bipolar disorder (blue/grey dots) versus individuals not diagnosed with mental health conditions (control subjects; red/dark dots) using discrete approximation of Morlet waveform as mother wavelet. The magnitude of SRC coefficients versus time and frequency is at a threshold comparison of 90%.

Figure 11:
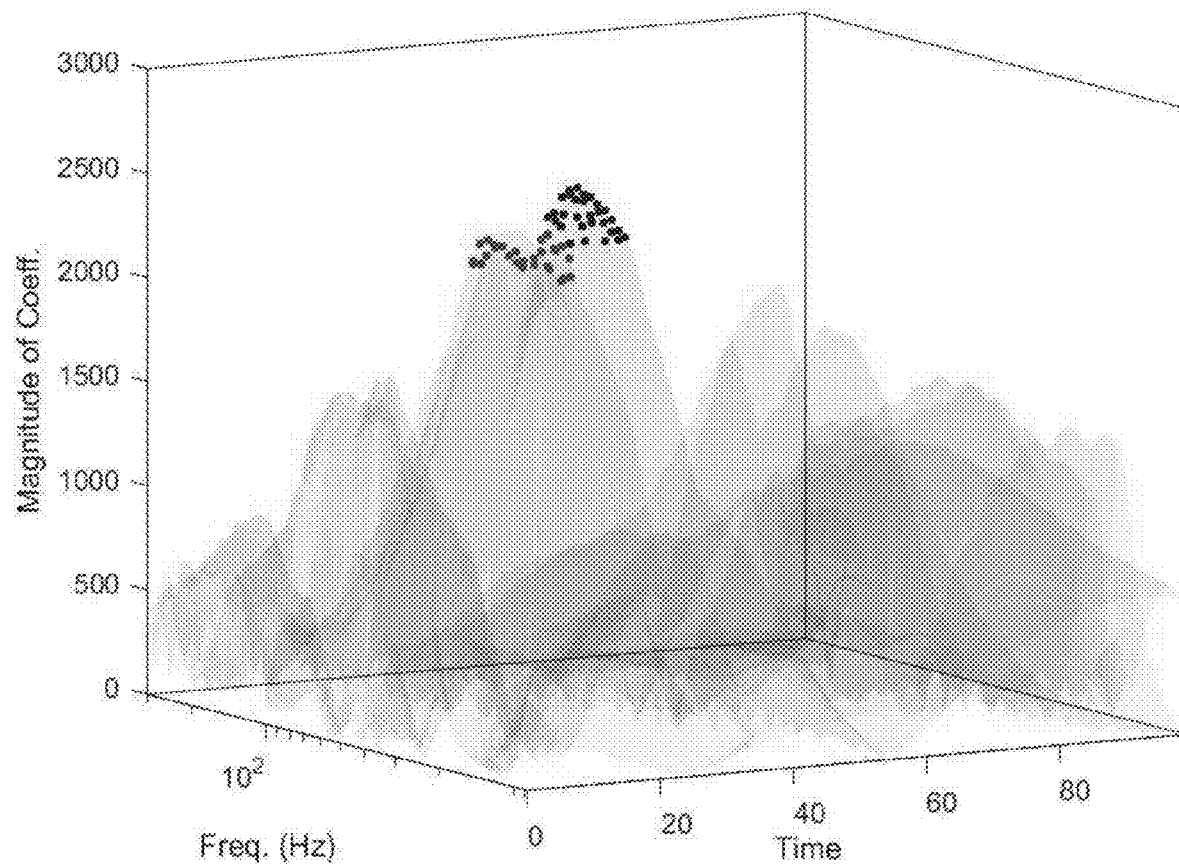

FIG. 11 illustrates a comparison of retinal signal data frequency analysis in patients with bipolar disorder (blue/grey dots) versus individuals not diagnosed with mental health conditions (control subjects; red/dark dots) using discrete approximation of a mother wavelet specifically designed with retinal signal datasets from control subjects. The magnitude of SRC coefficients versus time and frequency is at a threshold comparison of 90%.

Figure 12:
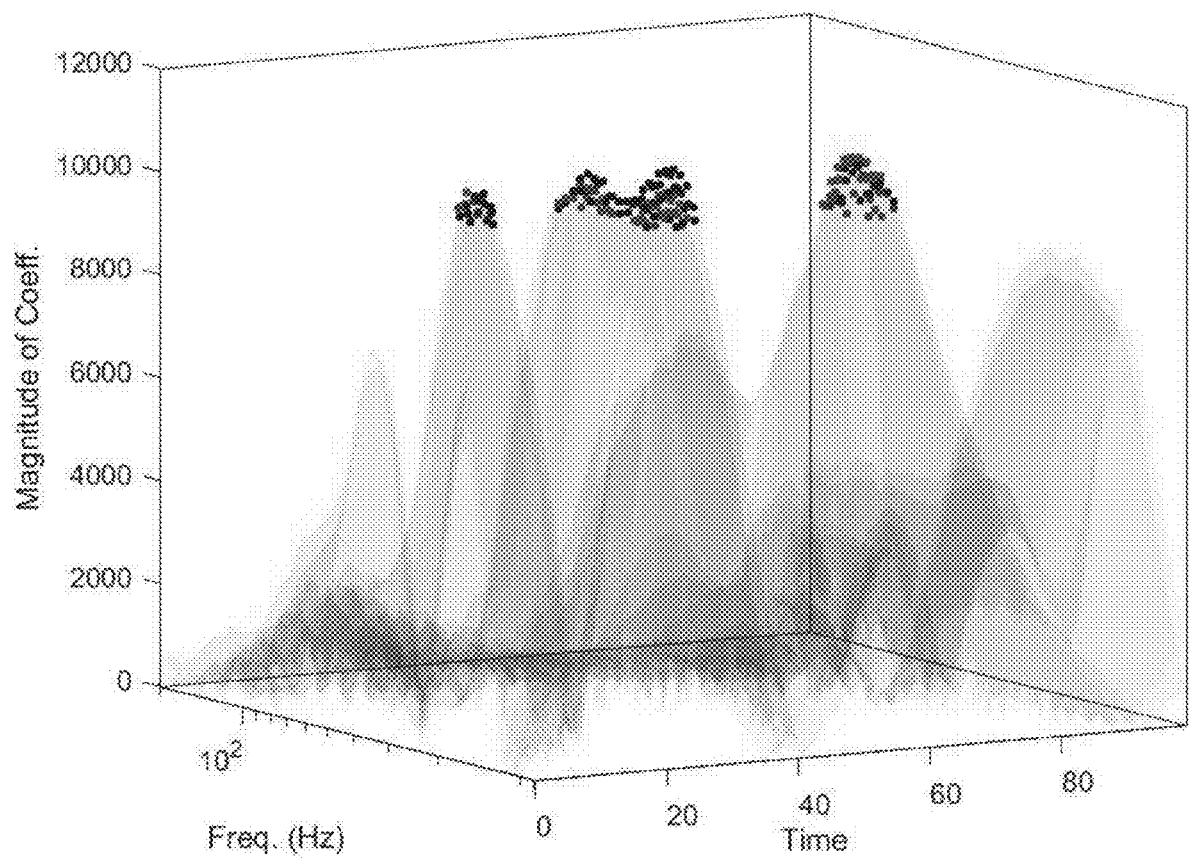

FIG. 12 illustrates a comparison of retinal signal data frequency analysis in patients with major depressive disorder (blue/grey dots) versus individuals not diagnosed with mental health conditions (control subjects; red/dark dots) using discrete approximation of Morlet waveform as mother wavelet. The magnitude of SRC coefficients versus time and frequency is at a threshold comparison of 90%.

Figure 13:
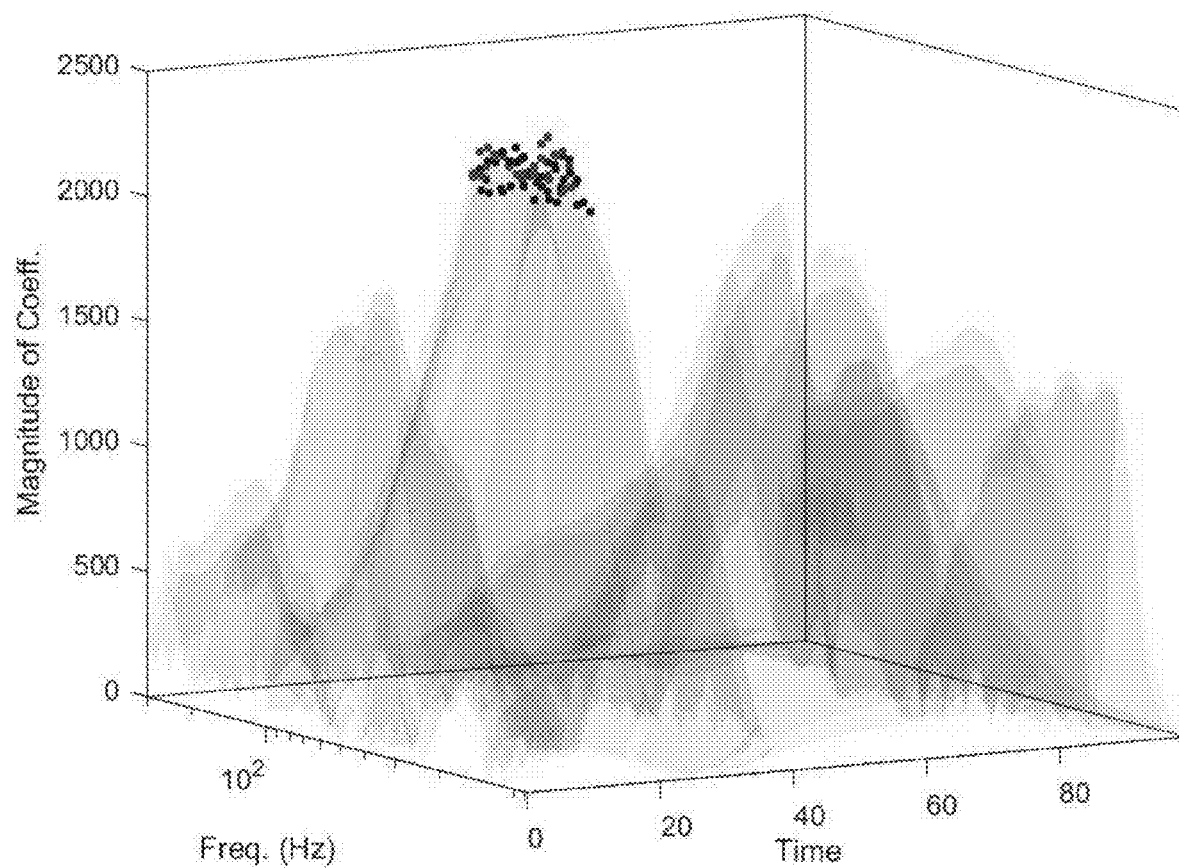

FIG. 13 illustrates a comparison of retinal signal data frequency analysis in patients with major depressive disorder (blue/grey dots) versus individuals not diagnosed with mental health conditions (control subjects; red/dark dots) using discrete approximation of a mother wavelet specifically designed with retinal signal datasets from control subjects. The magnitude of SRC coefficients versus time and frequency is at a threshold comparison of 90%.

Figure 14:
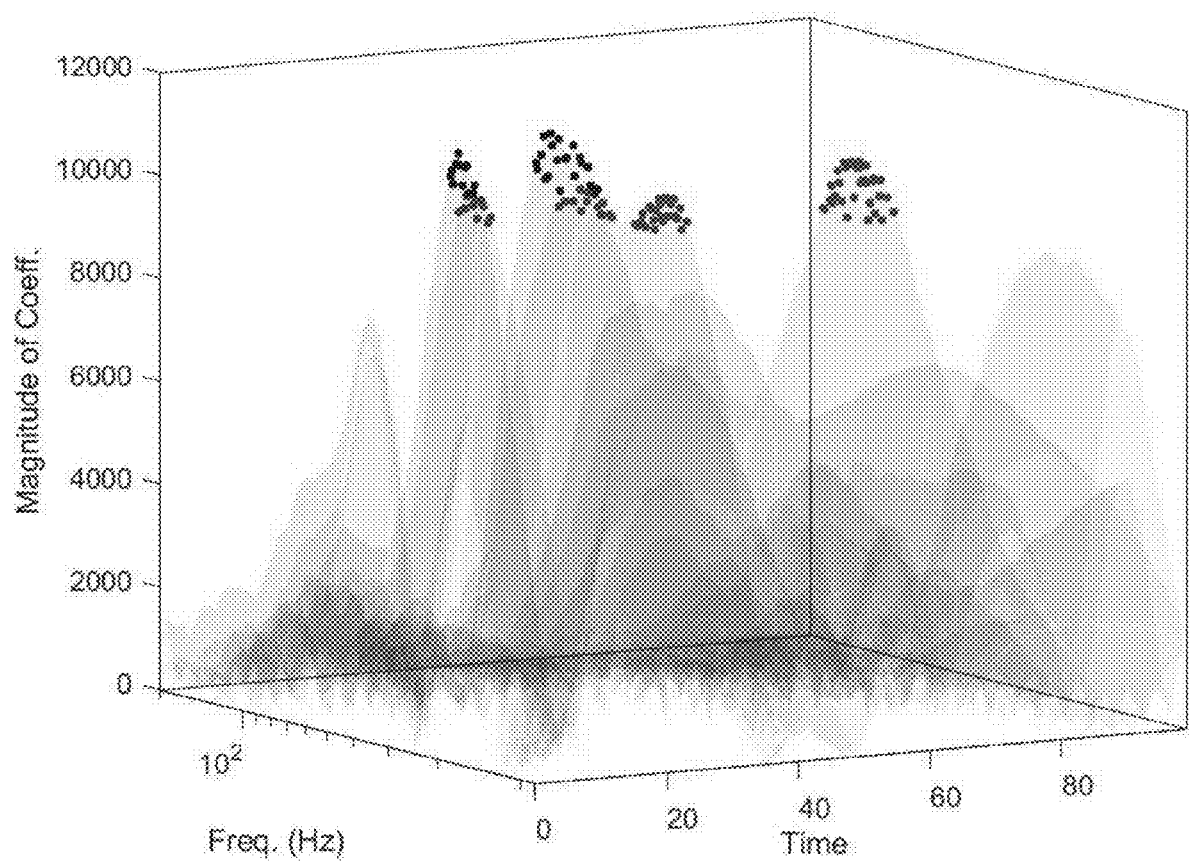

FIG. 14 illustrates a comparison of retinal signal data frequency analysis in patients at risk of psychoses (blue/grey dots) versus individuals not diagnosed with mental health conditions (control subjects; red/dark dots) using discrete approximation of Morlet waveform as mother wavelet. The magnitude of SRC coefficients versus time and frequency is at a threshold comparison of 90%.

Figure 15:
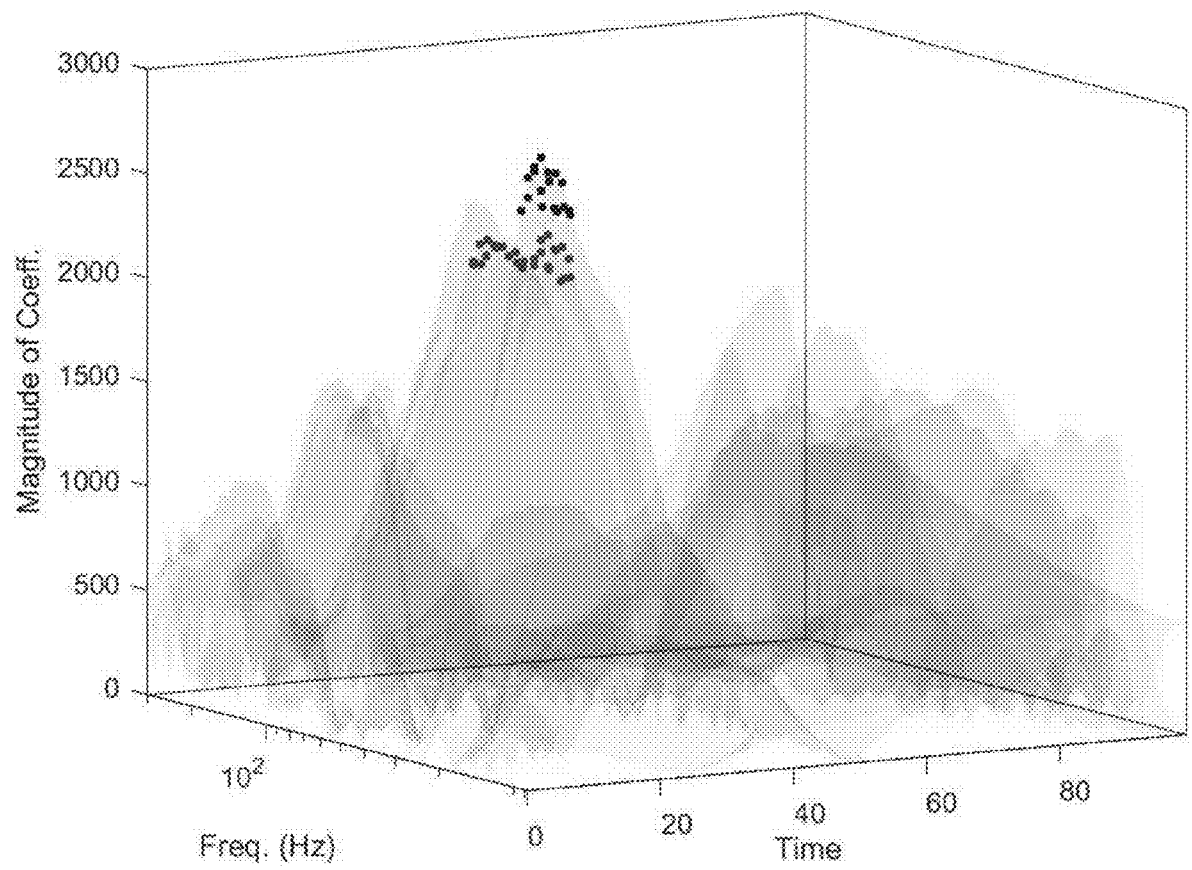

FIG. 15 illustrates a comparison of retinal signal data frequency analysis in patients at risk of psychoses (blue/grey dots) versus individuals not diagnosed with mental health conditions (control subjects; red/dark dots) using discrete approximation of a mother wavelet specifically designed with retinal signal datasets from control subjects. The magnitude of SRC coefficients versus time and frequency is at a threshold comparison of 90%.

Figure 16:
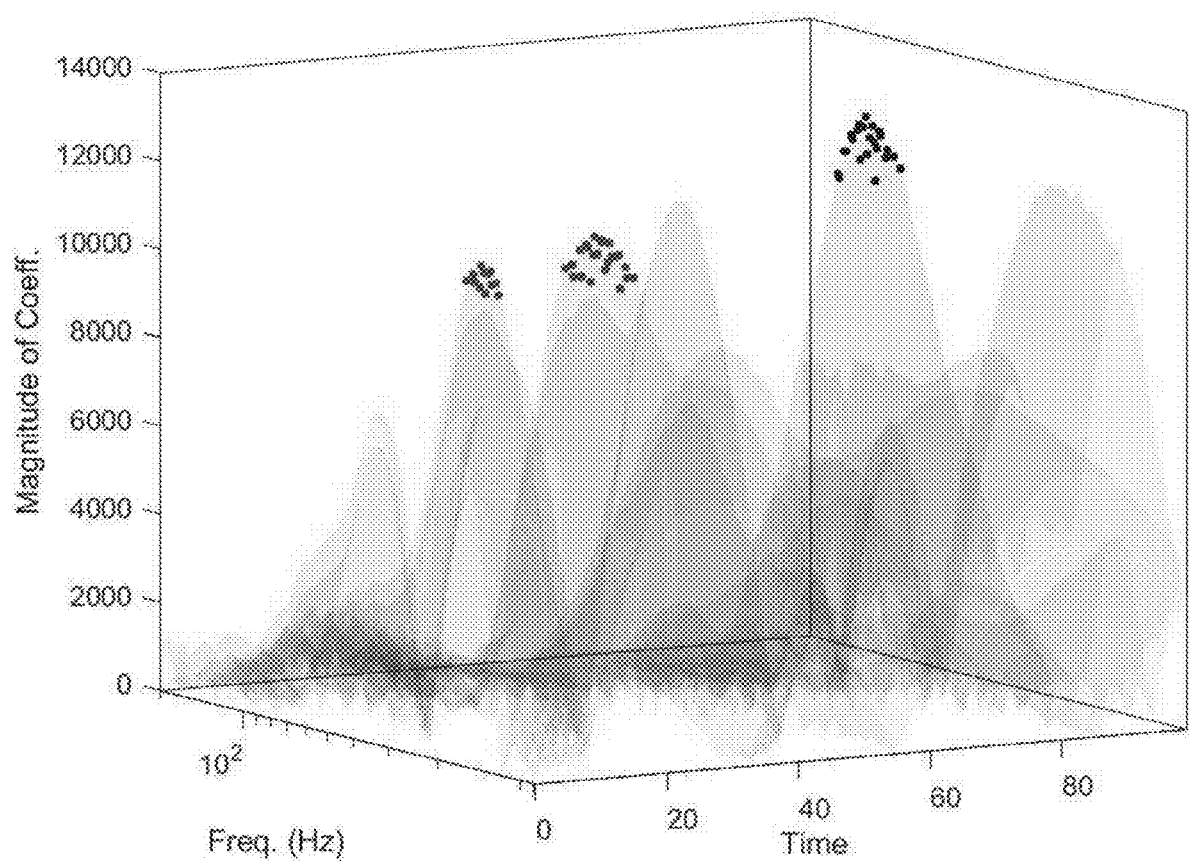

FIG. 16 illustrates a comparison of retinal signal data frequency analysis in patients with schizophrenia (blue/grey dots) versus patients with bipolar disorder (red/dark dots) using discrete approximation of Morlet waveform as mother wavelet. The magnitude of SRC coefficients versus time and frequency is at a threshold comparison of 90%.

Figure 17:
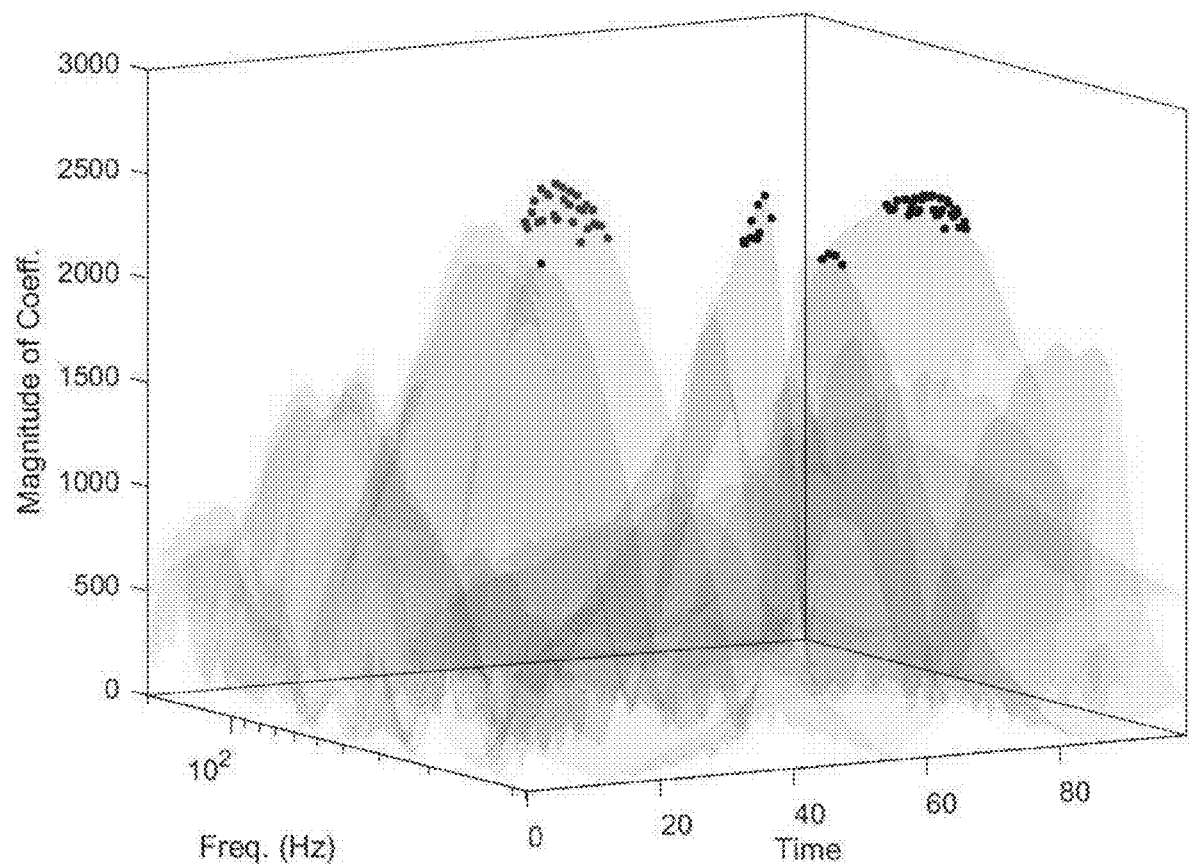

FIG. 17 illustrates a comparison of retinal signal data frequency analysis in patients with schizophrenia (blue/grey dots) versus patients with bipolar disorder (red/dark dots) using discrete approximation of a mother wavelet specifically designed with retinal signal datasets from control subjects. The magnitude of SRC coefficients versus time and frequency is at a threshold comparison of 90%.

Figure 18:
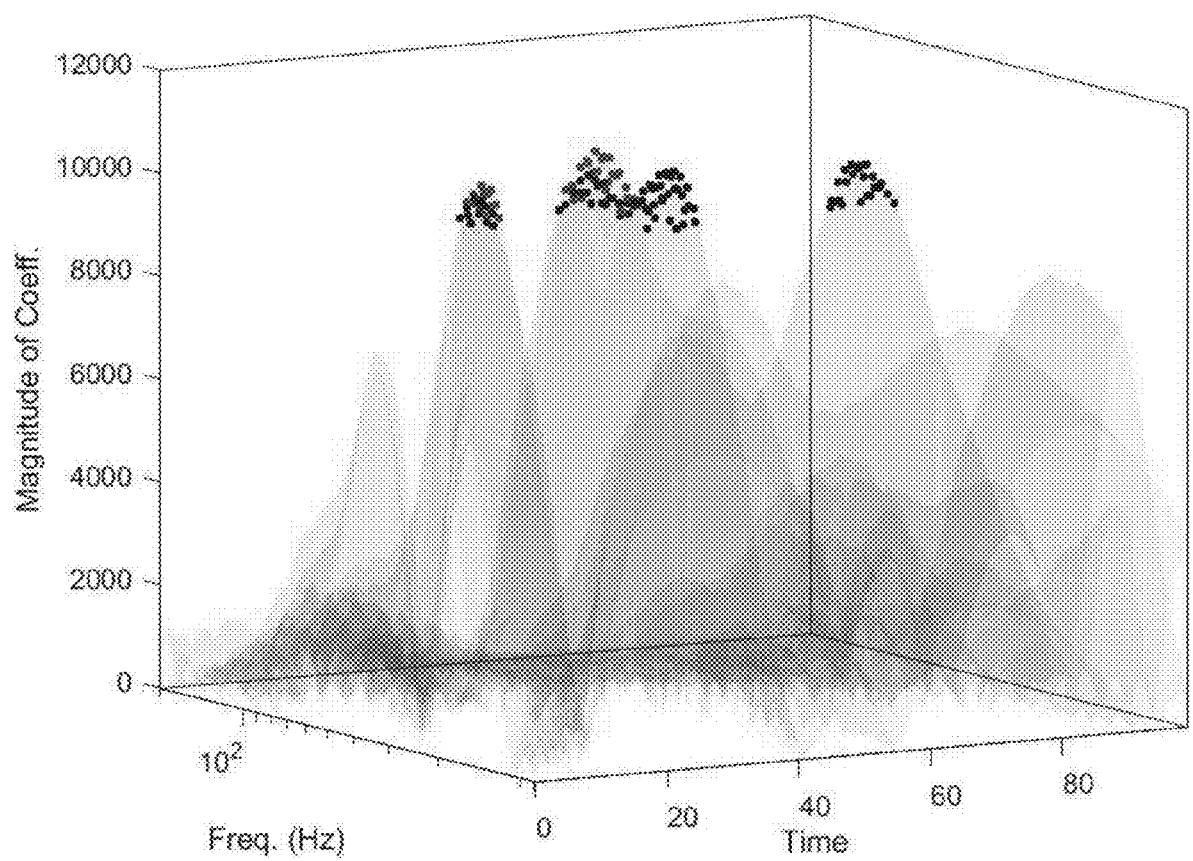

FIG. 18 illustrates a comparison of retinal signal data frequency analysis in patients with major depressive disorder (blue/grey dots) versus patients with bipolar disorder (red/dark dots) using discrete approximation of Morlet waveform as mother wavelet. The magnitude of SRC coefficients versus time and frequency is at a threshold comparison of 90%.

Figure 19:
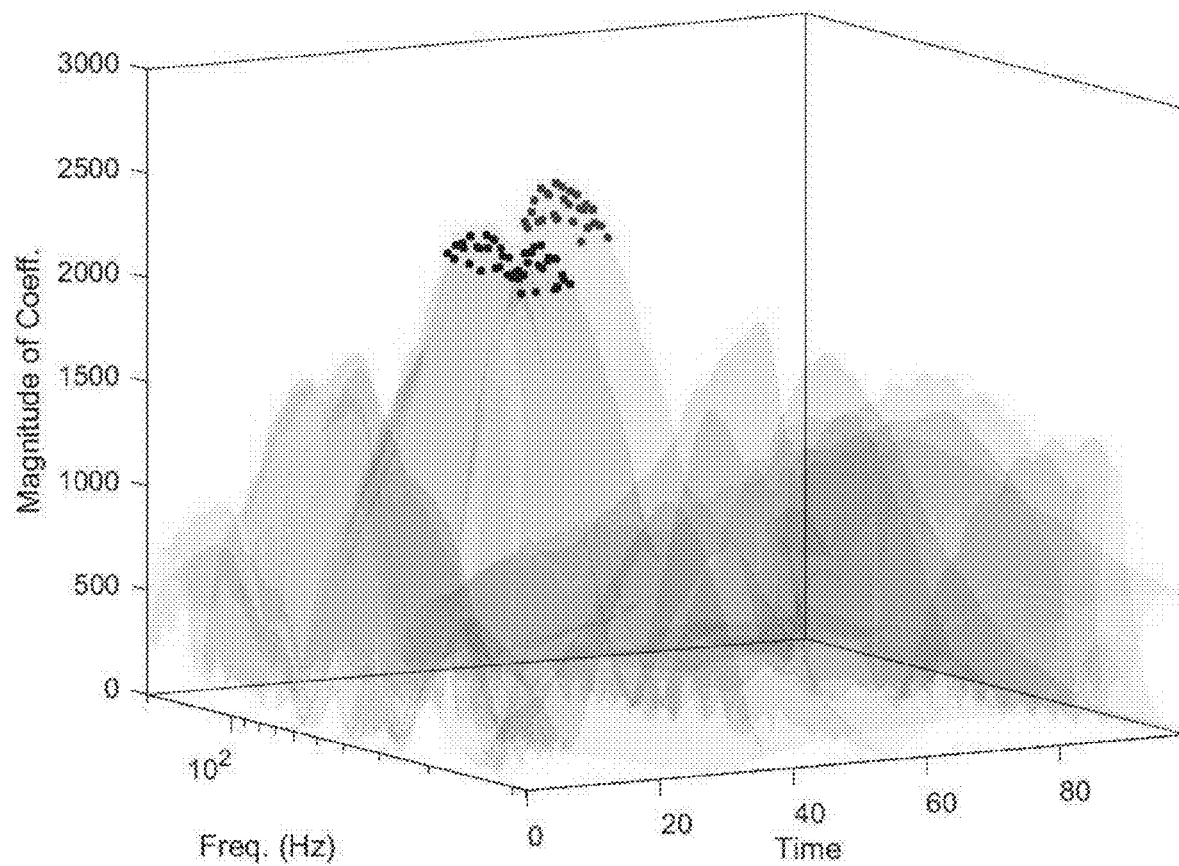

FIG. 19 illustrates a comparison of retinal signal data frequency analysis in patients with major depressive disorder (blue/grey dots) versus patients with bipolar disorder (red/dark dots) using discrete approximation of a mother wavelet specifically designed with retinal signal datasets from control subjects. The magnitude of SRC coefficients versus time and frequency is at a threshold comparison of 90%.

Figure 20:
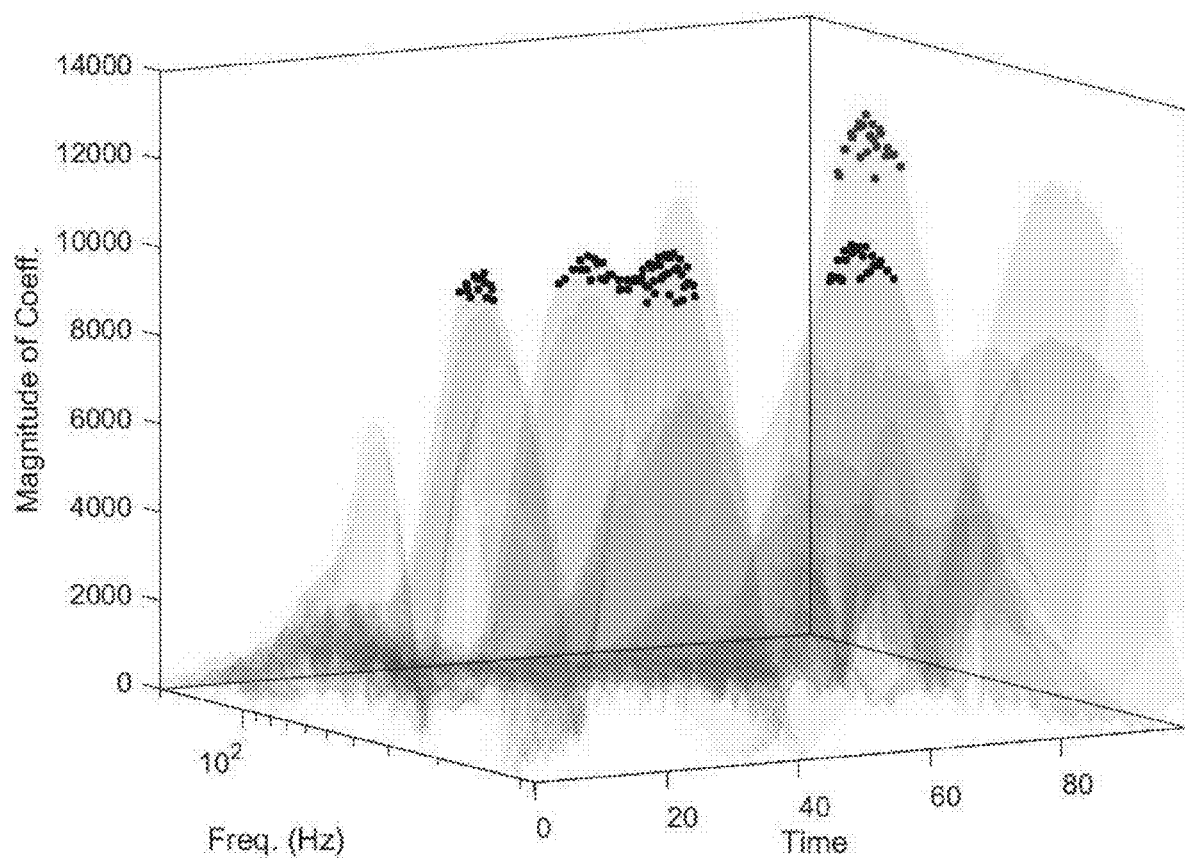

FIG. 20 illustrates a comparison of retinal signal data frequency analysis in patients with major depressive disorder (blue/grey dots) versus patients with schizophrenia (red/dark dots) using discrete approximation of Morlet waveform as mother wavelet. The magnitude of SRC coefficients versus time and frequency is at a threshold comparison of 90%.

Figure 21:
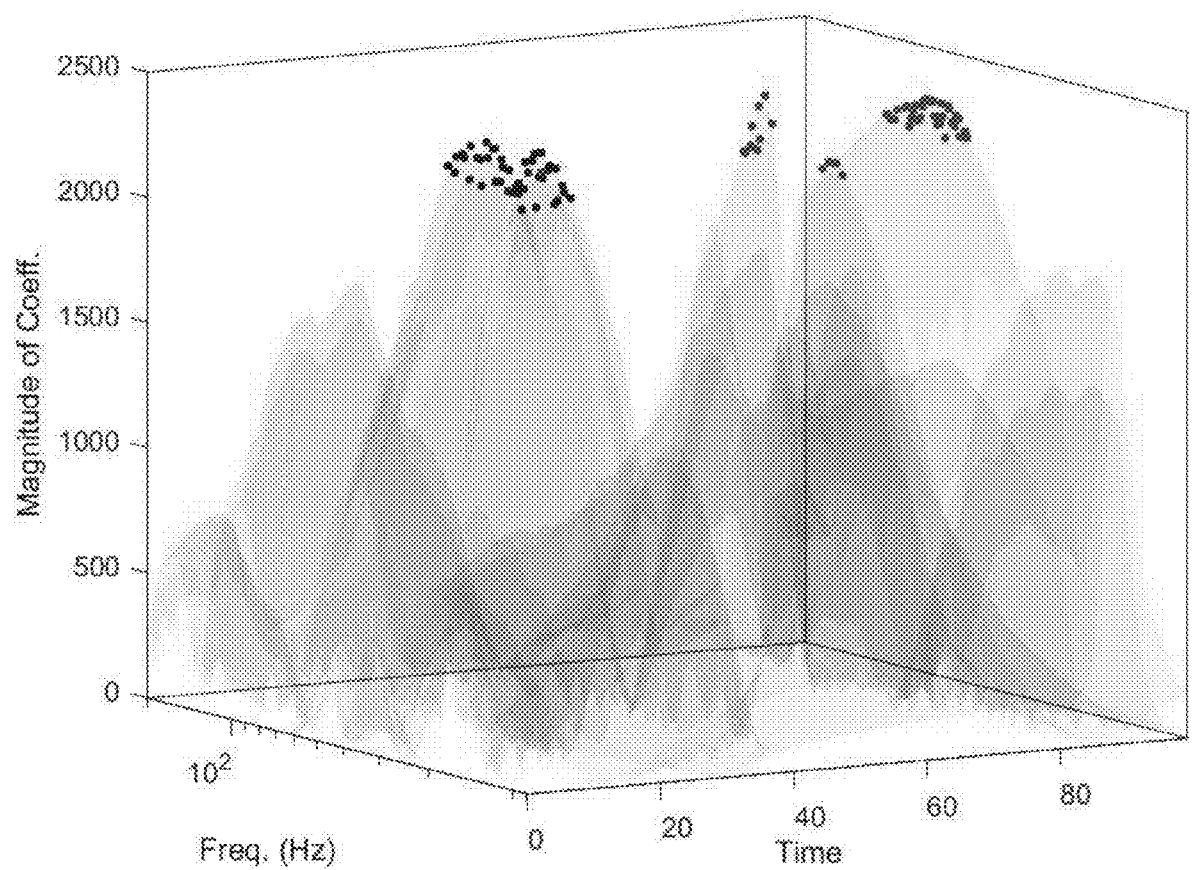

FIG. 21 illustrates a comparison of retinal signal data frequency analysis in patients with major depressive disorder (blue/grey dots) versus patients with schizophrenia (red/dark dots) using discrete approximation of a mother wavelet specifically designed with retinal signal datasets from control subjects. The magnitude of SRC coefficients versus time and frequency is at a threshold comparison of 90%.

Figure 22:
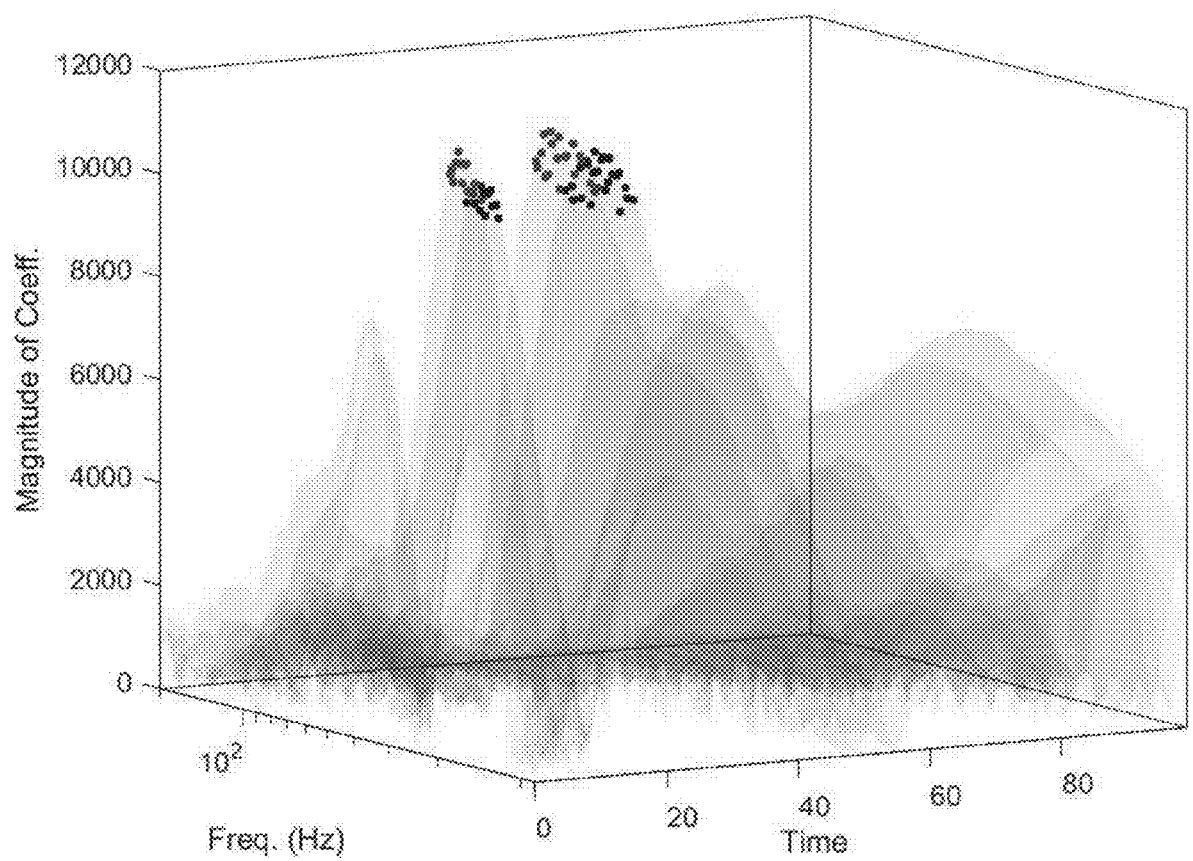

FIG. 22 illustrates a comparison of retinal signal data frequency analysis in patients with bipolar disorder (blue/grey dots) versus patients at risk of psychoses (red/dark dots) using discrete approximation of Morlet waveform as mother wavelet. The magnitude of SRC coefficients versus time and frequency is at a threshold comparison of 90%.

Figure 23:
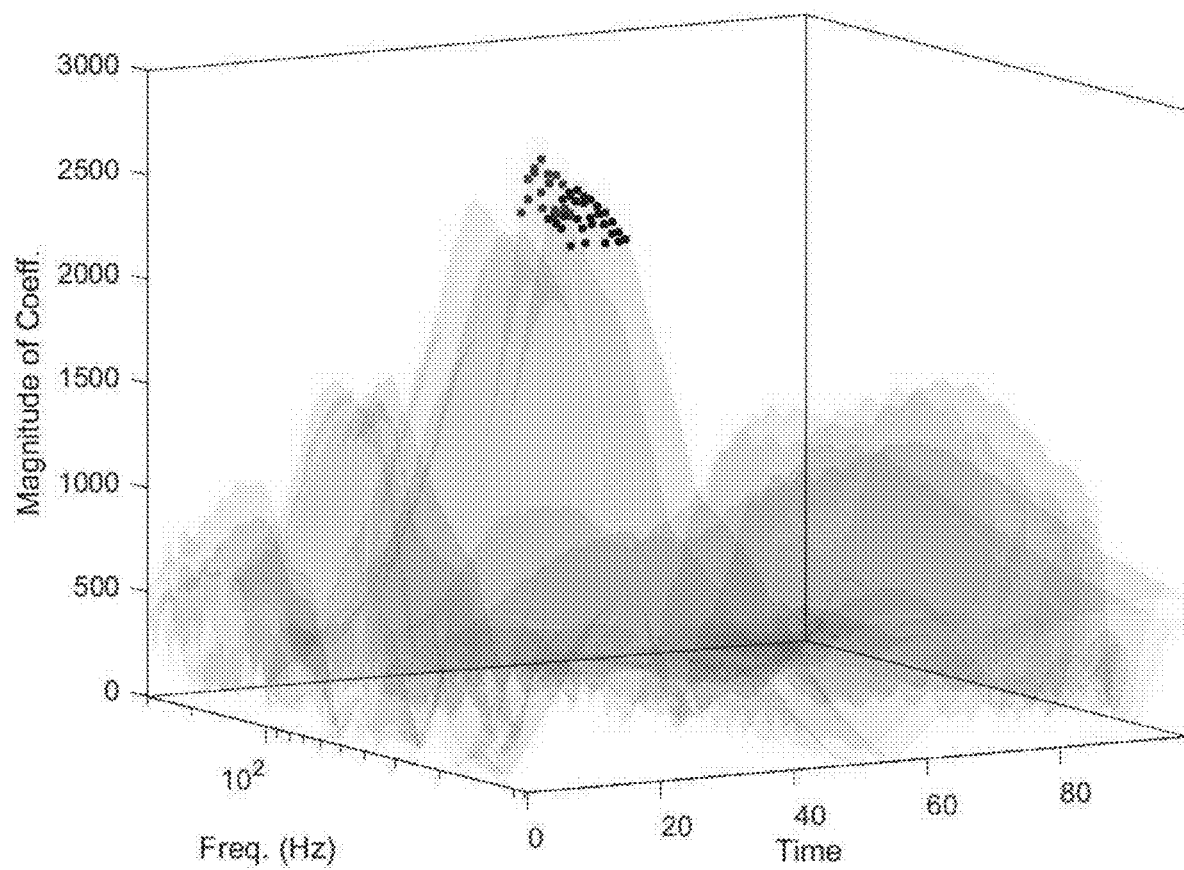

FIG. 23 illustrates a comparison of retinal signal data frequency analysis in patients with bipolar disorder (blue/grey dots) versus patients at risk of psychoses (red/dark dots) using discrete approximation of a mother wavelet specifically designed with retinal signal datasets from control subjects. The magnitude of SRC coefficients versus time and frequency is at a threshold comparison of 90%.

Figure 24:
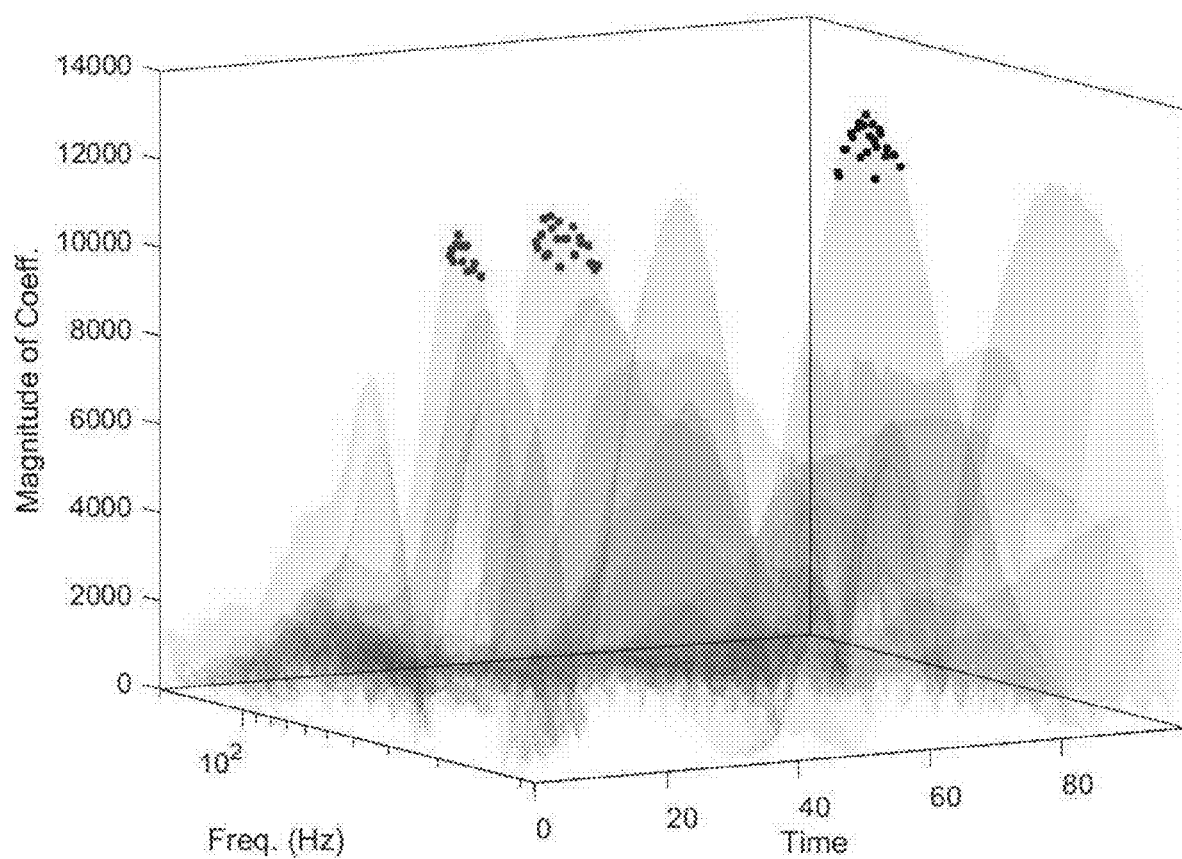

FIG. 24 illustrates a comparison of retinal signal data frequency analysis in patients with schizophrenia (blue/grey dots) versus patients at risk of psychoses (red/dark dots) using discrete approximation of Morlet waveform as mother wavelet. The magnitude of SRC coefficients versus time and frequency is at a threshold comparison of 90%.

Figure 25:
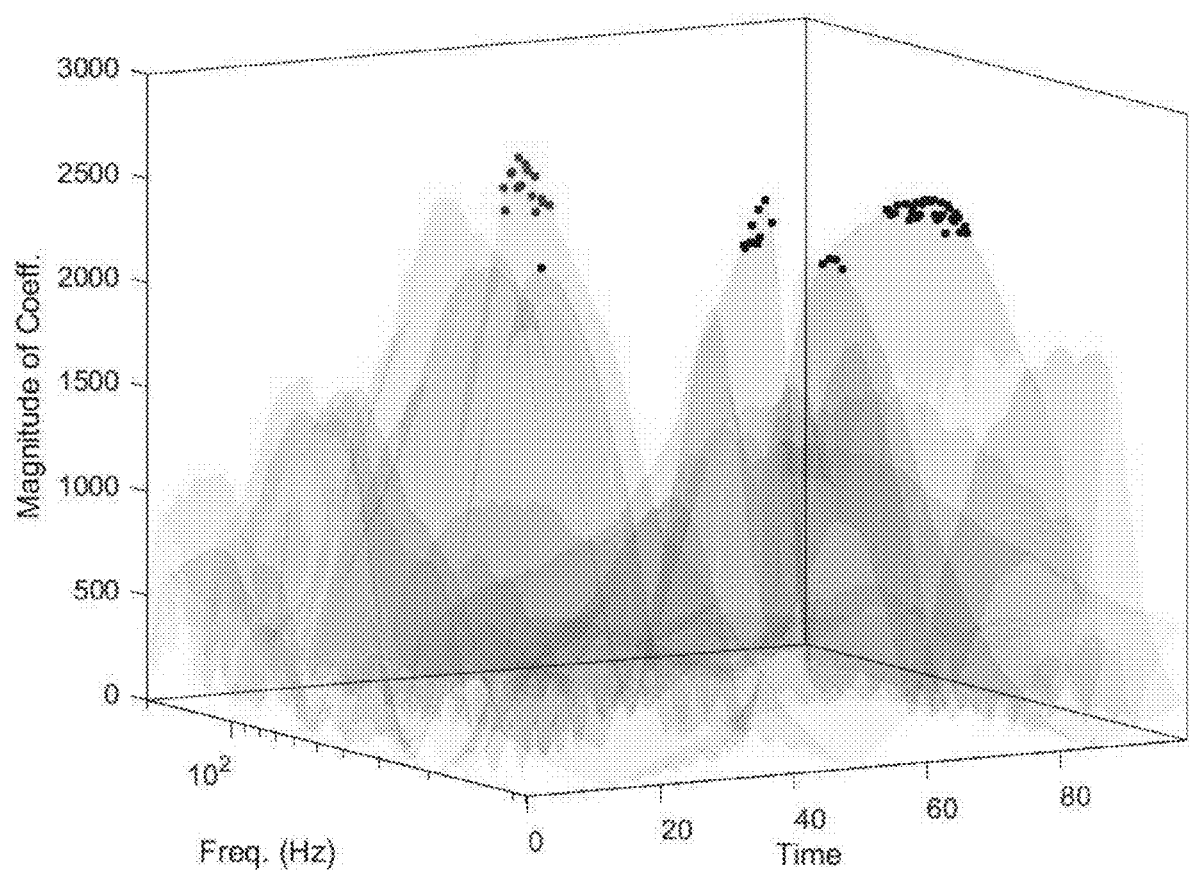

FIG. 25 illustrates a comparison of retinal signal data frequency analysis in patients with schizophrenia (blue/grey dots) versus patients at risk of psychoses (red/dark dots) using discrete approximation of a mother wavelet specifically designed with retinal signal datasets from control subjects. The magnitude of SRC coefficients versus time and frequency is at a threshold comparison of 90%.

Figure 26:
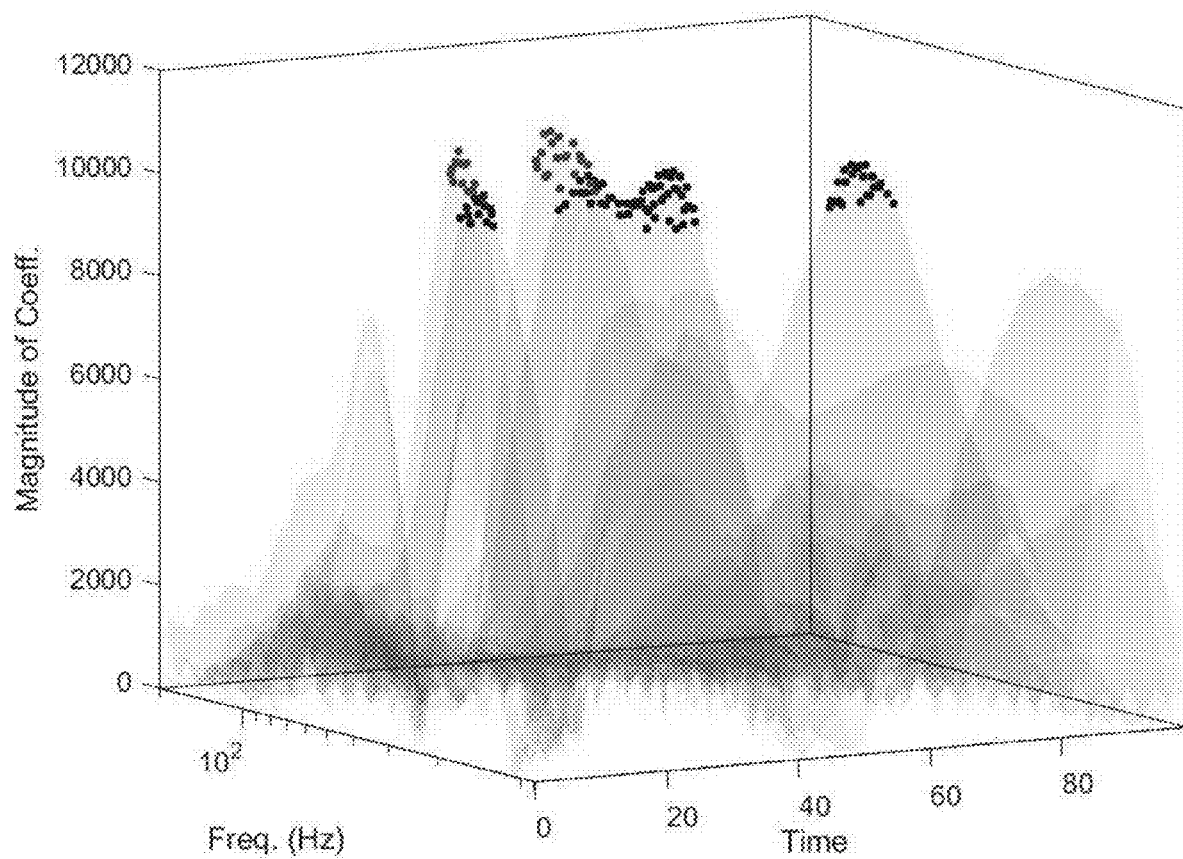

FIG. 26 illustrates a comparison of retinal signal data frequency analysis in patients with major depressive disorder (blue/grey dots) versus patients at risk of psychoses (red/dark dots) using discrete approximation of Morlet waveform as mother wavelet. The magnitude of SRC coefficients versus time and frequency is at a threshold comparison of 90%.

Figure 27:
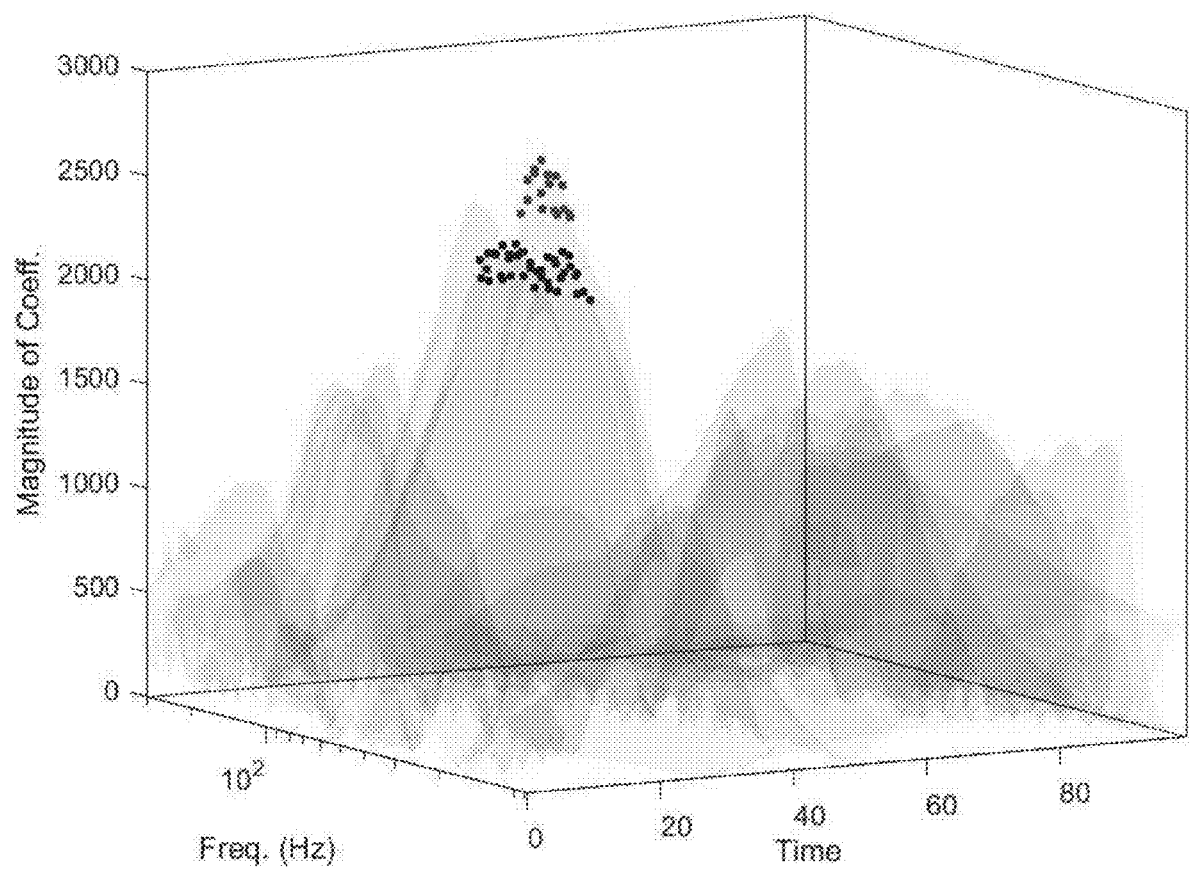

FIG. 27 illustrates a comparison of retinal signal data frequency analysis in patients with major depressive disorder (blue/grey dots) versus patients at risk of psychoses (red/dark dots) using discrete approximation of a mother wavelet specifically designed with retinal signal datasets from control subjects. The magnitude of SRC coefficients versus time and frequency is at a threshold comparison of 90%.

Figure 28:
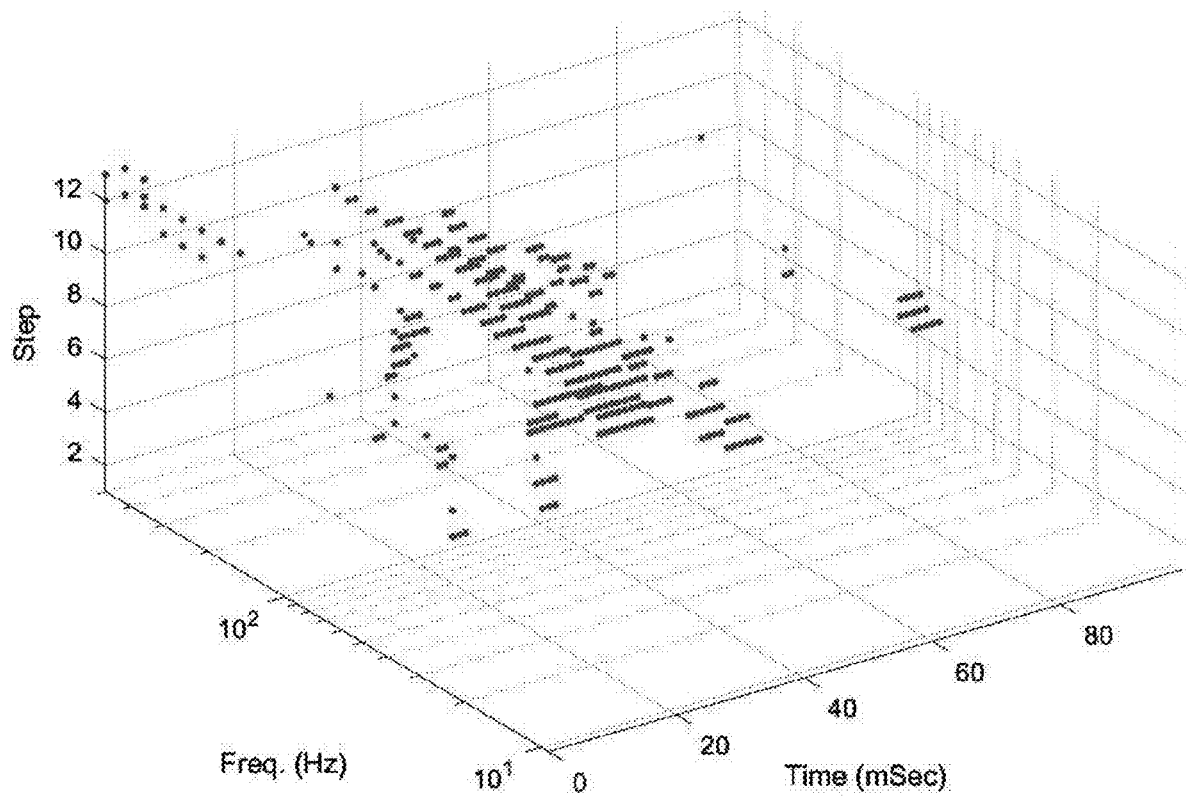
FIGS. 28 to 42 illustrate examples of retinal signal feature selection and statistical significance mapping of selected retinal signal features in accordance with various embodiments of the present technology.

FIG. 28 illustrates most discriminant predictors from features selection (frequency analysis components in that example) conducted with Sparse Representation based Classification (SRC) on wavelet coefficient at a threshold of $p \leq 0.05$ in patients with bipolar disorder versus patients with schizophrenia using discrete approximation of a mother wavelet specifically designed with retinal signal datasets from control subjects. Colors are scales of magnitude of SRC in a specific position. Red dots (dark dots) are depicting SRC positions with SRC higher than the defined threshold (in the illustrated example, the threshold is from 70% to 100%).

Figure 29:
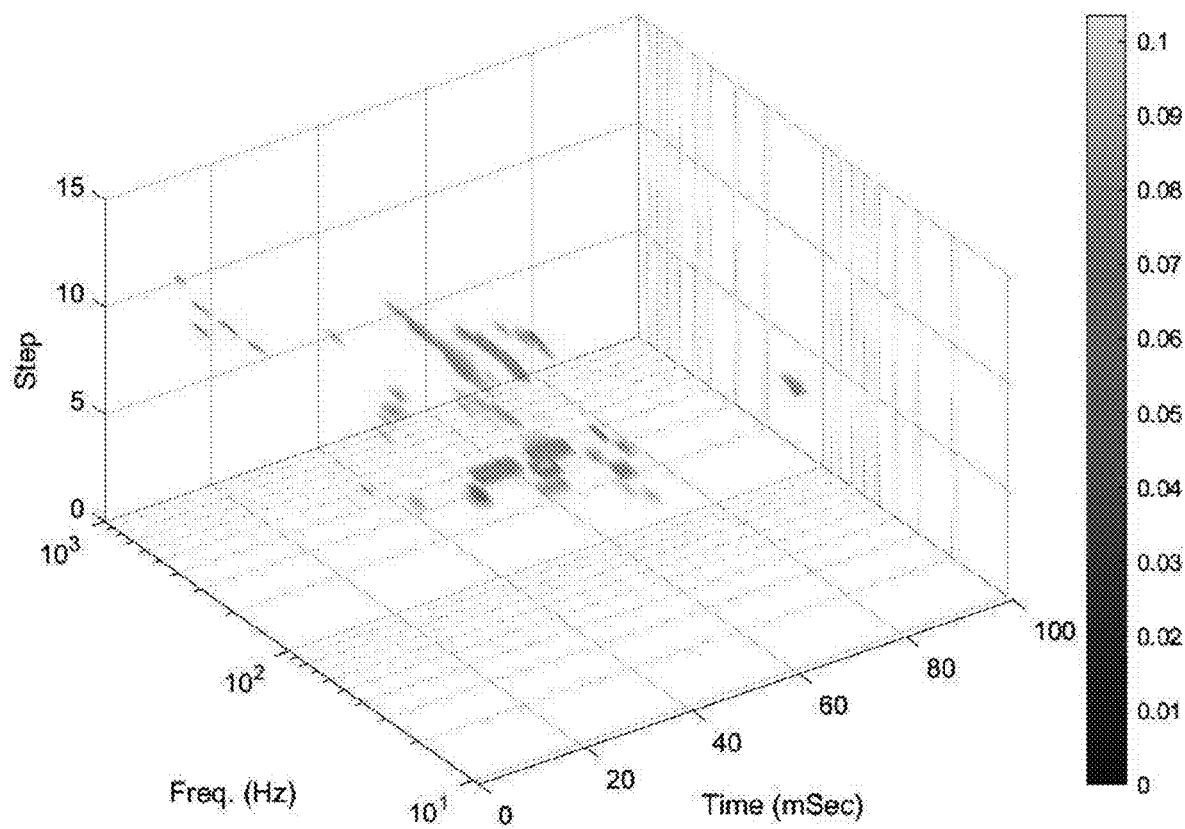

FIG. 29 illustrates most discriminant predictors from features selection (frequency analysis components in that example) conducted with Principal Component Analysis classification based upon statistical significance at a threshold of statistical p value$\leq 0.05$ in patients with bipolar disorder versus patients with schizophrenia, using of a mother wavelet specifically designed with retinal signal datasets from control subjects.

Figure 30:
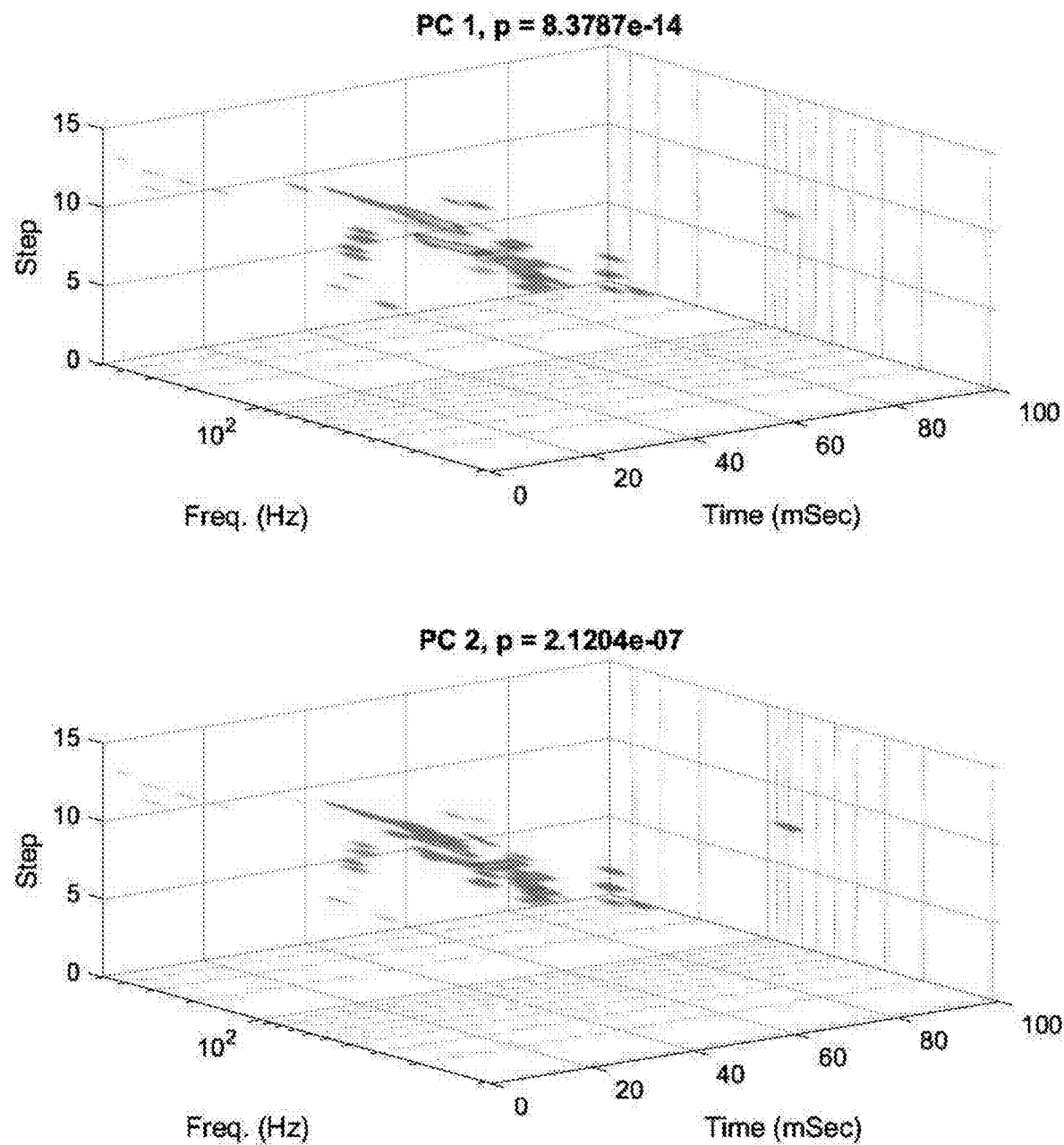

FIG. 30 illustrates mappings of the most discriminant predictors and their levels of significance (statistical p values) from features selection (frequency analysis components in that example) conducted with Principal Component Analysis classification ranked by statistical significance in patients with bipolar disorder versus patients with schizophrenia, using a mother wavelet specifically designed with retinal signal datasets from control subjects. In this example, the two most discriminant components were considered at a threshold of p≤0.05. Colors (grey scale) are scales of magnitude of the discriminant power.

Figure 31:
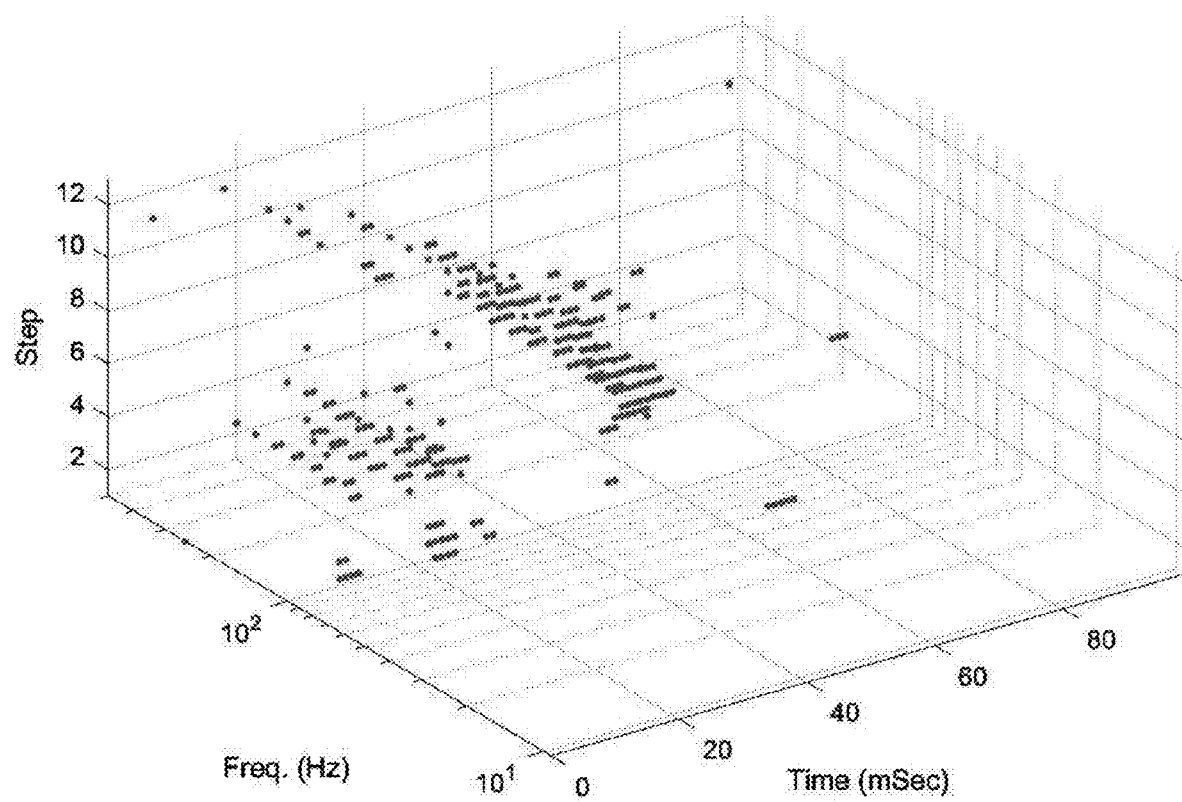

FIG. 31 illustrates most discriminant predictors from features selection (frequency analysis components in that example) conducted with Sparse Representation based Classification (SRC) on wavelet coefficient at a threshold of p≤0.05 in patients with bipolar disorder versus patients with major depressive disorder, using discrete approximation of a mother wavelet specifically designed with retinal signal datasets from control subjects. Colors are scales of magnitude of SRC in a specific position. Red dots (dark dots) are depicting SRC positions with SRC higher than the defined threshold (in the illustrated example, the threshold is from 70% to 100%).

Figure 32:
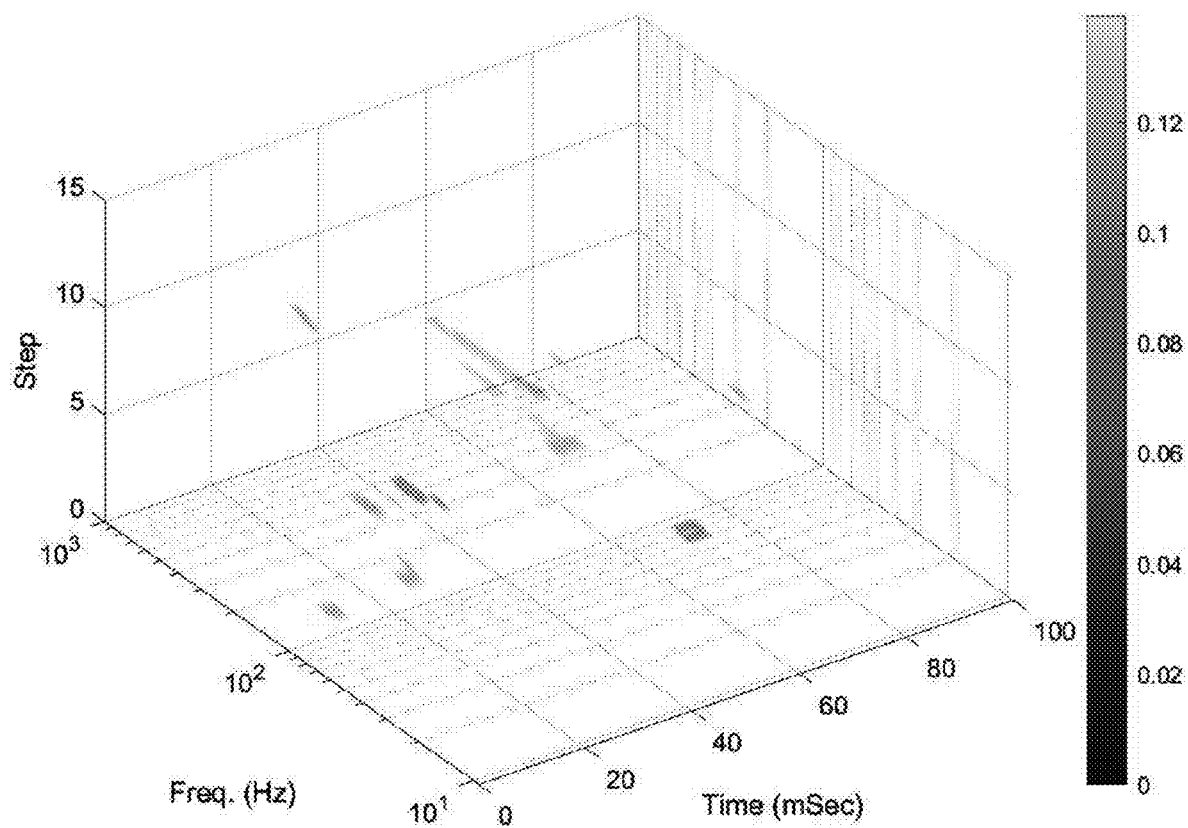

FIG. 32 illustrates most discriminant predictors from features selection (frequency analysis components in the illustrated example) conducted with Principal Component Analysis classification based upon statistical significance at a threshold of statistical p value≤0.05 in patients with bipolar disorder versus patients with major depressive disorder, using a mother wavelet specifically designed with retinal signal datasets from control subjects.

Figure 33:
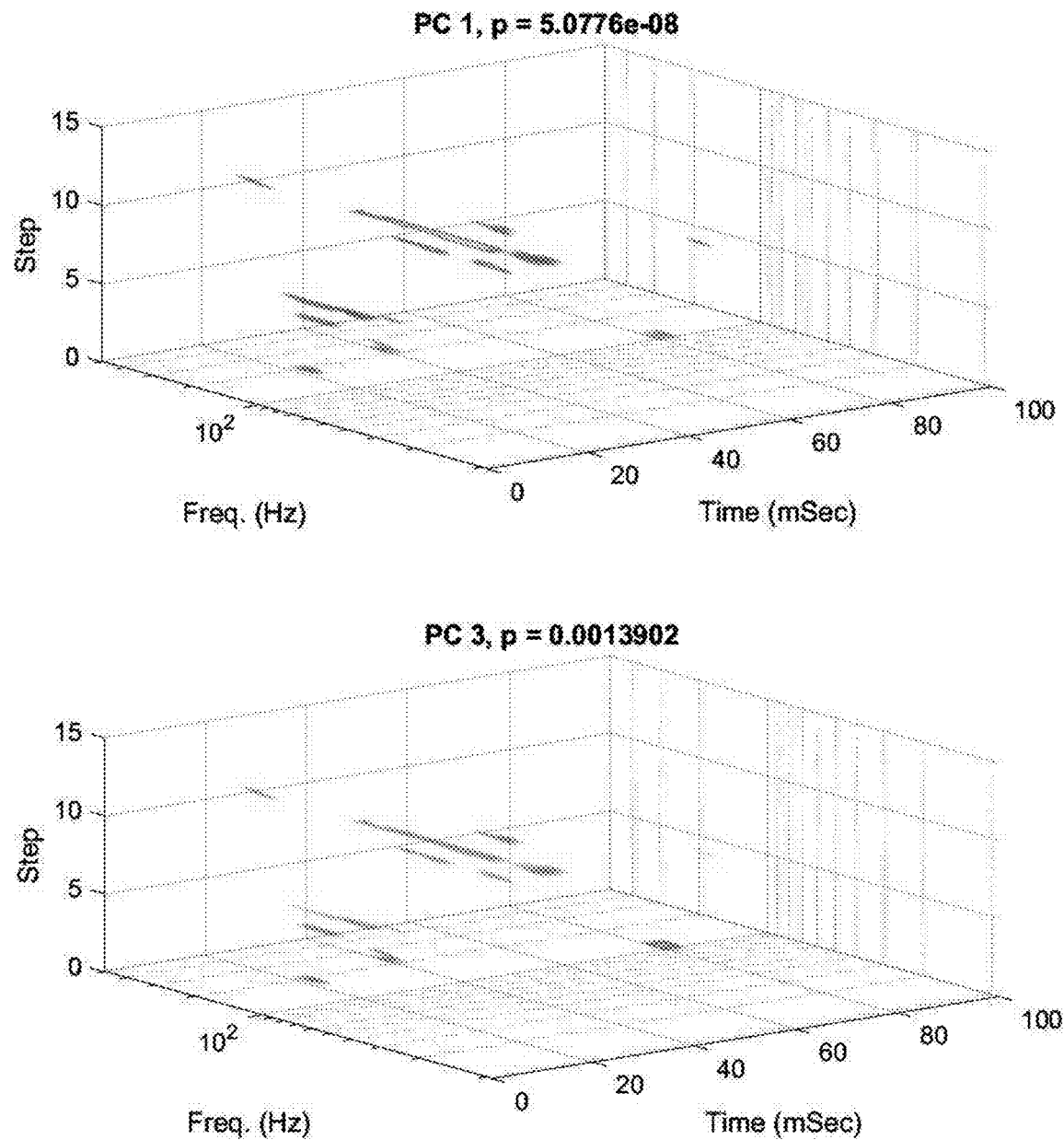

FIG. 33 illustrates mappings of the most discriminant predictors and their levels of significance (statistical p values) from features selection (frequency analysis components in that example) conducted with Principal Component Analysis classification ranked by statistical significance in patients with bipolar disorder versus patients with major depressive disorder, using a mother wavelet specifically designed with retinal signal datasets from control subjects. In the illustrated example, the two most discriminant components were considered at a threshold of p≤0.05. Colors (grey scale) are scales of magnitude of the discriminant power.

Figure 34:
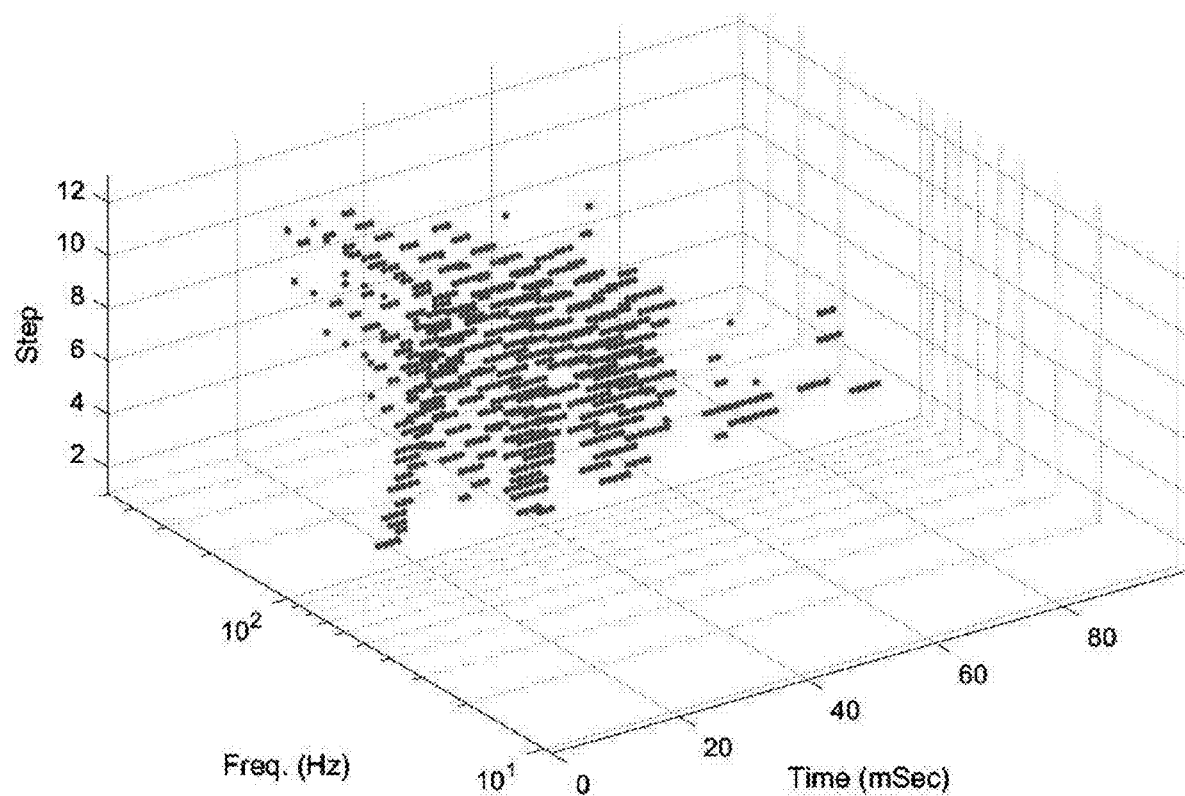

FIG. 34 illustrates most discriminant predictors from features selection (frequency analysis components in this example) conducted with Sparse Representation based Classification (SRC) on wavelet coefficient at a threshold of p≤0.05 in patients with bipolar disorder versus patients at risk of psychoses, using discrete approximation of a mother wavelet specifically designed with retinal signal datasets from control subjects. Colors are scales of magnitude of SRC in a specific position. Red dots (dark dots) are depicting SRC positions with SRC higher than the defined threshold (in the illustrated example, the threshold is from 70% to 100%).

Figure 35:
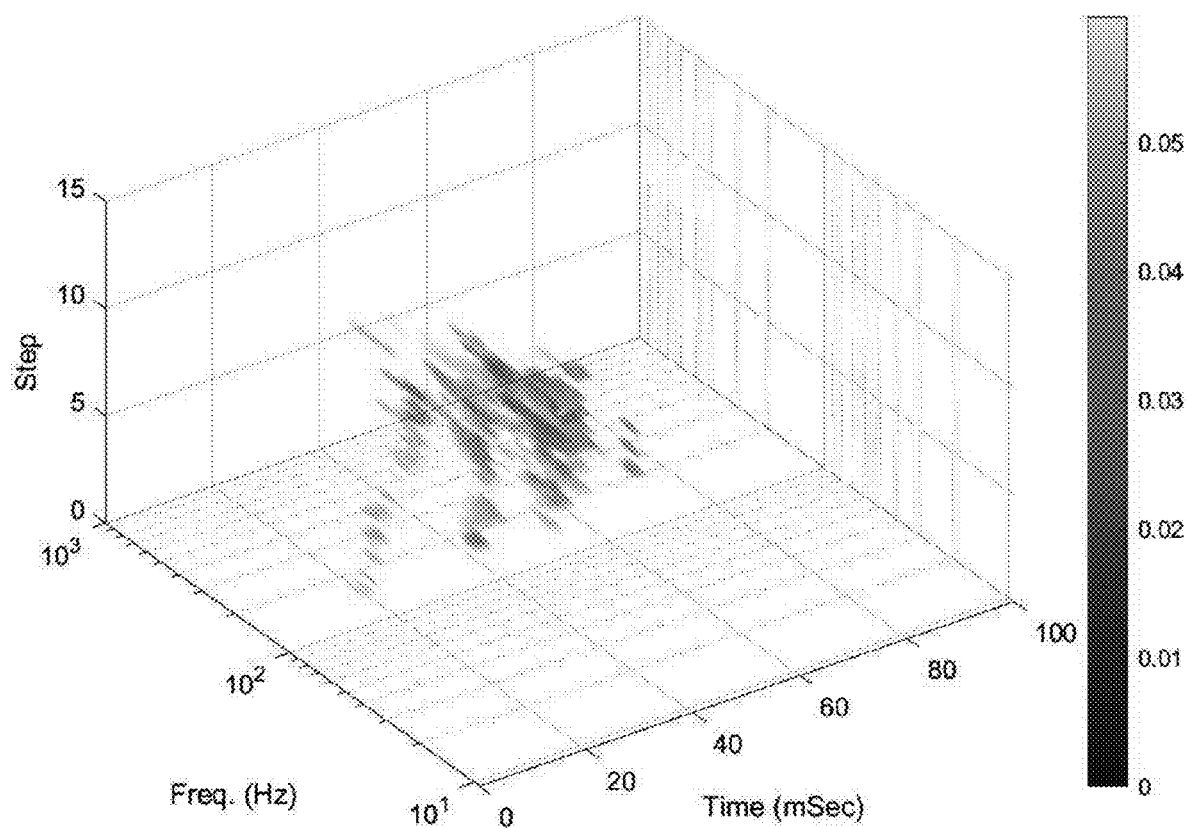

FIG. 35 illustrates most discriminant predictors from features selection (frequency analysis components in that example) conducted with Principal Component Analysis classification based upon statistical significance at a threshold of statistical p value≤0.05 in patients with bipolar disorder versus patients at risk of psychoses, using a mother wavelet specifically designed with retinal signal datasets from control subjects.

Figure 36:
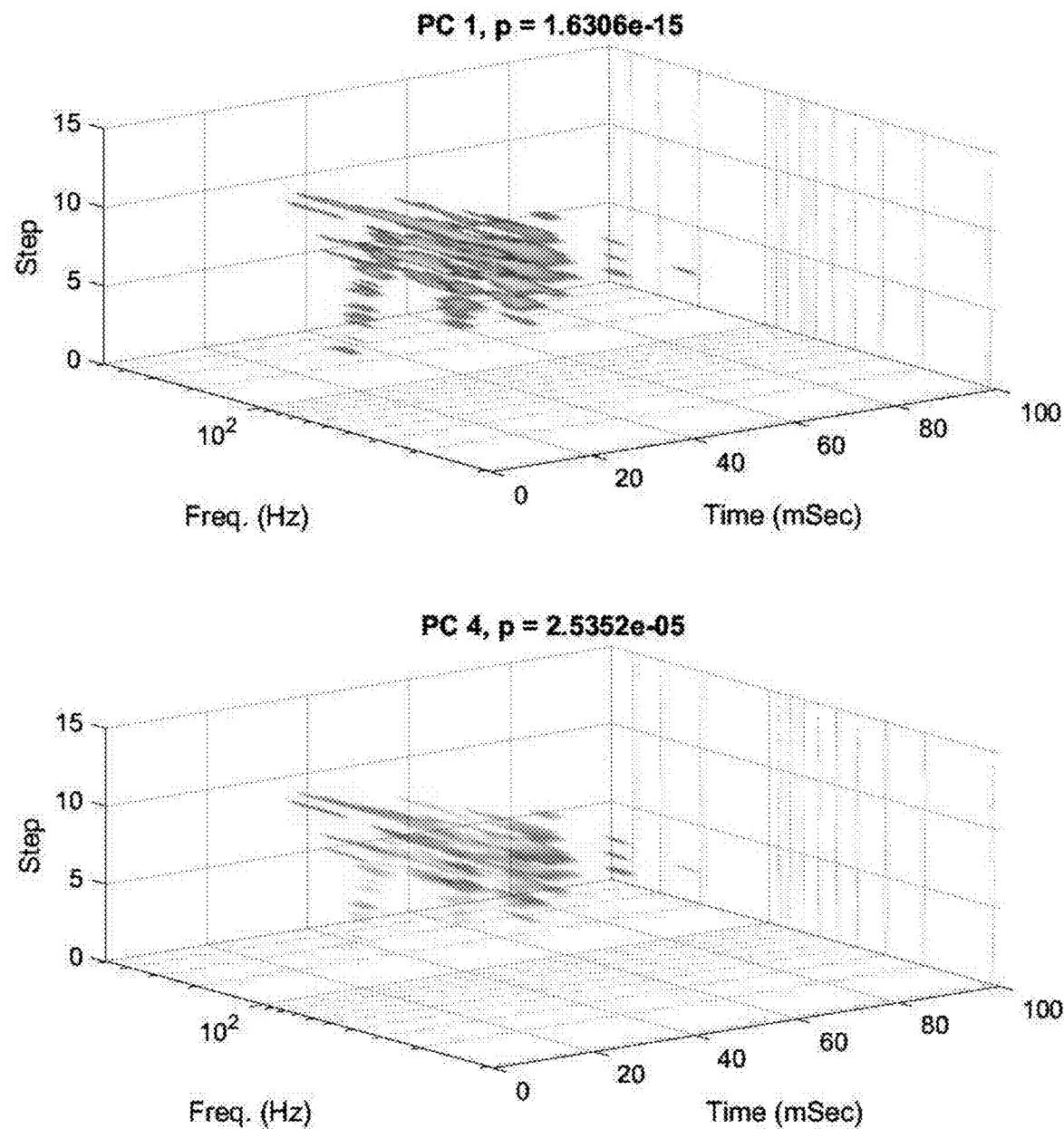

FIG. 36 illustrates mappings of the most discriminant predictors and their levels of significance (statistical p values) from features selection (frequency analysis components in that example) conducted with Principal Component Analysis classification ranked by statistical significance in patients with bipolar disorder versus patients at risk of psychoses, using a mother wavelet specifically designed with retinal signal datasets from control subjects. In the illustrated example, the two most discriminant components were considered at a threshold of p≤0.05. Colors (grey scale) are scales of magnitude of the discriminant power.

Figure 37:
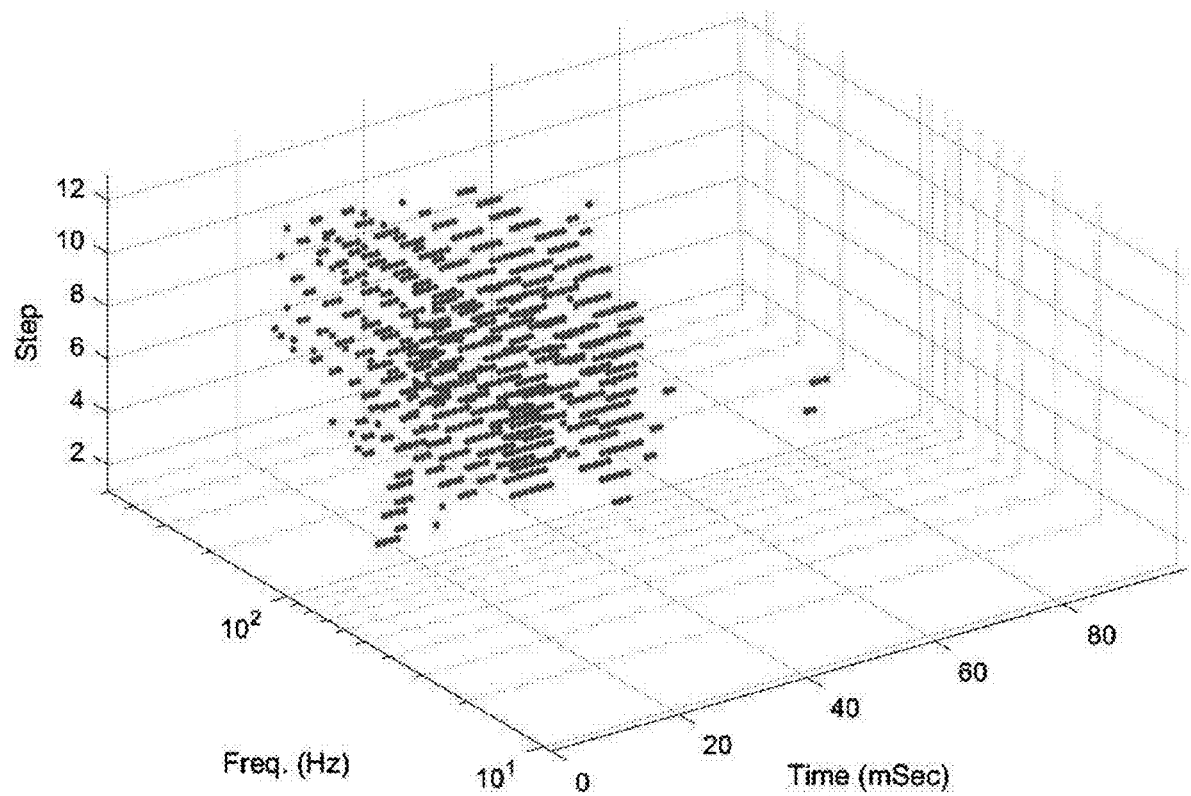

FIG. 37 illustrates most discriminant predictors from features selection (frequency analysis components in that example) conducted with Sparse Representation based Classification (SRC) on wavelet coefficient at a threshold of p≤0.05 in patients with schizophrenia versus patients at risk of psychoses, using discrete approximation of a mother wavelet specifically designed with retinal signal datasets from control subjects. Colors are scales of magnitude of SRC in a specific position. Red dots (dark dots) are depicting SRC positions with SRC higher than the defined threshold (in the illustrated example, the threshold is from 70% to 100%).

Figure 38:
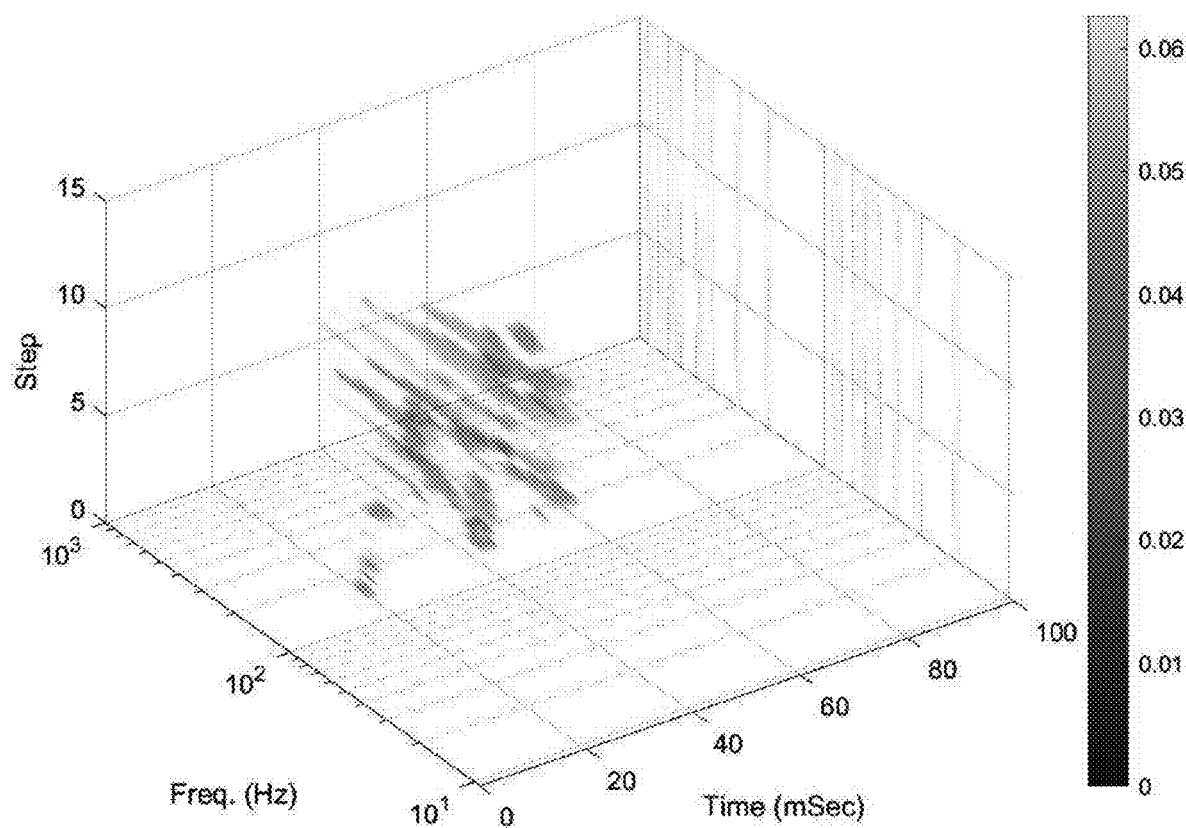

FIG. 38 illustrates most discriminant predictors from features selection (frequency analysis components in that example) conducted with Principal Component Analysis classification based upon statistical significance at a threshold of statistical p value≤0.05 in patients with schizophrenia versus patients at risk of psychoses, using a mother wavelet specifically designed with retinal signal datasets from control subjects.

Figure 39:
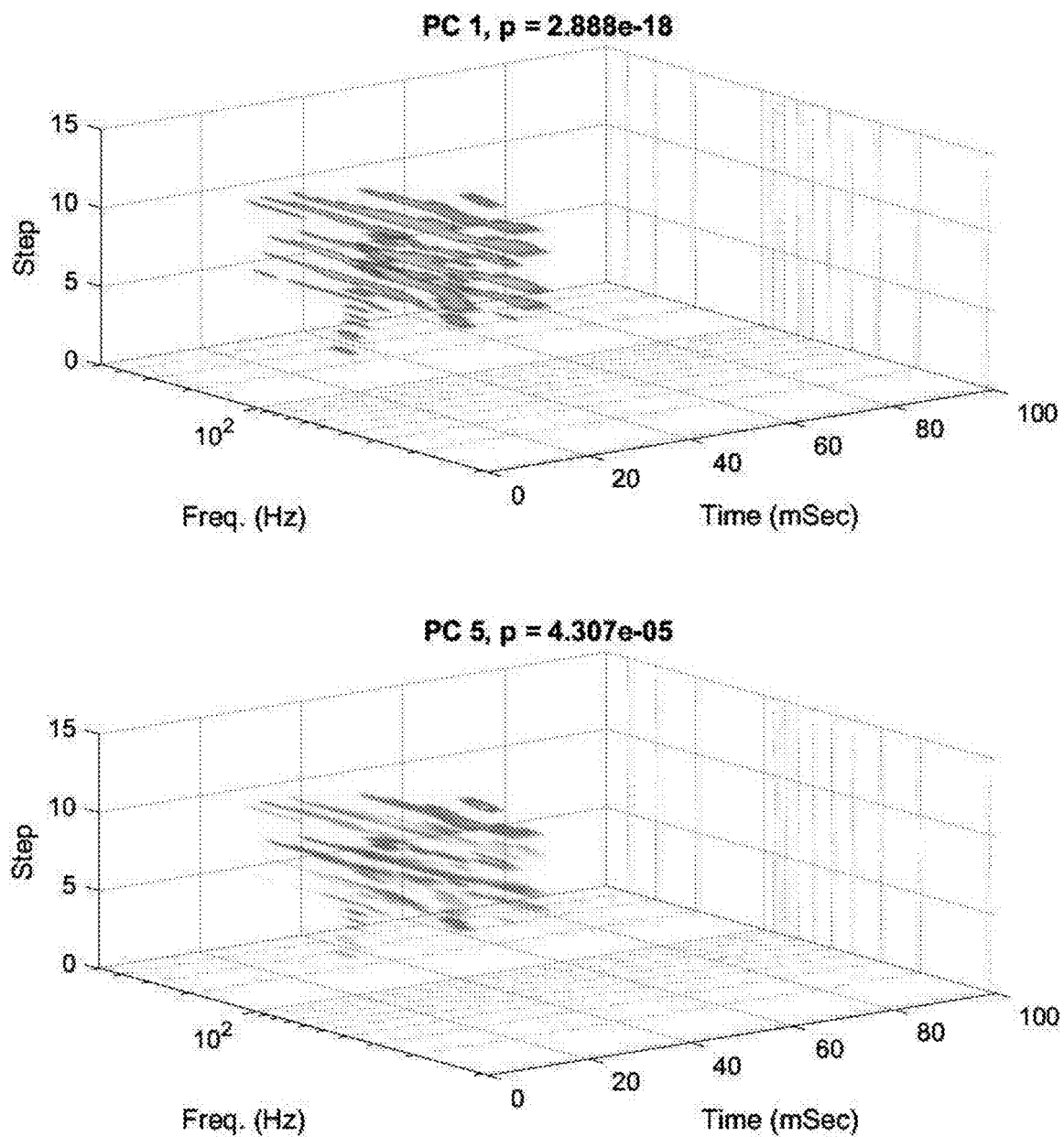

FIG. 39 illustrates mappings of most discriminant predictors and their levels of significance (statistical p values) from features selection (frequency analysis components in that example) conducted with Principal Component Analysis classification ranked by statistical significance in patients with schizophrenia versus patients at risk of psychoses, using a mother wavelet specifically designed with retinal signal datasets from control subjects. In that example, the two most discriminant components were considered at a threshold of p≤0.05. Colors (grey scale) are scales of magnitude of the discriminant power.

Figure 40:
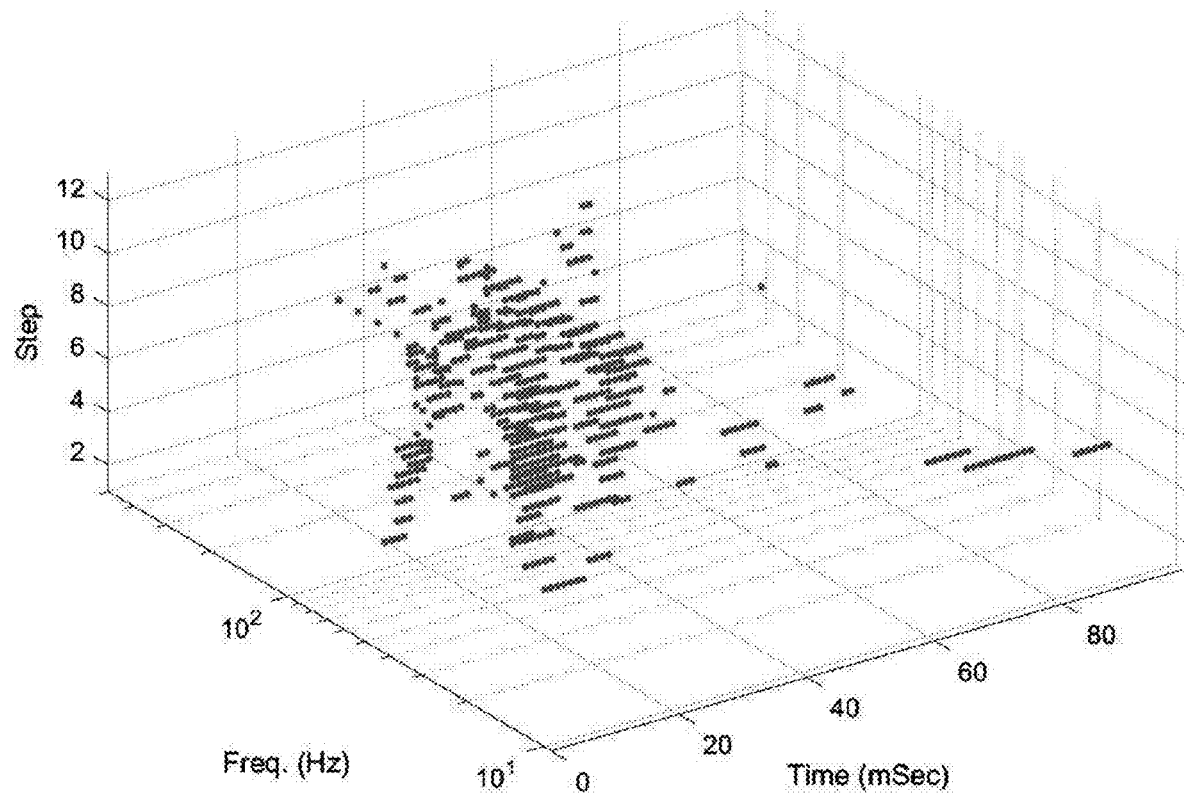

FIG. 40 illustrates most discriminant predictors from features selection (frequency analysis components in that example) conducted with Sparse Representation based Classification (SRC) on wavelet coefficient at a threshold of p≤0.05 in patients with major depressive disorder versus patients at risk of psychoses, using discrete approximation of a mother wavelet specifically designed with retinal signal datasets from control subjects. Colors are scales of magnitude of SRC in a specific position. Red dots (dark dots) are depicting SRC positions with SRC higher than the defined threshold (in the illustrated example, the threshold is from 70% to 100%).

Figure 41:
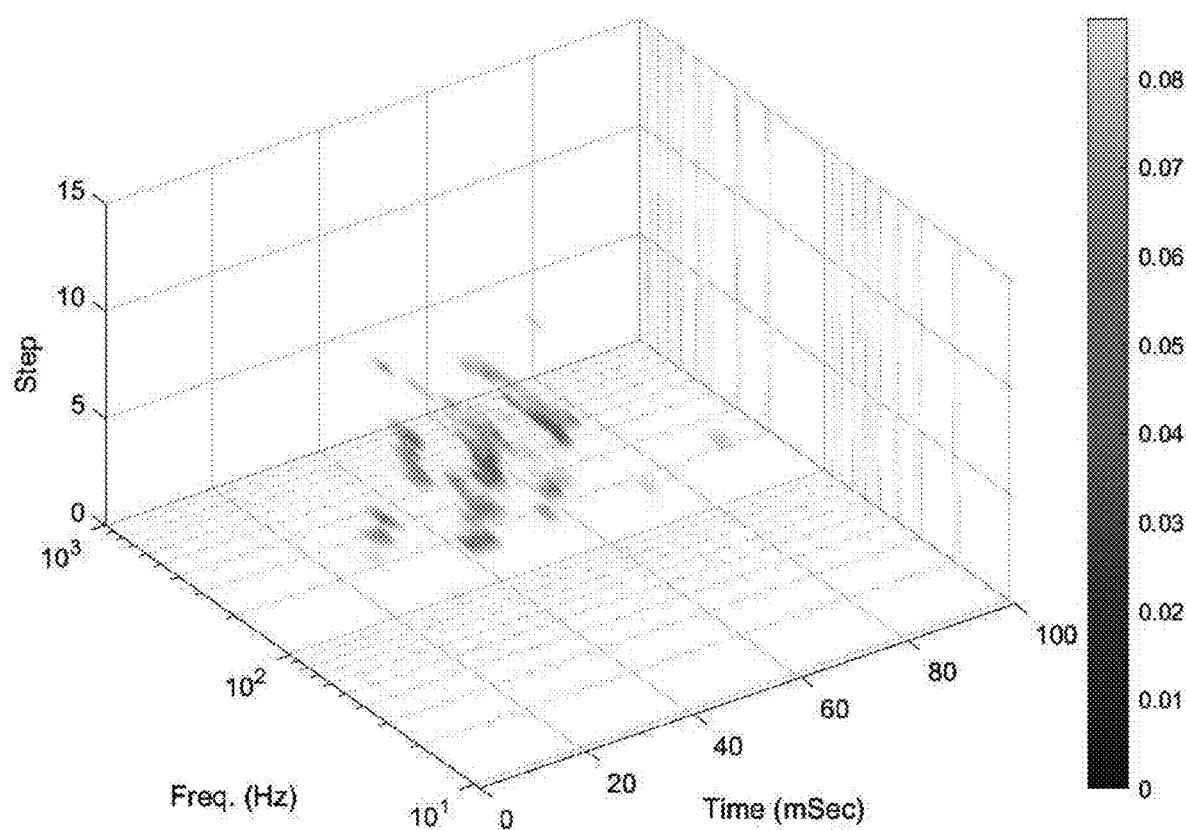

FIG. 41 illustrates most discriminant predictors from features selection (frequency analysis components in the illustrated example) conducted with Principal Component Analysis classification based upon statistical significance at a threshold of statistical p value≤0.05 in patients with major depressive disorder versus patients at risk of psychoses, using a mother wavelet specifically designed with retinal signal datasets from control subjects.

Figure 42:
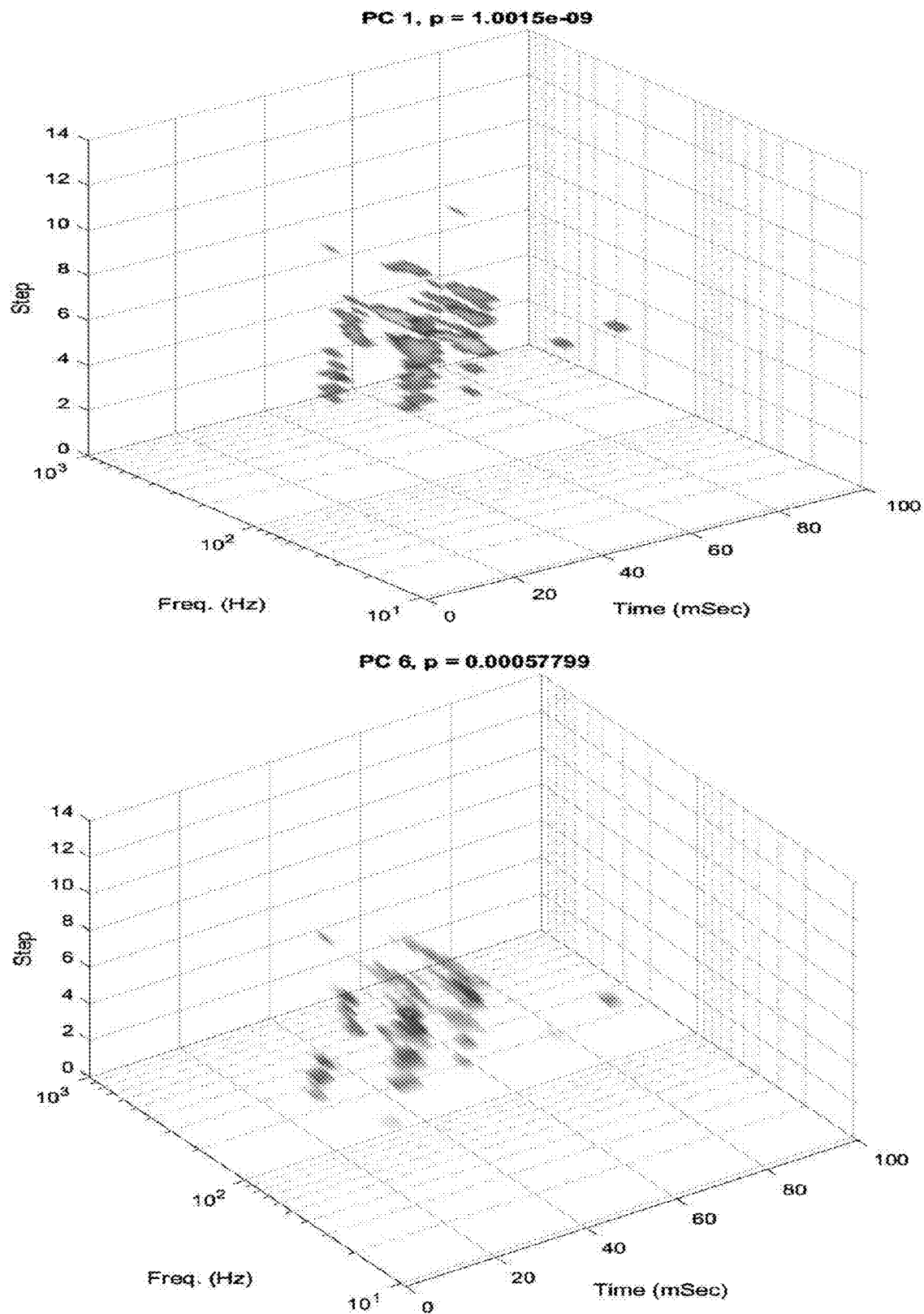

FIG. 42 illustrates mappings of the most discriminant predictors and their levels of significance (statistical p values) from features selection (frequency analysis components in that example) conducted with Principal Component Analysis classification ranked by statistical significance in patients with major depression disorder versus patients at risk of psychoses, using a mother wavelet specifically designed with retinal signal datasets from control subjects. In that example, the two most discriminant components were considered at a threshold of p≤0.05. Colors (grey scale) are scales of magnitude of the discriminant power.

Figure 43:
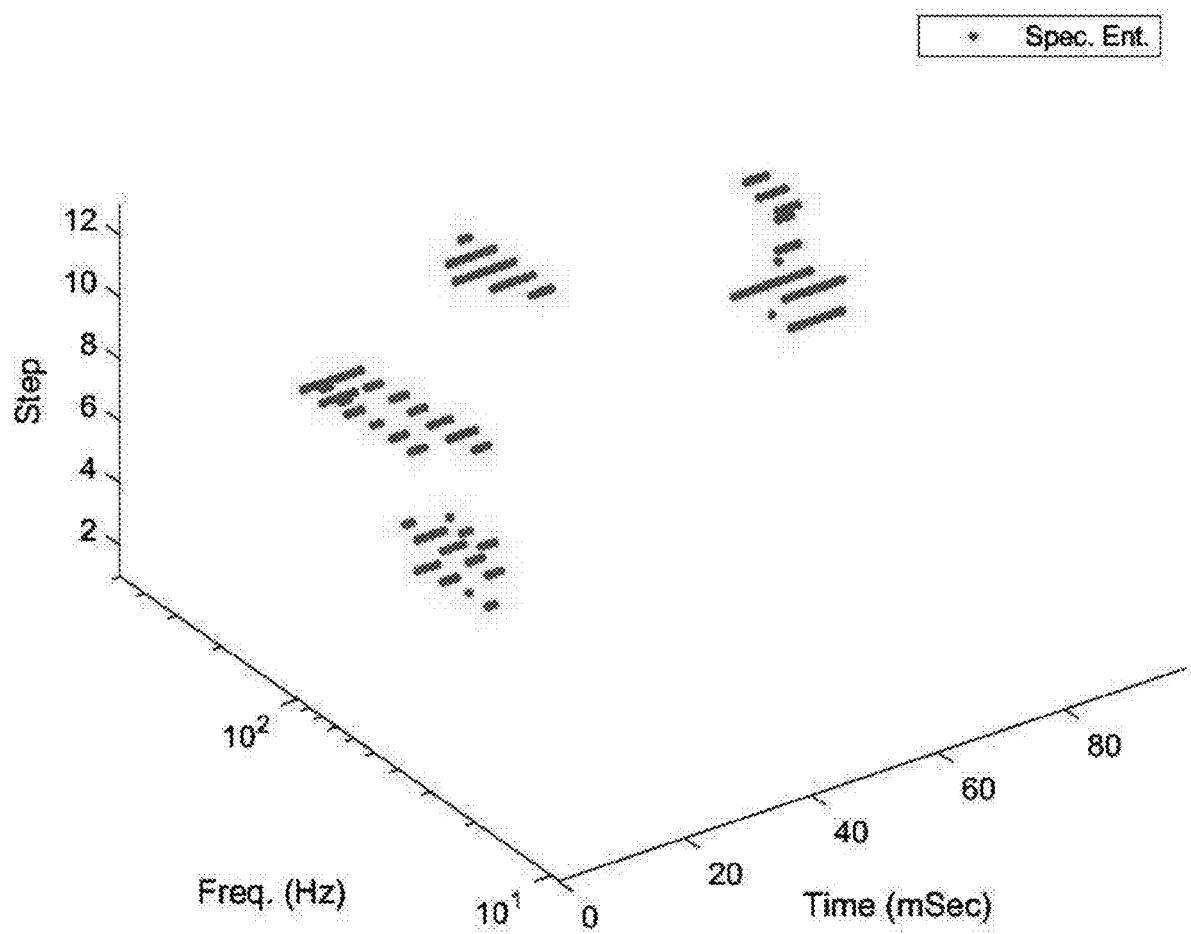
FIGS. 43 to 58 illustrate examples of descriptor selection and mapping based upon the magnitude of discrimination between two conditions, in accordance with various embodiments of the present technology.

FIG. 43 illustrates a mapping of the most discriminant selected descriptors (spectral entropy in that example) conducted with Sparse Representation based Classification (SRC) at a threshold of p≤0.05 in patients at risk of psychoses versus individuals not diagnosed with mental health conditions (control subjects). Red dots (dark dots) are position of higher discriminating power with SRC greater than the defined threshold (in the illustrated example, the threshold is 80%).

Figure 44:
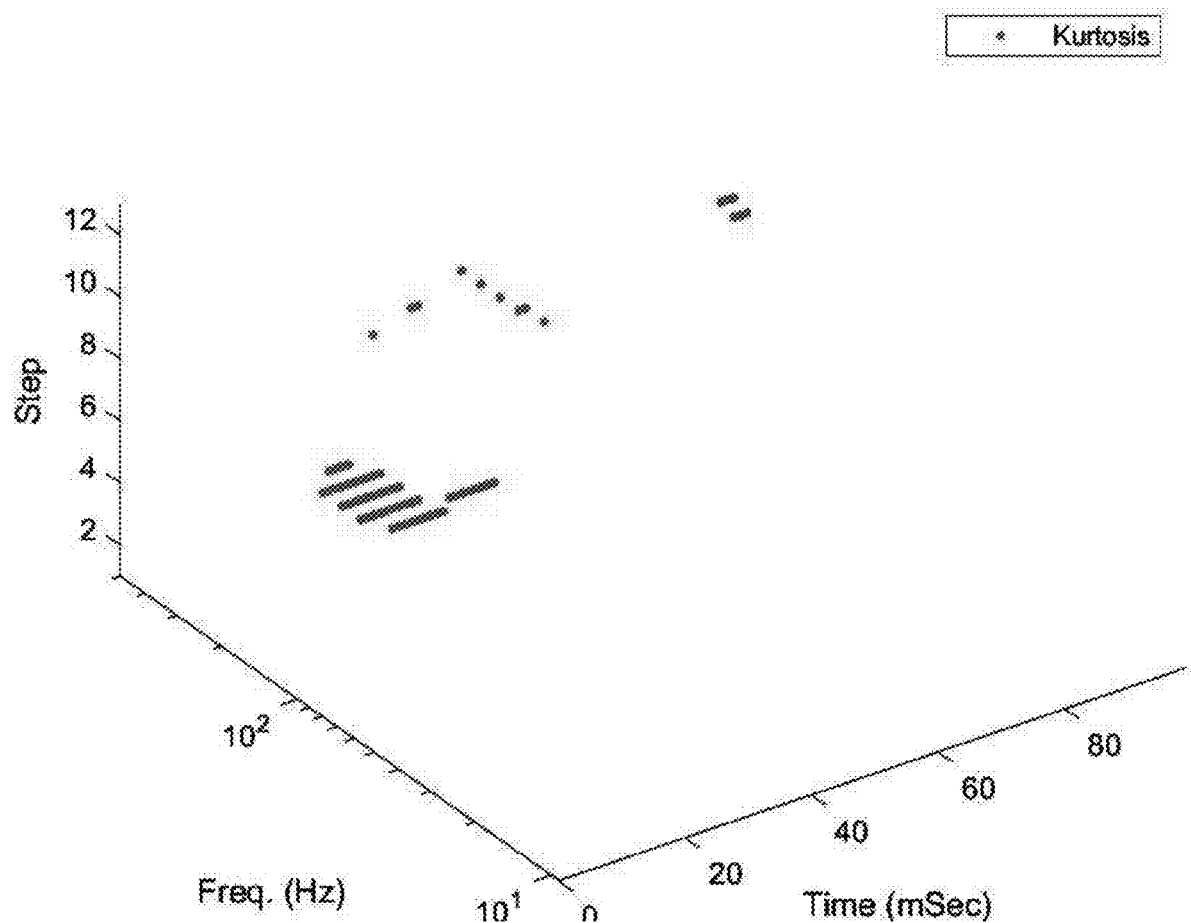

FIG. 44 illustrates a mapping of the most discriminant selected descriptors (kurtosis in the illustrated example) conducted with Sparse Representation based Classification (SRC) at a threshold of p≤0.05 in patients at risk of psychoses versus individuals not diagnosed with mental health conditions (control subjects). Red dots (dark dots) are position of higher discriminating power with SRC greater than the defined threshold (in the illustrated example, the threshold is 80%).

Figure 45:
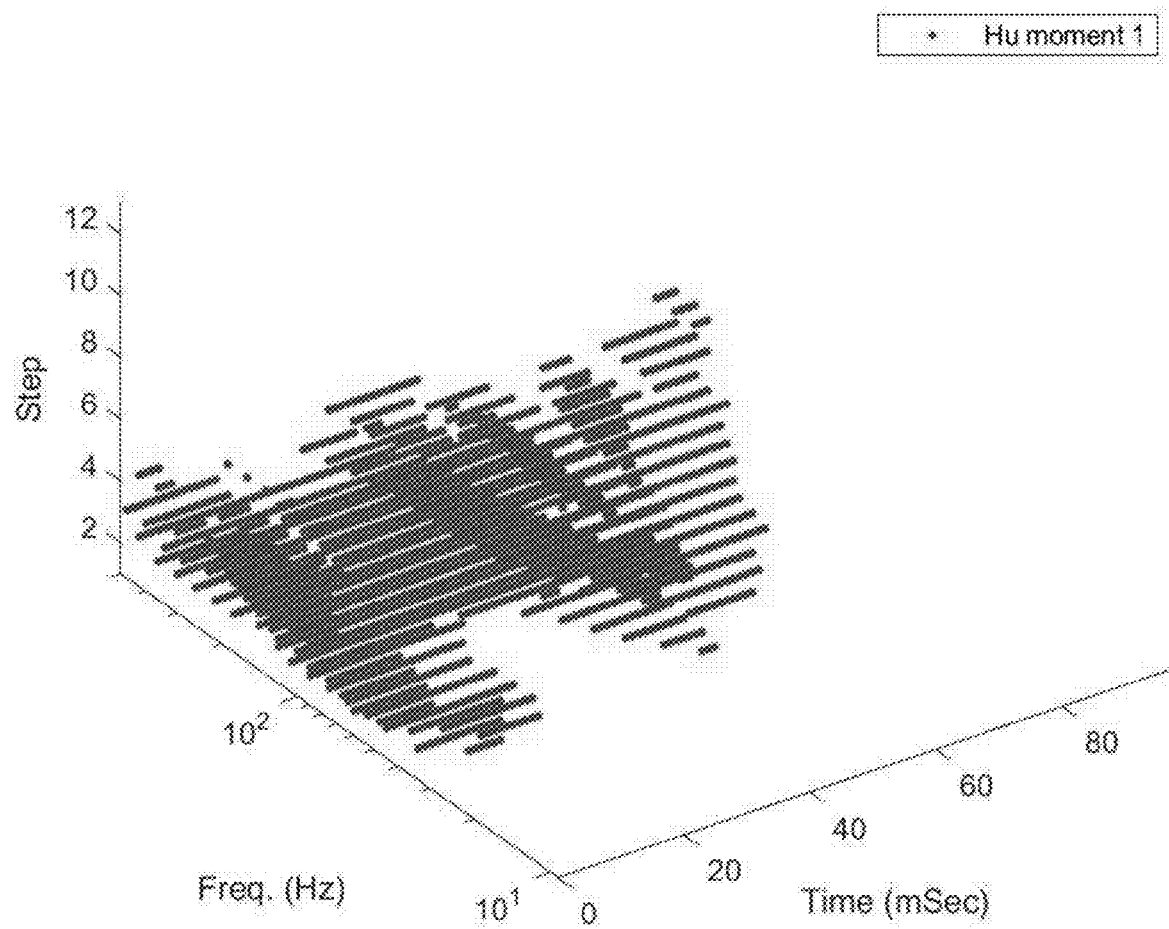

FIG. 45 illustrates a mapping of the most discriminant selected descriptors (Hu moment in that example) conducted with Sparse Representation based Classification (SRC) at a threshold of p≤0.05 in patients at risk of psychoses versus individuals not diagnosed with mental health conditions (control subjects). Red dots (dark dots) are position of higher discriminating power with SRC greater than the defined threshold (in the illustrated example, the threshold is 80%).

Figure 46:
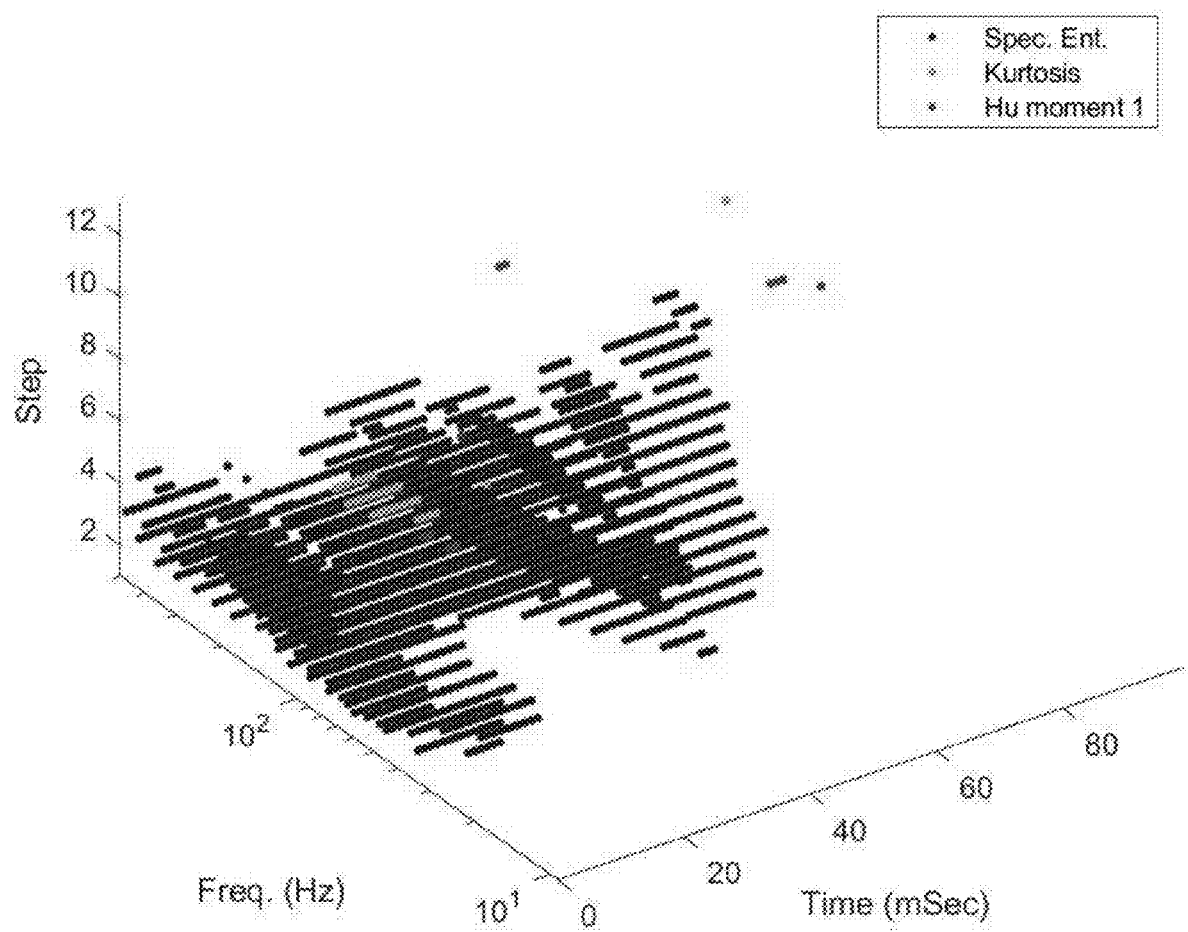

FIG. 46 illustrates a mapping of the most discriminant selected descriptors (Three descriptors in that example: spectral entropy, kurtosis and Hu moment) conducted with Sparse Representation based Classification (SRC) at a threshold of p≤0.05 in patients at risk of psychoses versus individuals not diagnosed with mental health conditions (control subjects). Red dots (dark dots) are position of higher discriminating power with SRC greater than the defined threshold (in the illustrated example, the threshold is 80%). The benefit of additional extractable specific retinal signal descriptors (both in location and statistical significance of the information) is seen when comparing the descriptors with those presented in FIGS. 43, 44 and 45.

Figure 47:
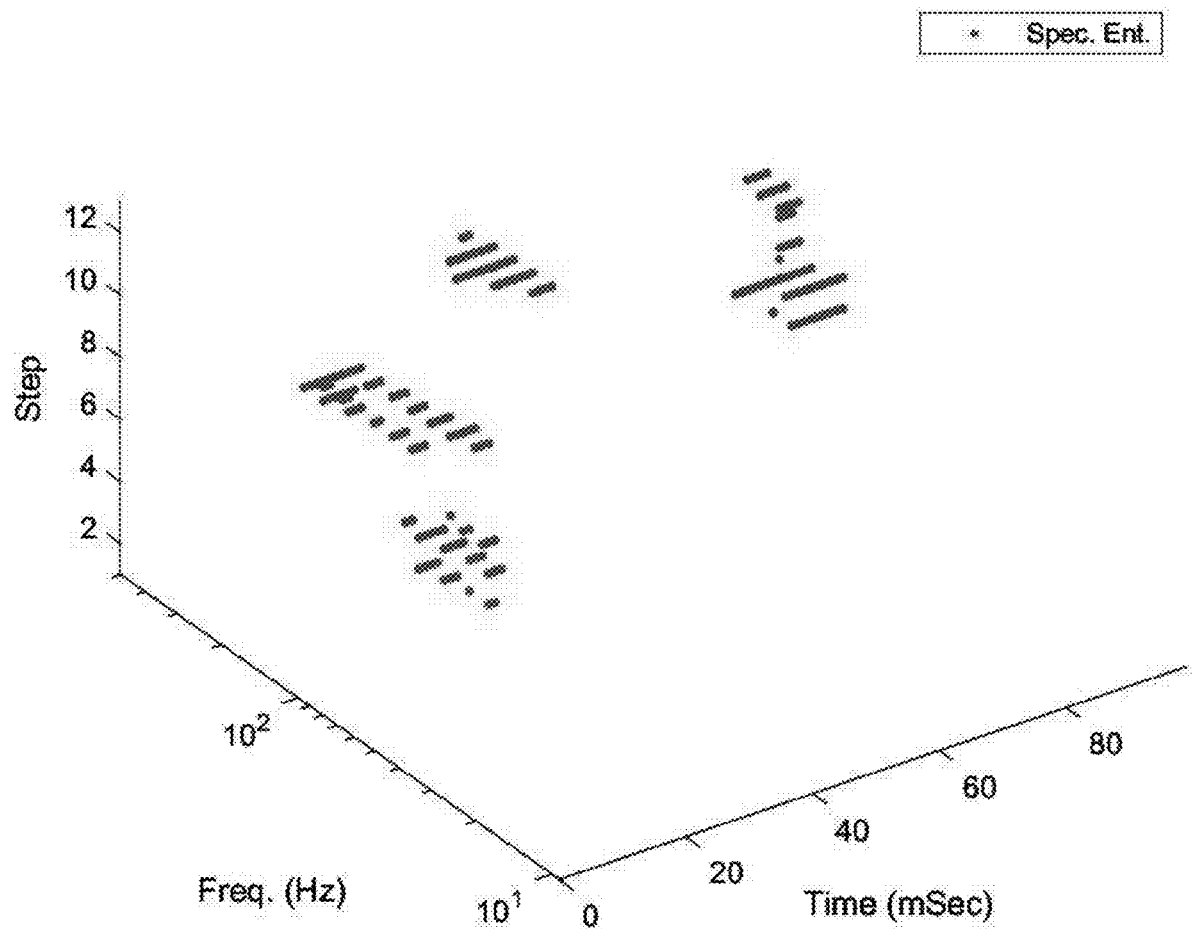

FIG. 47 illustrates a mapping of the most discriminant selected descriptors (spectral entropy in that example) conducted with Sparse Representation based Classification (SRC) at a threshold of p≤0.05 in patients at risk of psychoses versus patients with bipolar disorder. Red dots (dark dots) are position of higher discriminating power with SRC greater than the defined threshold (in the illustrated example, the threshold is 80%).

Figure 48:
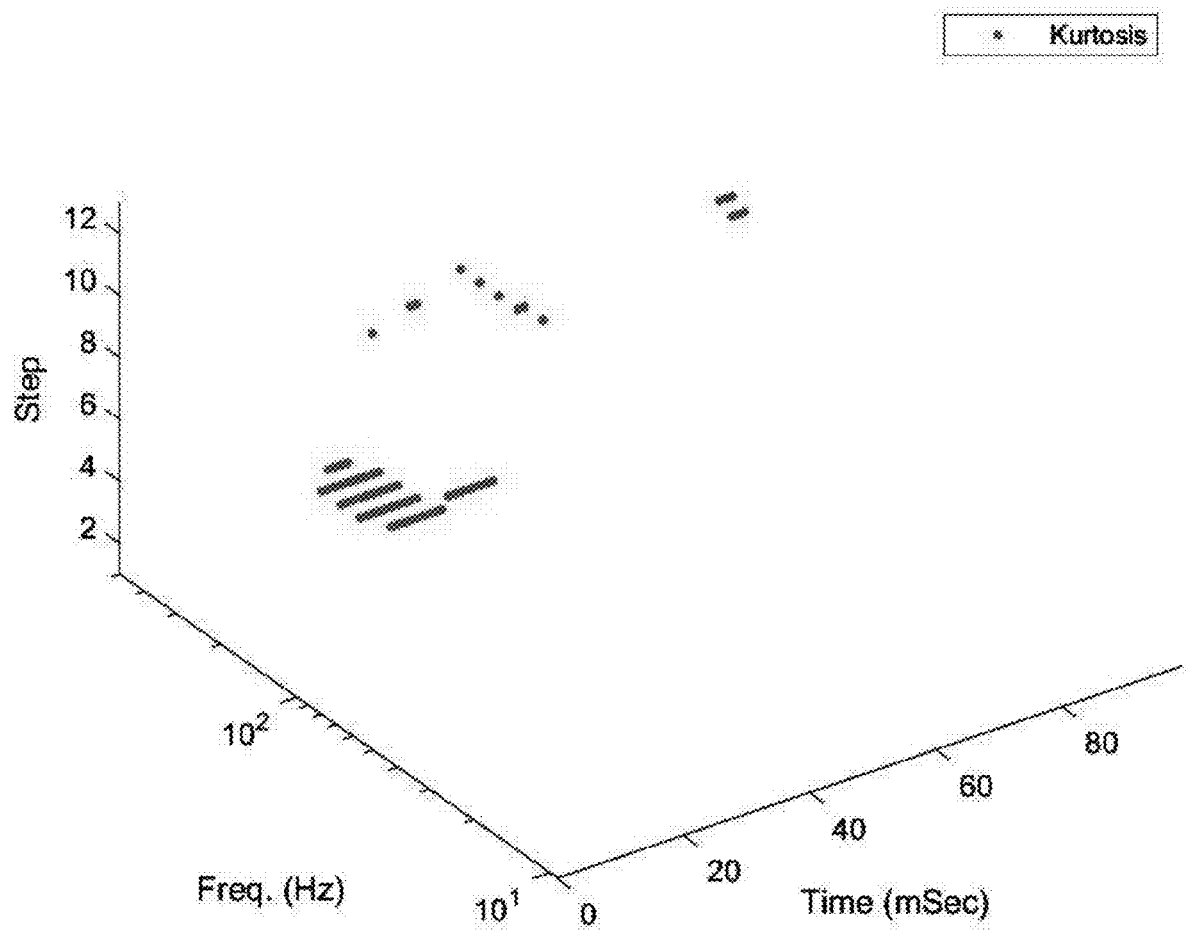

FIG. 48 illustrates a mapping of the most discriminant selected descriptors (kurtosis in that example) conducted with Sparse Representation based Classification (SRC) at a threshold of p≤0.05 in patients at risk of psychoses versus patients with bipolar disorder. Red dots (dark dots) are positions of higher discriminating power with SRC greater than the defined threshold (in the illustrated example, the threshold is 80%).

Figure 49:
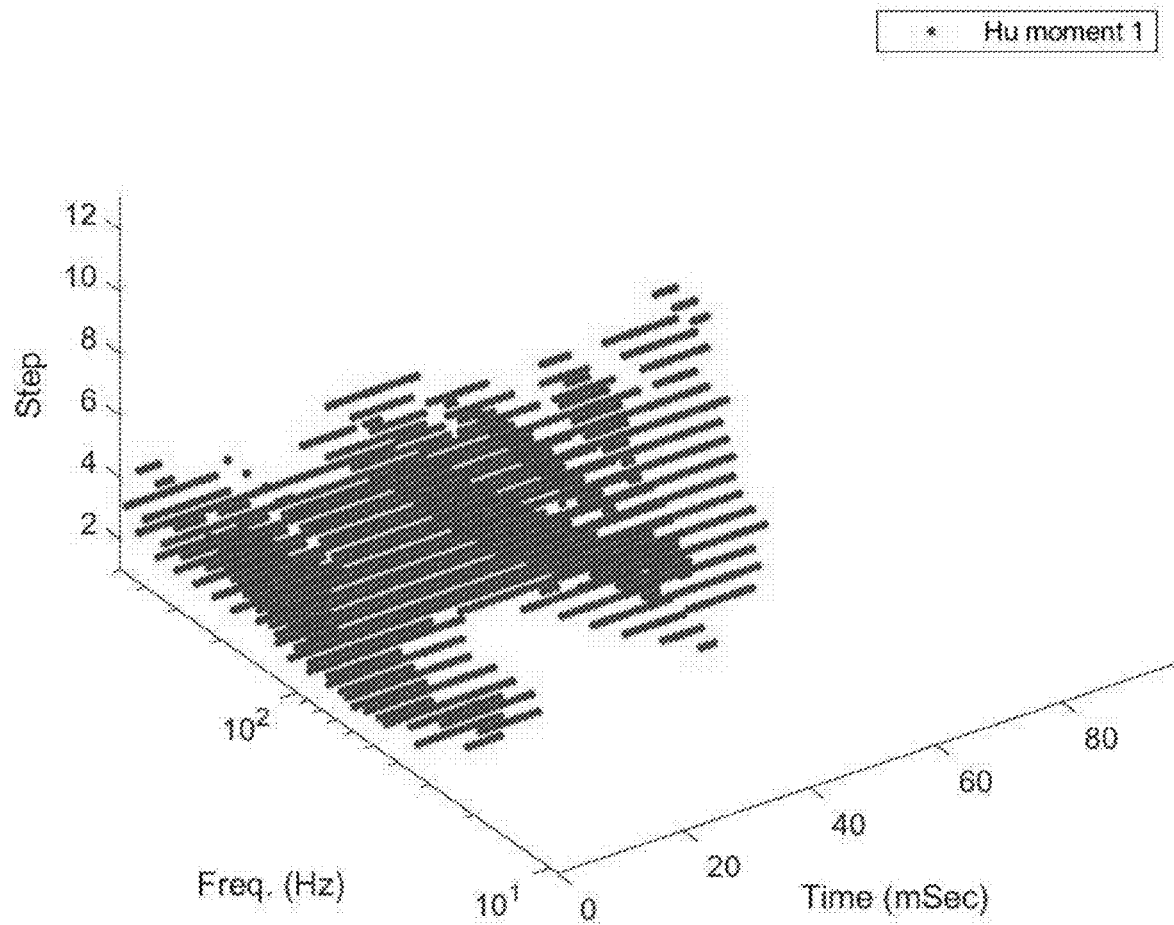

FIG. 49 illustrates a mapping of the most discriminant selected descriptors (Hu moment in this example) conducted with Sparse Representation based Classification (SRC) at a threshold of p≤0.05 in patients at risk of psychoses versus patients with bipolar disorder. Red dots (dark dots) are positions of higher discriminating power with SRC greater than the defined threshold (in the illustrated example, the threshold is 80%).

Figure 50:
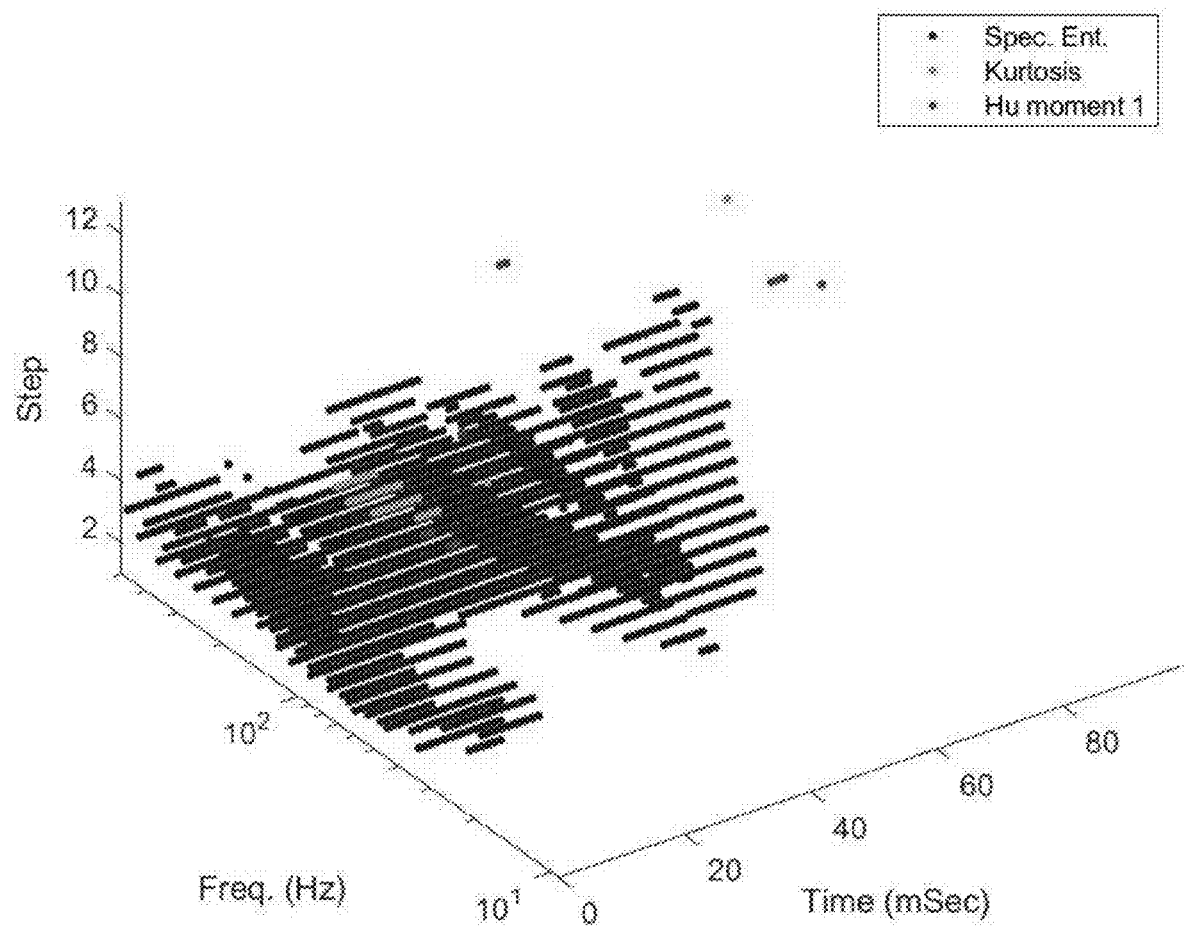

FIG. 50 illustrates a mapping of the most discriminant selected descriptors (three descriptors in this example: spectral entropy, kurtosis and Hu moment) conducted with Sparse Representation based Classification (SRC) at a threshold of p≤0.05 in patients at risk of psychoses versus patients with bipolar disorder. Red dots (dark dots) are positions of higher discriminating power with SRC greater than the defined threshold (in the illustrated example, the threshold is 80%). The benefit of additional extractable specific retinal signal descriptors (both in location and statistical significance of the information) is seen when comparing the descriptors with those presented in FIGS. 47, 48 and 49.

Figure 51:
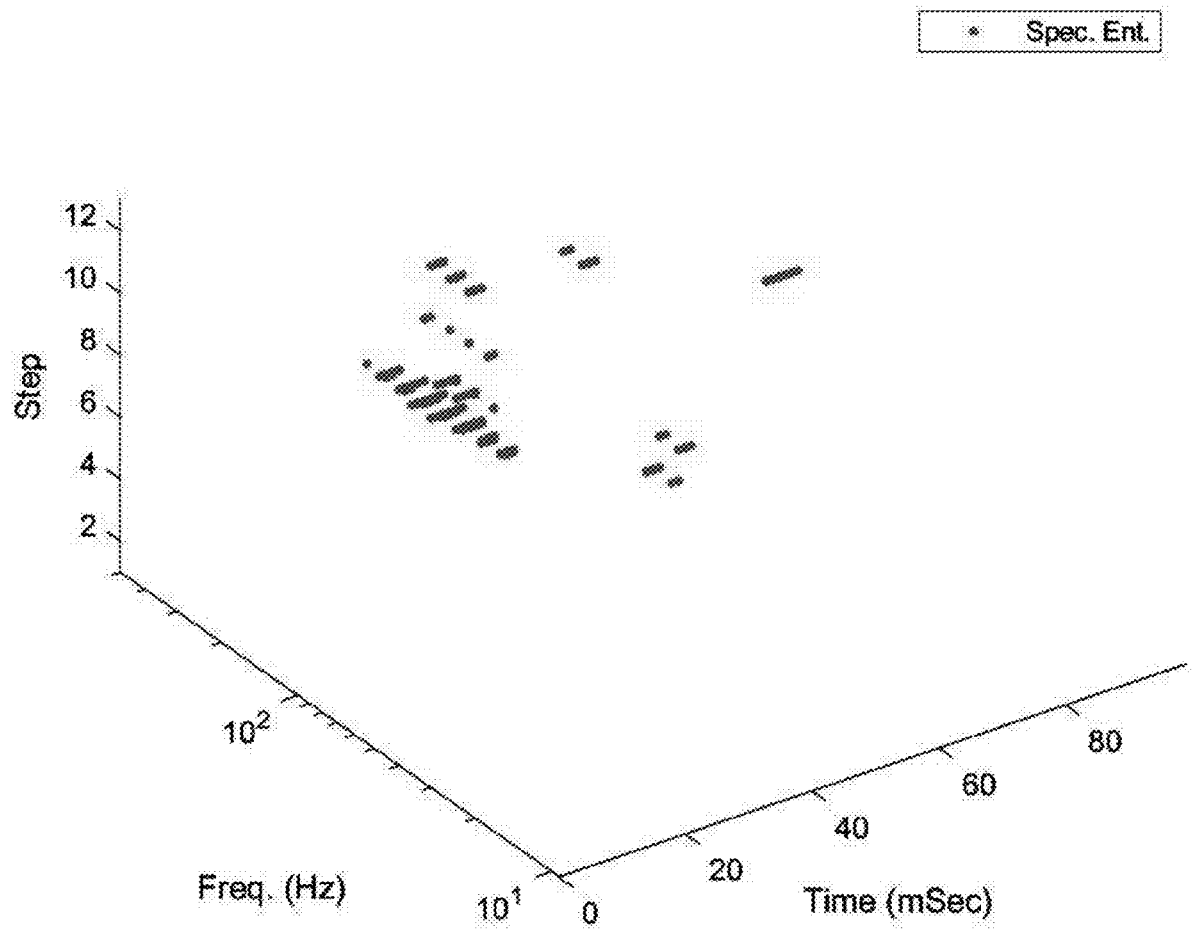

FIG. 51 illustrates a mapping of the most discriminant selected descriptors (spectral entropy in this example) conducted with Sparse Representation based Classification (SRC) at a threshold of p≤0.05 in patients at risk of psychoses versus patients with schizophrenia. Red dots (dark dots) are position of higher discriminating power with SRC greater than the defined threshold (in the illustrated example, the threshold is 80%).

Figure 52:
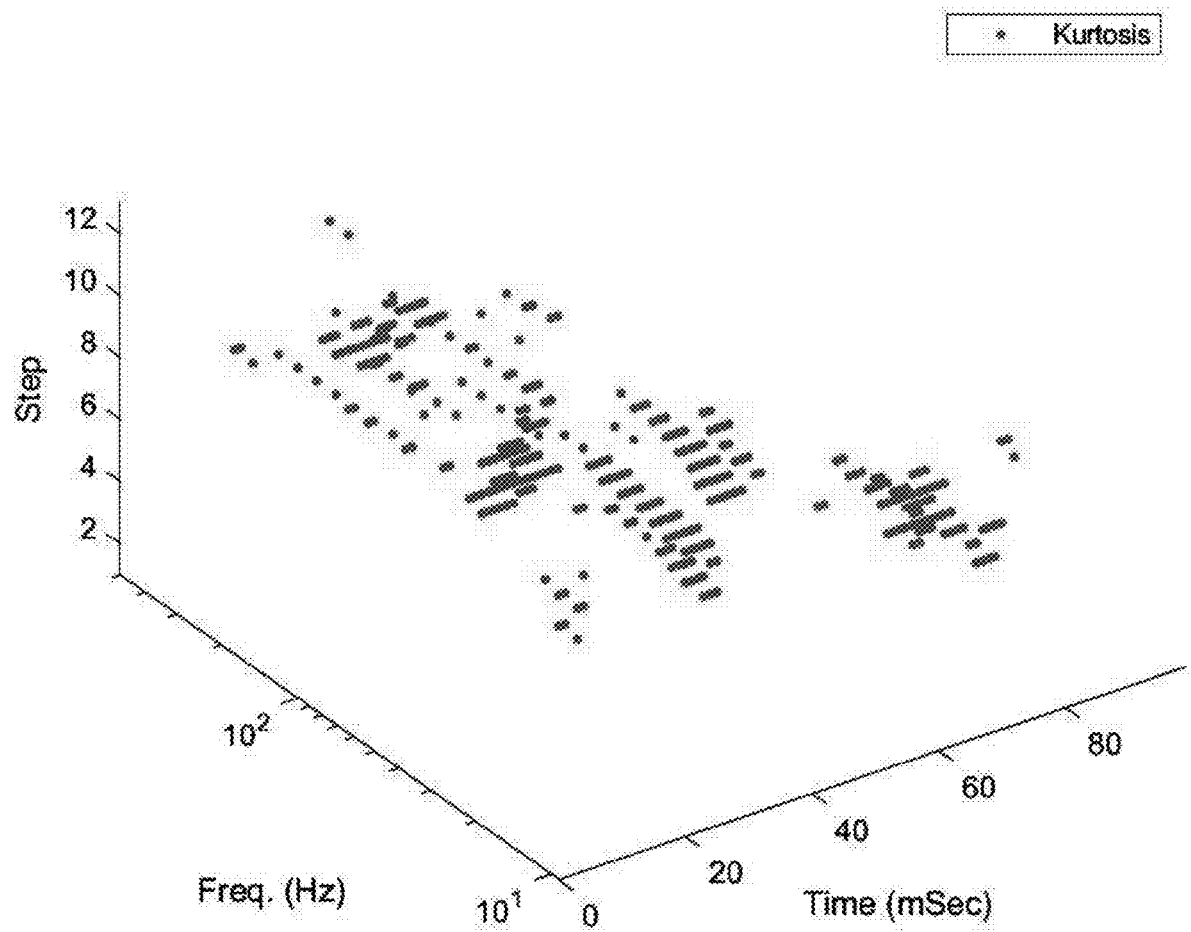

FIG. 52 illustrates a mapping of the most discriminant selected descriptors (kurtosis in that example) conducted with Sparse Representation based Classification (SRC) at a threshold of p≤0.05 in patients at risk of psychoses versus patients with schizophrenia. Red dots (dark dots) are positions of higher discriminating power with SRC greater than the defined threshold (in the illustrated example, the threshold is 80%).

Figure 53:
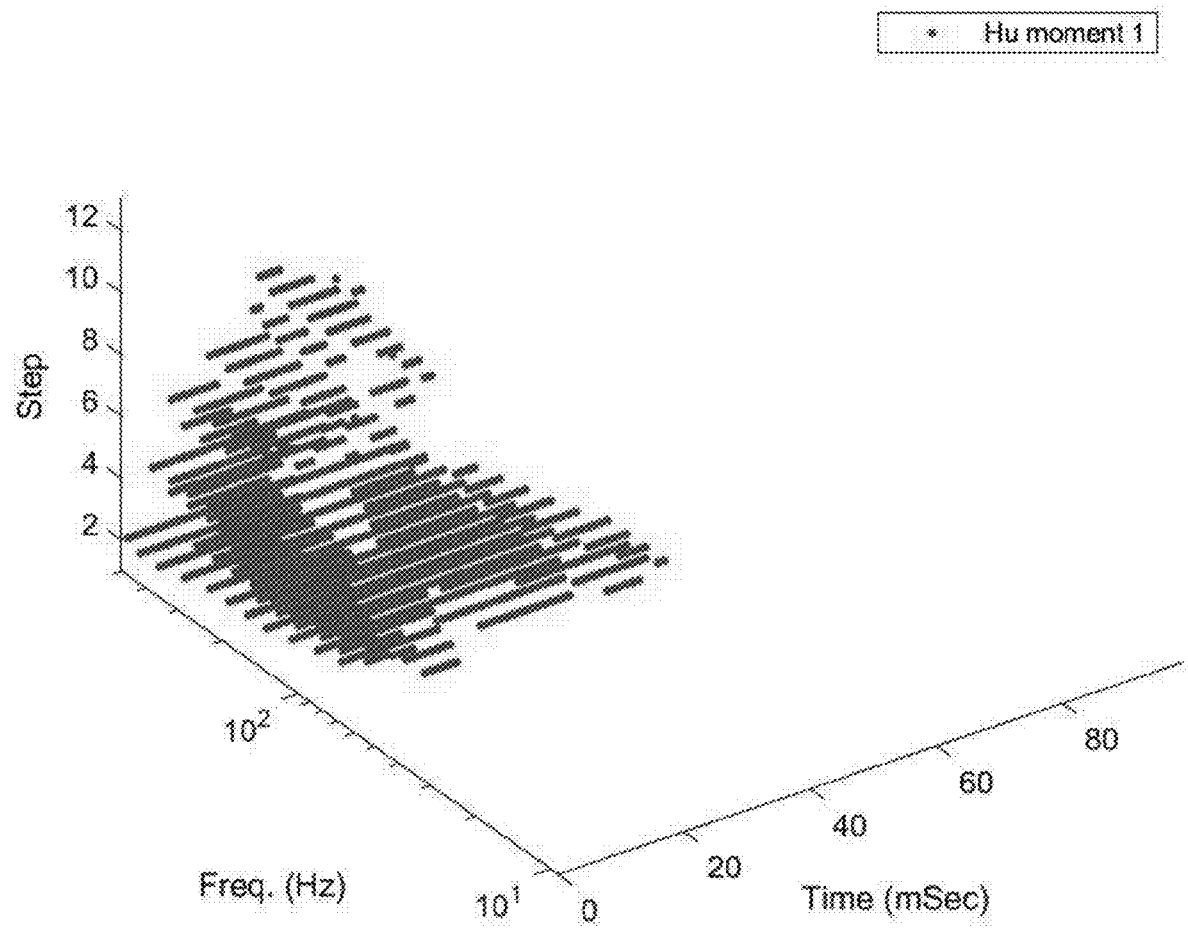

FIG. 53 illustrates a mapping of the most discriminant selected descriptors (Hu moment in this example) conducted with Sparse Representation based Classification (SRC) at a threshold of p≤0.05 in patients at risk of psychoses versus patients with schizophrenia. Red dots (dark dots) are positions of higher discriminating power with SRC greater than the defined threshold (in the illustrated example, the threshold is 80%).

Figure 54:
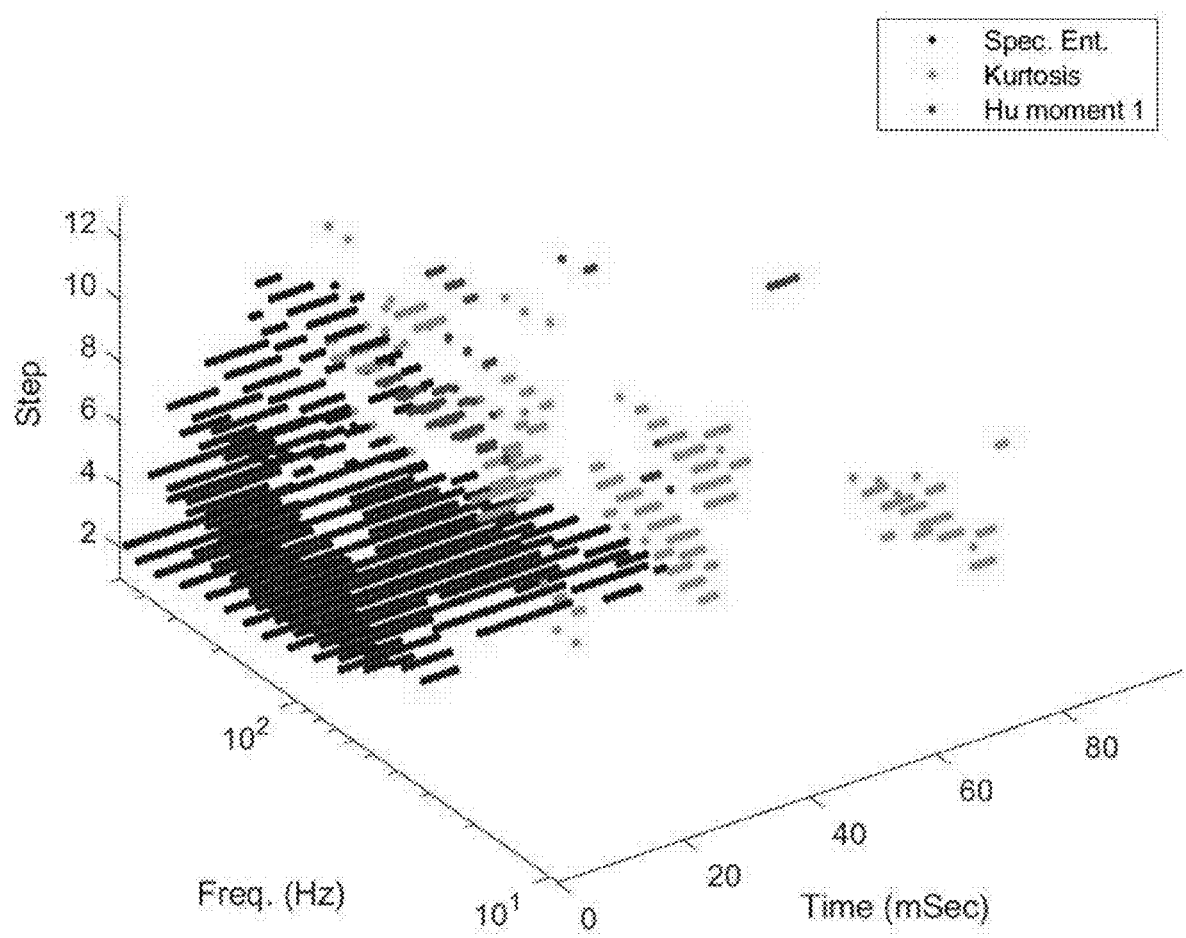

FIG. 54 illustrates a mapping of the most discriminant selected descriptors (three descriptors in this example: spectral entropy, kurtosis and Hu moment) conducted with Sparse Representation based Classification (SRC) at a threshold of p≤0.05 in patients at risk of psychoses versus patients with schizophrenia. Red dots (dark dots) are positions of higher discriminating power with SRC greater than the defined threshold (in the illustrated example, the threshold is 80%). The benefit of additional extractable specific retinal signal descriptors (both in location and statistical significance of the information) is seen when comparing the descriptors with those presented in FIGS. 51, 52 and 53.

Figure 55:
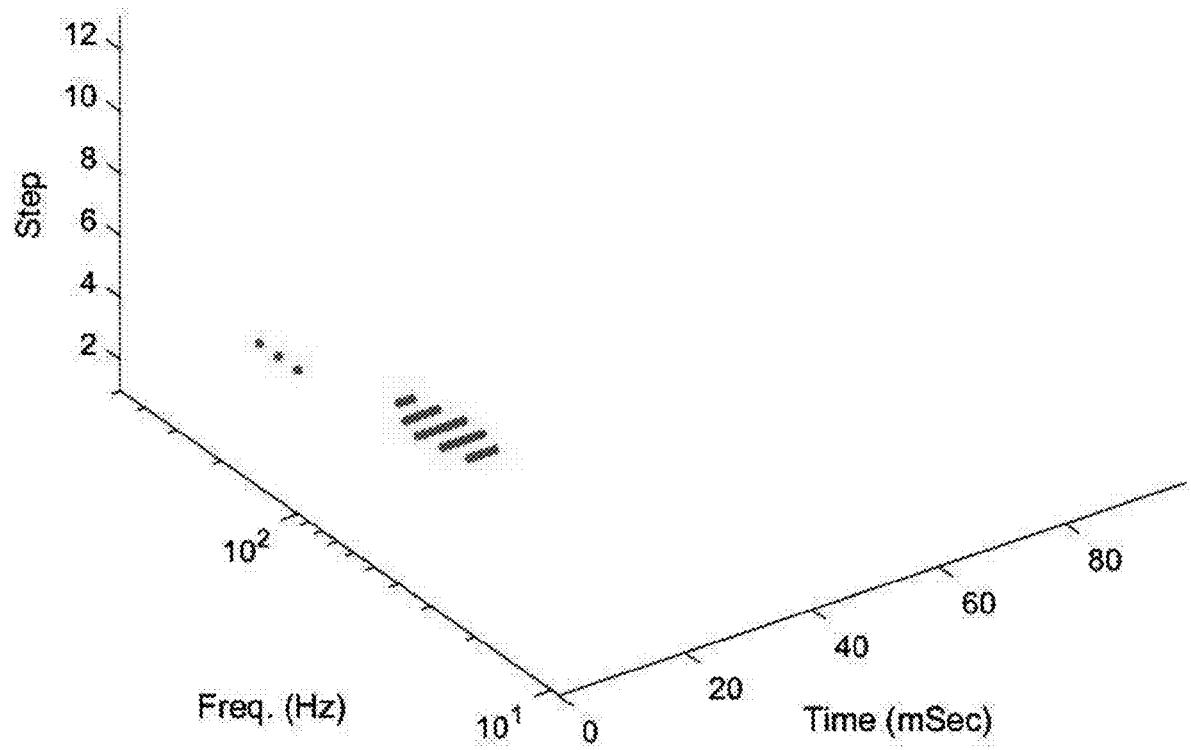

FIG. 55 illustrates a mapping of the most discriminant selected descriptors (spectral entropy in this example) conducted with Sparse Representation based Classification (SRC) at a threshold of p≤0.05 in patients at risk of psychoses versus patients with major depressive disorder. Red dots (dark dots) are positions of higher discriminating power with SRC greater than the defined threshold (in the illustrated example, the threshold is 80%).

Figure 56:
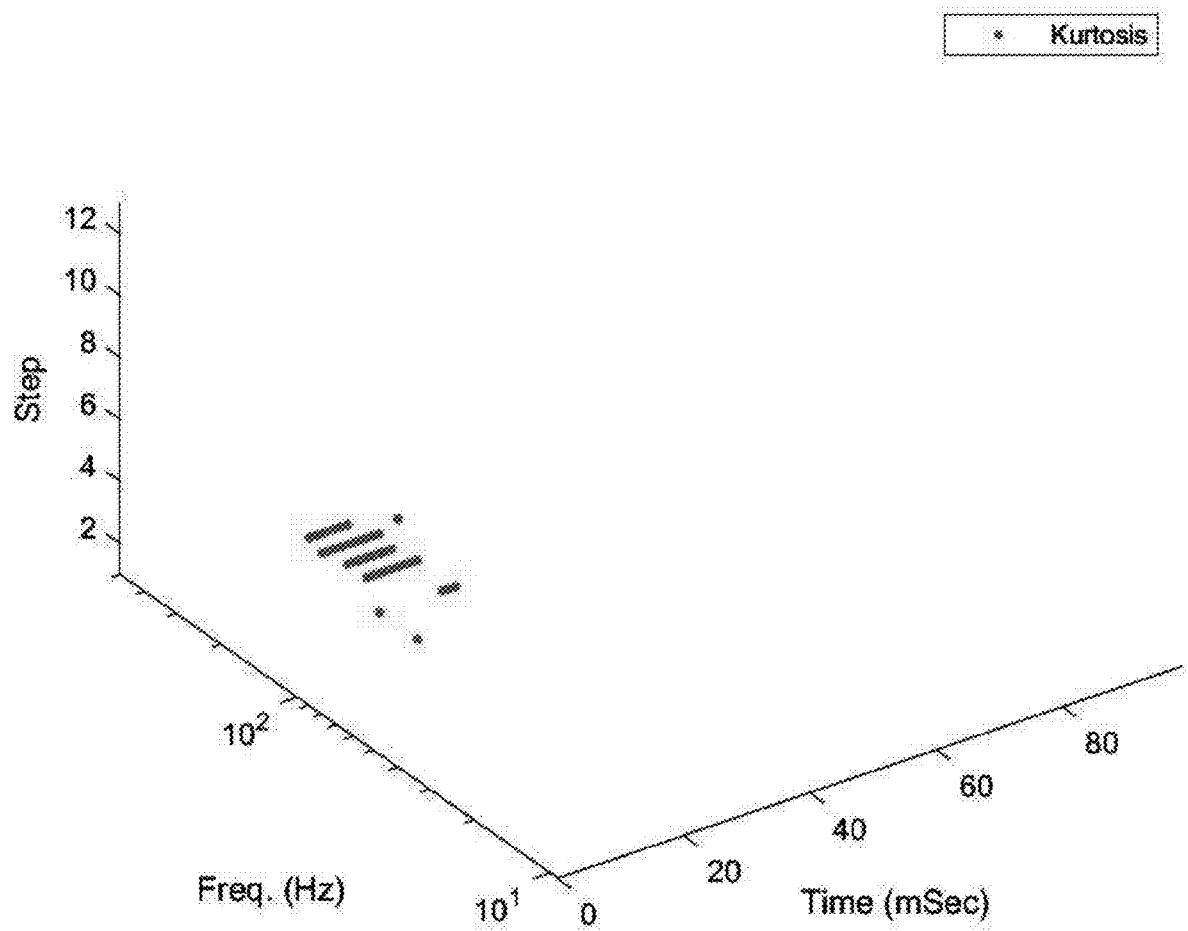

FIG. 56 illustrates a mapping of the most discriminant selected descriptors (kurtosis in this example) conducted with Sparse Representation based Classification (SRC) at a threshold of p≤0.05 in patients at risk of psychoses versus patients with major depressive disorder. Red dots (dark dots) are positions of higher discriminating power with SRC greater than the defined threshold (in the illustrated example, the threshold is 80%).

Figure 57:
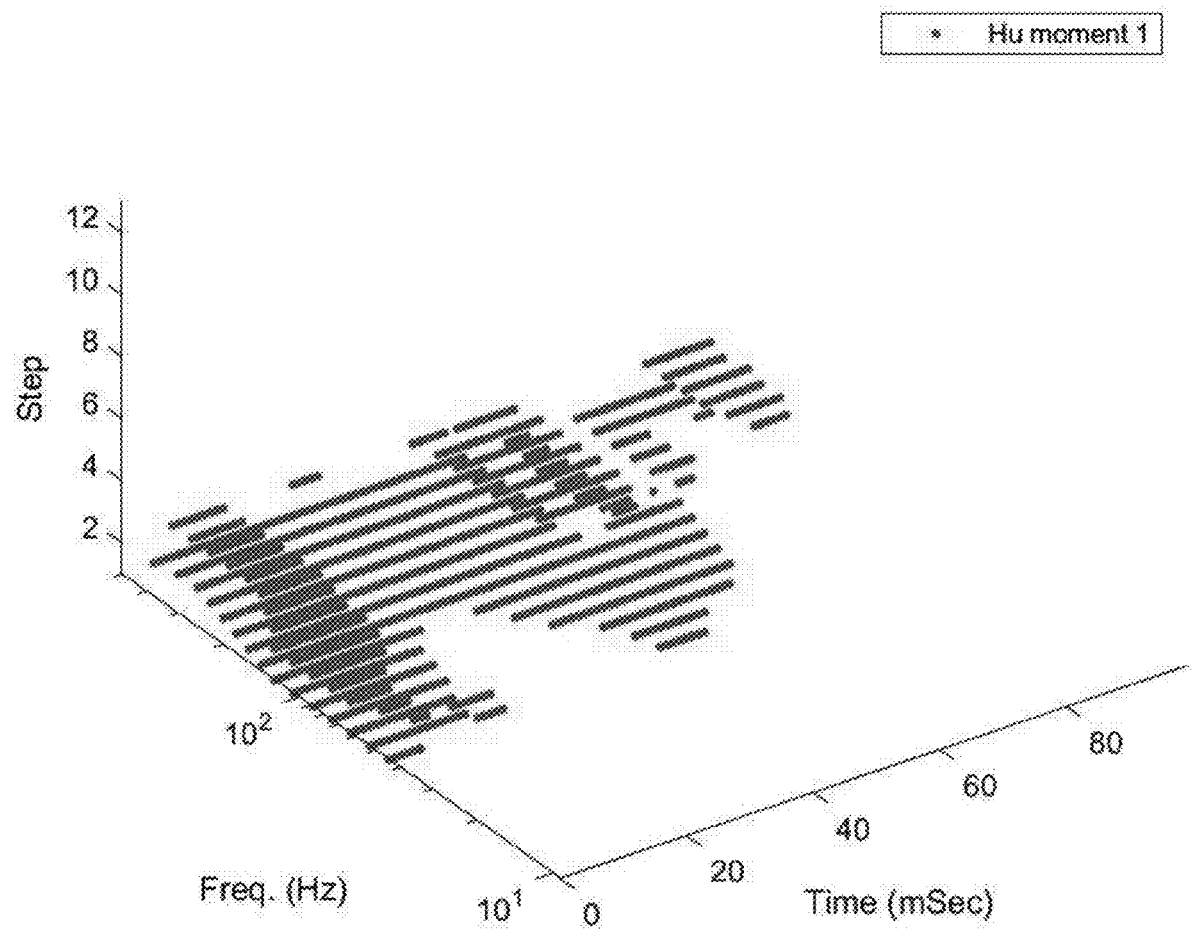

FIG. 57 illustrates a mapping of the most discriminant selected descriptors (Hu moment in this example) conducted with Sparse Representation based Classification (SRC) at a threshold of p≤0.05 in patients at risk of psychoses versus patients with major depressive disorder. Red dots (dark dots) are positions of higher discriminating power with SRC greater than the defined threshold (in the illustrated example, the threshold is 80%).

Figure 58:
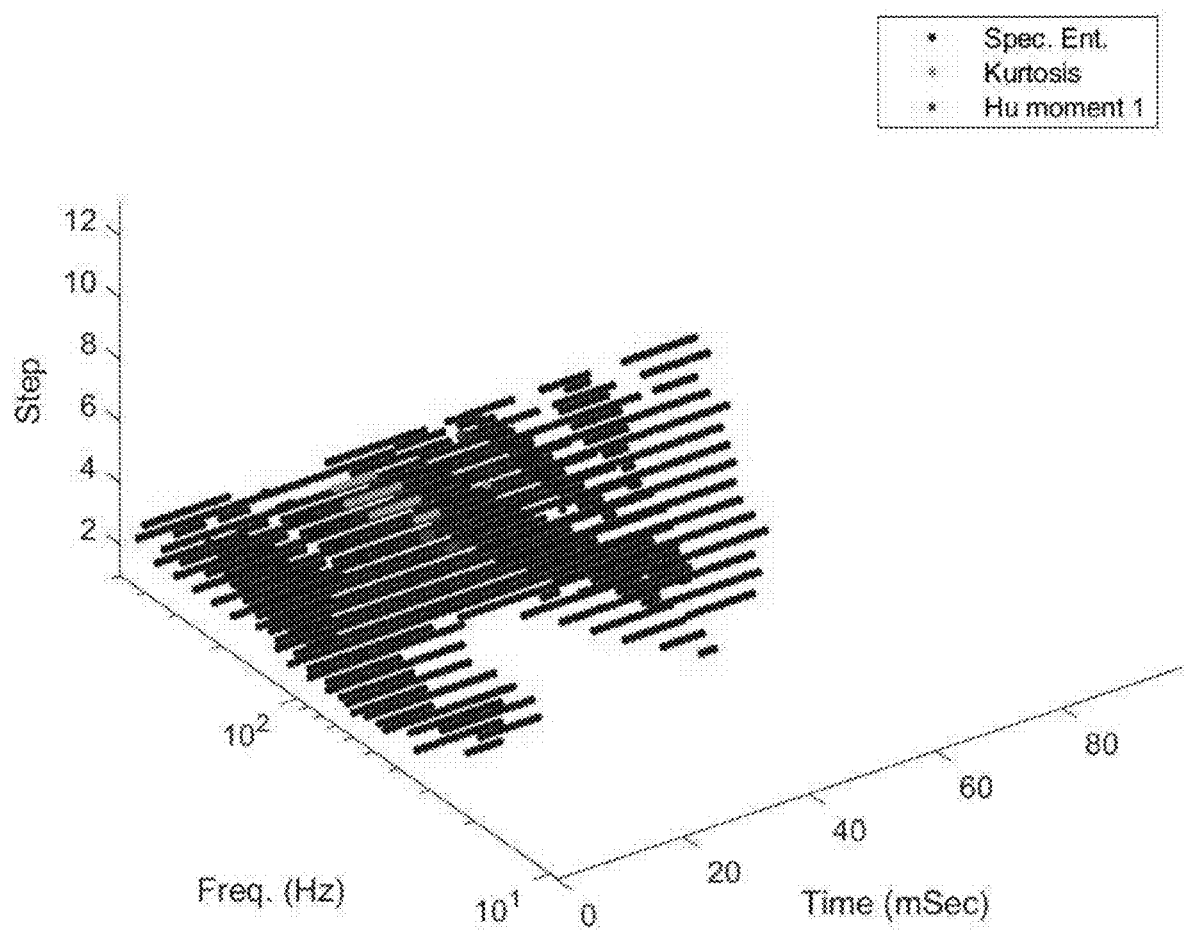

FIG. 58 illustrates a mapping of the most discriminant selected descriptors (three descriptors in that example: spectral entropy, kurtosis and Hu moment) conducted with Sparse Representation based Classification (SRC) at a threshold of p≤0.05 in patients at risk of psychoses versus patients with major depressive disorder. Red dots (dark dots) are positions of higher discriminating power with SRC greater than the defined threshold (in the illustrated example, the threshold is 80%). The benefit of additional extractable specific retinal signal descriptors (both in location and statistical significance of the information) is seen when comparing the descriptors with those presented in FIGS. 55, 56 and 57.

It should be expressly understood that not all technical effects mentioned herein need to be enjoyed in each and every embodiment of the present technology.

Modifications and improvements to the above-described implementations of the present technology may become apparent to those skilled in the art. The foregoing description is intended to be exemplary rather than limiting. The scope of the present technology is therefore intended to be limited solely by the scope of the appended claims.

The invention claimed is:

1. A method for predicting a probability that a human subject is subject to one or more conditions, the method executable by at least one processor of a computer system, the method comprising: receiving retinal signal data corresponding to the human subject, wherein the retinal signal data was collected by an electroretinogram (ERG) system comprising a light stimulator that emits light, at least one electrode for detecting electrical signals, a photodetector for measuring an intensity of the emitted light from the light stimulator, and a spectrometer for measuring a spectrum of the emitted light from the light stimulator, the retinal signal data is associated with a light stimulation of the human subject's retina and includes at least one parameter, recorded by the photodetector or the spectrometer, which is voltage independent and/or time independent, and the retinal signal data was collected for a signal collection time of 200 milliseconds to 500 milliseconds; extracting, from the retinal signal data, one or more retinal signal features; extracting, from the retinal signal features, one or more descriptors; applying the one or more descriptors to a first mathematical model and a second mathematical model, wherein the first mathematical model corresponds to a first condition and the second mathematical model corresponds to a second condition, wherein the first mathematical model and the second mathematical model are machine learning algorithms trained using a sample dataset of retinal signal data including at least one parameter which is voltage independent and/or time independent from subjects with the first condition and the second condition, respectively, thereby generating a first predicted probability for the first condition and a second predicted probability for the second condition and wherein the at least one parameter includes the intensity of the emitted light or the spectrum of the emitted light; and displaying an interface comprising the first predicted probability and the second predicted probability.

2. The method of claim 1, further comprising:
obtaining clinical information cofactors extracted from clinical information corresponding to the human subject; and
applying the clinical information cofactors to the first mathematical model and the second mathematical model.

3. The method of claim 1, wherein the retinal signal data has a sampling frequency between 4 to 24 kHz.

4. The method of claim 1, wherein the retinal signal data comprises an impedance component of a receiving circuit, the impedance component recorded continuously while capturing the retinal signal data.

5. The method of claim 1, wherein the first condition or the second condition is post-traumatic stress disorder, stroke, substance abuse, obsessive compulsive disorder, Alzheimer's, Parkinson's, multiple sclerosis, autism, schizophrenia, bipolar disorder, major depression disorder, psychosis, or attention deficit disorder.

6. The method of claim 1, further comprising receiving user input indicating a selection of the first condition and the second condition.

7. The method of claim 1, further comprising:
selecting, based on the first predicted probability and the second predicted probability, a medication; and
administering the medication to the human subject.

8. The method of claim 1, wherein the retinal signal data comprises circuit impedance, sampling frequency, eye position, frequency of retinal signal sampling, wavelength of illumination, and indications of which retinal areas were illuminated.

9. The method of claim 1, wherein the retinal signal data comprises sampling frequency.

10. The method of claim 1, wherein the retinal signal data comprises eye position.

11. The method of claim 1, wherein the retinal signal data comprises frequency of retinal signal sampling.

12. The method of claim 1, wherein the retinal signal data comprises wavelength of illumination.

13. The method of claim 1, wherein the retinal signal data comprises indications of which retinal areas were illuminated.

14. The method of claim 1, wherein the first mathematical model or the second mathematical model is configured to determine a distance between the descriptors of the human subject and a biosignature of the respective first condition and/or the second condition.

15. The method of claim 1, wherein the sample dataset of retinal signal data comprises a labeled sample dataset of retinal signal data from multiple human subjects, and wherein the retinal signal features have been determined by analyzing.

16. The method of claim 1, wherein the first condition is a medical condition and wherein the second condition is a control condition.

17. A system for predicting a probability that a human subject is subject to one or more conditions, the system comprising: an electroretinogram (ERG) system comprising: a light stimulator that emits light; a photodetector for measuring an intensity of the emitted light from the light stimulator; a spectrometer for measuring a spectrum of the emitted light from the light stimulator; and one or more electrodes for collecting retinal signal data corresponding to the human subject, and a computer system comprising at least one processor and memory storing a plurality of executable instructions which, when executed by the at least one processor, cause the computer system to: receive the retinal signal data, wherein the retinal signal data is associated with a light stimulation of the human subject's retina and includes at least one parameter, recorded by the photodetector or the spectrometer, which is voltage independent and/or time independent, and wherein the retinal signal data was collected for a signal collection time of 200 milliseconds to 500 milliseconds; extract, from the retinal signal data, one or more retinal signal features; extract, from the retinal signal features, one or more descriptors; apply the one or more descriptors to a first mathematical model and a second mathematical model, wherein the first mathematical model corresponds to a first condition and the second mathematical model corresponds to a second condition, wherein the first mathematical model and the second mathematical model are machine learning algorithms trained using a sample dataset of retinal signal data including at least one parameter which is voltage independent and/or time independent from subjects with the first condition and the second condition, respectively, thereby generating a first predicted probability for the first condition and a second predicted probability for the second condition, and wherein the at least one parameter includes the intensity of the emitted light or the spectrum of the emitted light; and display an interface comprising the first predicted probability and the second predicted probability.

18. The system of claim 17, further comprising a display, and wherein the instructions, when executed by the at least one processor, cause the computer system to output, via the display, the interface.

* * * * *